(12) United States Patent
Koyama et al.

(10) Patent No.: US 6,177,592 B1
(45) Date of Patent: Jan. 23, 2001

(54) COMPOUNDS

(75) Inventors: Nobuto Koyama; Tatsuji Enoki; Katsushige Ikai; Hua-Kang Wu; Hiromu Ohnogi; Takanari Tominaga; Eiji Nishiyama; Michio Hagiya; Hiroaki Sagawa; Hideto Chono; Ikunoshin Kato, all of Otsu (JP)

(73) Assignee: Takara Shuzo Co., Ltd., Koyto (JP)

( * ) Notice: Under 35 U.S.C. 154(b), the term of this patent shall be extended for 0 days.

(21) Appl. No.: 09/341,768

(22) PCT Filed: Feb. 26, 1998

(86) PCT No.: PCT/JP98/00815

§ 371 Date: Jul. 16, 1999

§ 102(e) Date: Jul. 16, 1999

(87) PCT Pub. No.: WO98/39291

PCT Pub. Date: Sep. 11, 1998

(30) Foreign Application Priority Data

| Mar. 5, 1997 | (JP) | 9-065616 |
| Apr. 30, 1997 | (JP) | 9-124696 |
| Jun. 16, 1997 | (JP) | 9-172782 |
| Jun. 16, 1997 | (JP) | 9-172786 |
| Aug. 8, 1997 | (JP) | 9-225533 |
| Aug. 25, 1997 | (JP) | 9-241680 |
| Oct. 1, 1997 | (JP) | 9-283204 |
| Dec. 12, 1997 | (JP) | 9-362273 |
| Dec. 16, 1997 | (JP) | 9-363281 |

(51) Int. Cl.[7] .................................................. C07C 61/06

(52) U.S. Cl. .............................................................. 562/503

(58) Field of Search ................................................ 562/503

(56) References Cited

U.S. PATENT DOCUMENTS 4,180,672  12/1979  Kurozumi et al. .

FOREIGN PATENT DOCUMENTS 53-111037  9/1978  (JP) .

*Primary Examiner*—Paul J. Killos
(74) *Attorney, Agent, or Firm*—Rhodes & Mason, PLLC

(57) ABSTRACT

A compound represented by the following formula [I] or an optically active substance or a salt thereof.

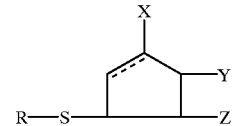

(In the formula, a bond shown by a dotted line in the five-membered ring means that said five-membered ring may be any of a cyclopentene ring having a double bond and a cyclopentane ring where said bond is saturated and, in the case of a cyclopentene ring, X is OH, Y is =O and Z is H while, in the case of a cyclopentane ring, X is =O, Y is OH and Z is OH. R is a residue after removal of an SH group from the SH-containing compound.)

22 Claims, 48 Drawing Sheets

COMPOUNDS

TECHNICAL FIELD

The present invention relates to the compounds useful in the field of pharmaceuticals having a physiological activity such as anticancer action and also relates to a method for the manufacture of said compounds.

PRIOR ART

Pharmaceuticals which have been used in clinical therapy include many agents such as anticancer agents, antibiotic substances, immunopotentiators, immunomodulators, etc. (such as alkylating agents, antimetabolites and plant alkaloids) but it can be hardly said that such a drug therapy has been completely established already.

Among those agents, prostaglandin A and J having an α, β-unsaturated carbonyl in a five-membered ring among the prostaglandins derived from natural substances have been reported to have a possibility of being used as highly safe anticancer agents due to their inhibition of DNA synthesis and various derivatives of them have been synthesized (refer to the Japanese Laid-Open Patent Publication Sho-62/96438).

PROBLEMS TO BE SOLVED BY THE INVENTION

An object of the present invention is to develop the compounds having a physiological action such as anticancer action and to offer a method for the manufacture of said compounds and pharmaceuticals containing said compounds.

MEANS TO SOLVE THE PROBLEMS

The present inventors have conducted an intensive study for achieving said object and have found that the compound represented by the formula [I] (hereinafter, referred to as "compound of the present invention") is produced by the reaction of 4,5-dihydroxy-2-cyclopenten-1-one (hereinafter, referred to as just "cyclopentenone") represented by the formula [IV] with a compound containing an SH group and that said compound of the present invention has various strong physiological activity and is useful for therapy and/or prevention of diseases being sensitive to said compound whereby the present invention has been achieved.

The present invention will be summarized to be as follows. Thus, the first feature of the present invention relates to a compound represented by the following formula [I] or an optically active substance or a salt thereof.

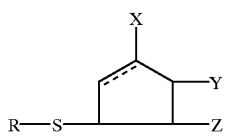

[I]

(In the formula, a bond shown by a dotted line in the five-membered ring means that said five-membered ring may be any of a cyclopentene ring having a double bond and a cyclopentane ring where said bond is saturated and, in the case of a cyclopentene ring, X is OH, Y is =O and Z is H while, in the case of a cyclopentane ring, X is =O, Y is OH and Z is OH. R is a residue after removal of an SH group from the SH-containing compound.)

An embodiment of the first feature of the present invention is a compound represented by the following formula [II] or an optically active substance or a salt thereof.

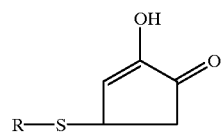

[II]

(In the formula, R is a residue after removing an SH group from the SH-containing compound.)

Another embodiment of the first feature of the present invention is a compound represented by the following formula [III] or an optically active substance or a salt thereof.

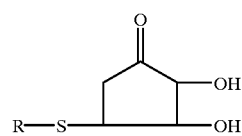

[III]

(In the formula, R is a residue after removing an SH group from the SE-containing compound.) The second feature of the present invention is a method for the manufacture of the compound represented by the formula [I] or an optically active substance or a salt thereof in the first feature of the present invention, characterized in that, a compound selected from 4,5-dihydroxy-2-cyclopenten-1-one represented by the following formula [IV] or an optically active substance or a salt thereof is made to react with a compound containing an SH group.

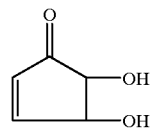

[IV]

In a preferred embodiment of the first and the second features of the present invention, the compound containing an SH group is an SH-containing amino acid or a derivative thereof.

The third feature of the present invention is a pharmaceutical agent which is characterized in containing at least one compound selected from a compound represented by the formula [I] in the first feature of the present invention or an optically active substance or a salt thereof as an effective component.

In a preferred embodiment of the third feature of the present invention, said pharmaceutical agent is a biophylactic agent (such as immunomodulator, antiallergic agent or antirheumatic agent), remedy for diabetes mellitus, anticancer agent, apoptosis inducer or an agent against pathogenic microbes (such as antiviral agent or antibacterial agent).

EMBODIMENTS OF THE INVENTION

Figure 1:
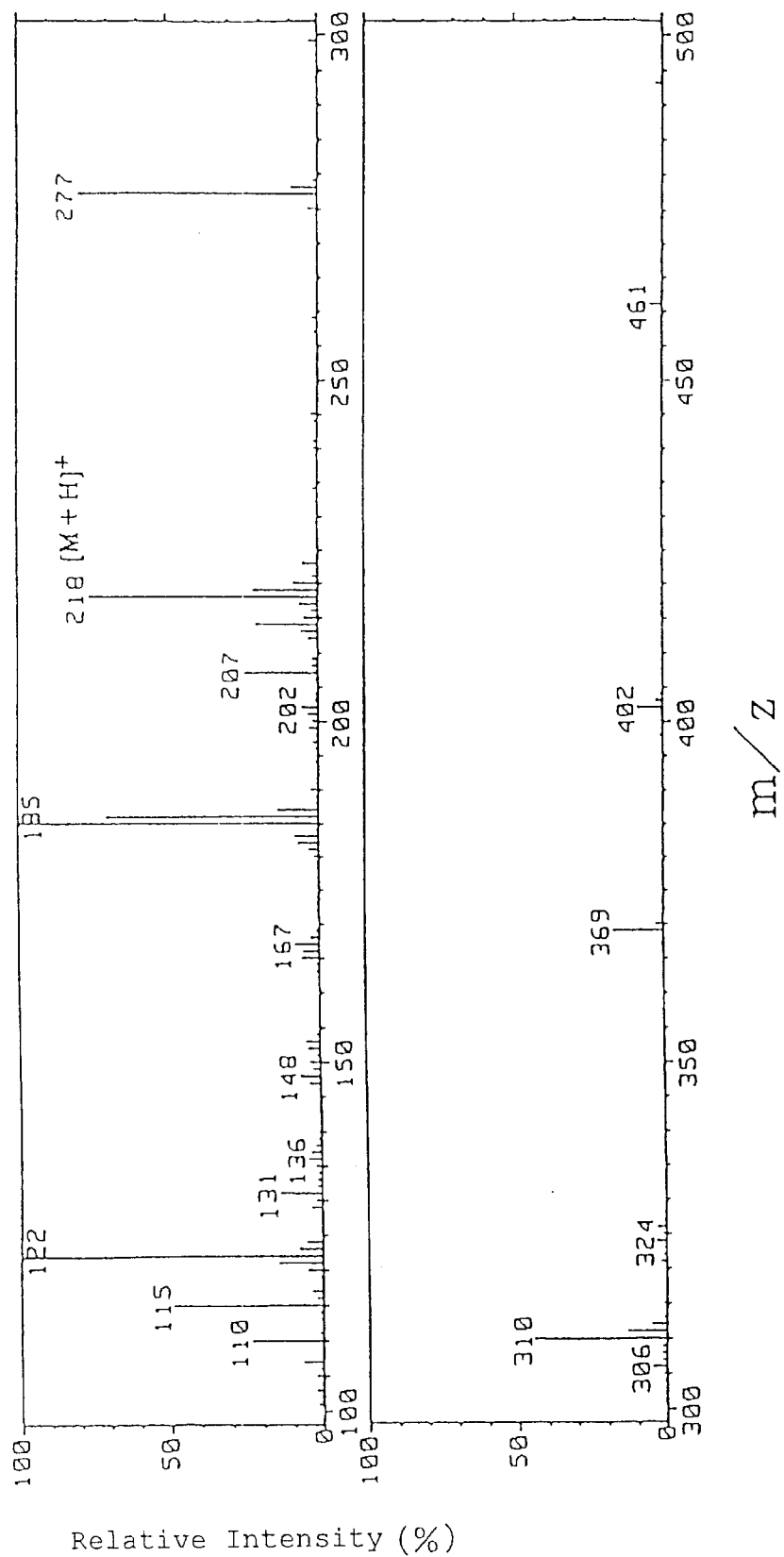
FIG. 1 shows a mass spectrum of CM1.

The present invention will now be specifically illustrated as hereinafter.

The cyclopentenone represented by the formula [IV] used in the present invention covers both isomers where the configurations of hydroxyl groups at 4- and 5-positions are cis and trans. In the present invention, any of cis-cyclopentenone, trans-cyclopentenone and a mixture of cis- and trans-cyclopentenone may be used. It is also possible to use optically active substances thereof. cis-Cyclopentenone may be prepared by a chemical synthesis [Helvetica Chimica Acta, volume 55, pages 2838–2844 (1972)]. trans-Cyclopentenone may be prepared either by a chemical synthesis [Carbohydrate Res., volume 247, pages 217–222 (1993)] or by heating uronic acid such as glucuronic acid, uronic acid derivative such as glucuronolactone or a substance containing the same (refer to PCT/JP97/03052). In the present invention, it is also possible to use such a heated product or partially purified product or purified product thereof.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP-370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

MS m/z 115 [M+H]$^+$ $^1$H-NMR (CDCl$_3$):δ 4.20 (1H, d, J=2.4 Hz, 5-H), 4.83 (1H, m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: $[\alpha]_D^{20}$ 0° (c 1. 3, water)

UV: $\lambda_{max}$ 215 nm (water)

IS (KBr method): absorptions were noted at 3400, 1715, 1630, 1115, 1060, 1025 cm$^{-1}$.

When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral Pack A, (manufactured by Daicel Chemical Industries) under such a condition that the column temperature was 40° C. and the mobile phase was hexane/ethanol (94/6).

Optical rotation of the optically resolved (−)-trans-4,5-dihydroxy-2-cyclopenten-1-one [hereinafter, referred to as (−)-cyclopentenone] is $[\alpha]_D^{20}$ −105° (c 0.30, ethanol) while that of the optically resolved (+)-trans-4,5-dihydroxy-2-cyclopenten-1-one [hereinafter, referred to as (+)-cyclopentenone] is $[\alpha]_D^{20}$ +104° (c 0.53, ethanol). Incidentally, the optical rotation was measured by the above-mentioned polarimeter of the type DIP-370 (manufactured by Nippon Bunko).

After that, each of (−)-cyclopentenone and (+)-cyclopentenone was subjected to structural analysis by means of mass analysis and nuclear magnetic resonance (NMR), measurement of UV absorption spectrum and measurement of infrared absorption spectrum by the method mentioned already. As a result, both optically active substances showed the same result as that of the cyclopentenone before the optical resolution.

Each of the optically resolved (−)-cyclopentenone and (+)-cyclopentenone was converted to a p-dimethylaminobenzoyl derivative, the circular dichroism spectrum (CD) was measured using a circular dichroism dispersimeter of type J-720 (manufactured by Nippon Bunko) and the result was applied to a dibenzoate chirality rule [J. Am. Chem. Soc., volume 91, pages 3989-3991 (1969)] to determine the configuration.

Figure 47:
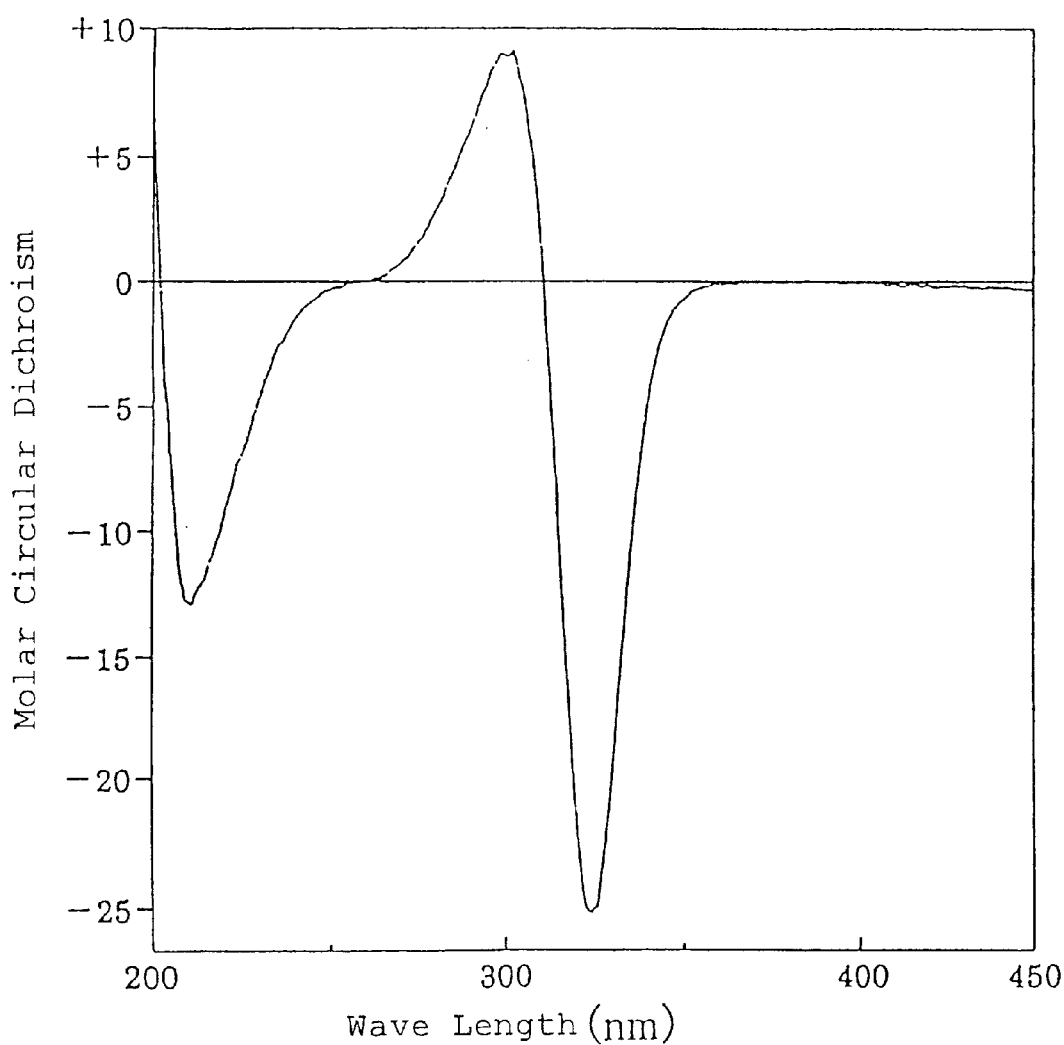
FIG. 47 shows a CD of p-dimethylaminobenzoyl derivative of (−)-cyclopentenone and a stereostructure of (−)-cyclopentenone.
Figure 47:
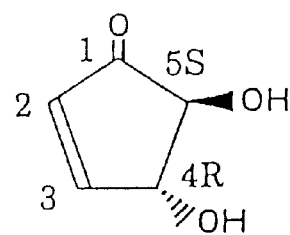

CD of p-dimethylaminobenzoyl derivative of (−)-cyclopentanone and stereostructure of (−)-cyclopentenone are shown in FIG. 47. In the drawing, the ordinate shows molar circular dichroism while the abscissa shows wave length (nm). Incidentally, the above stereostructure is given hereunder as the formula [V]

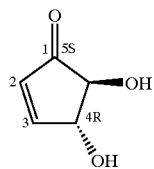

Figure 48:
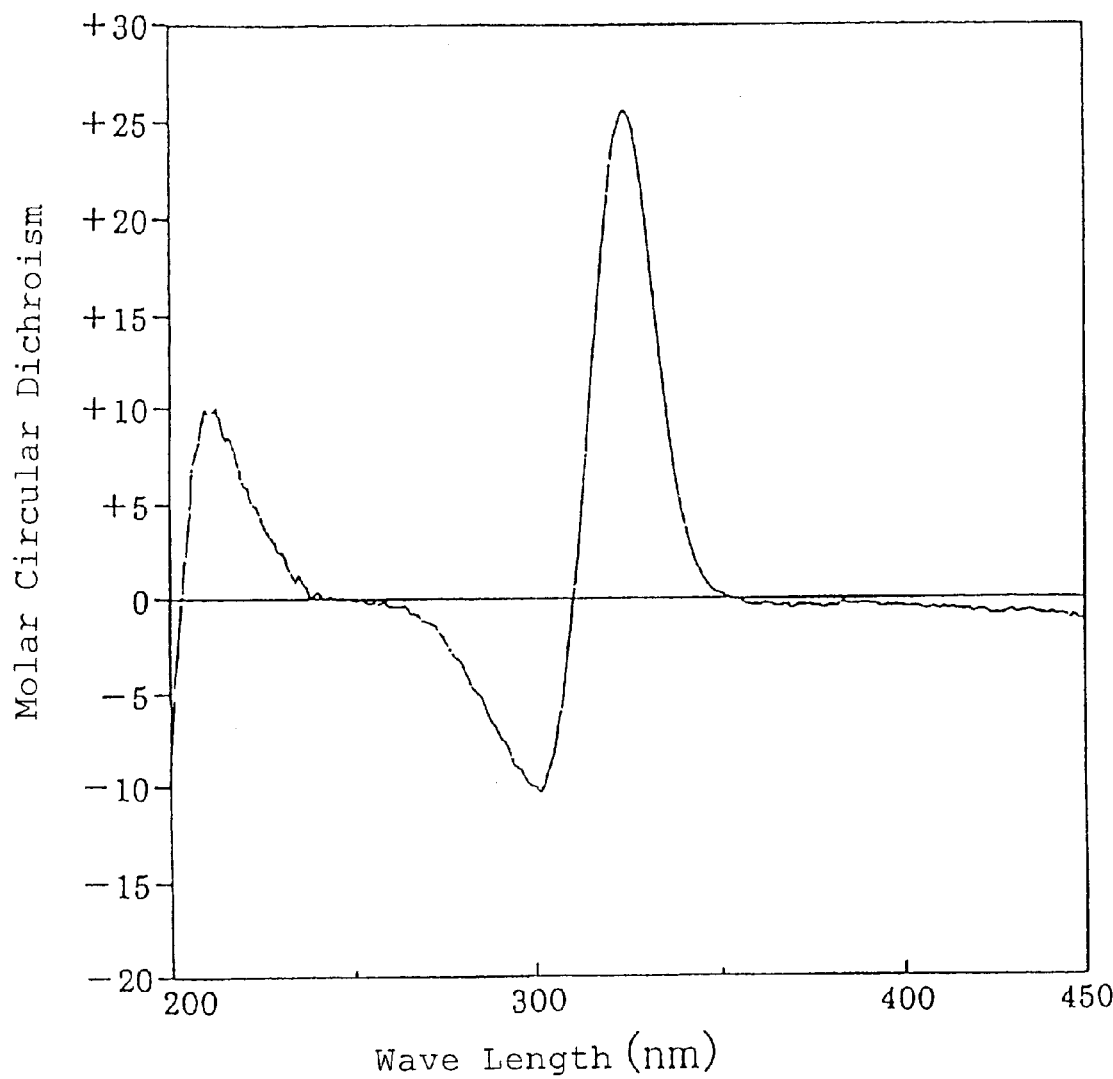
FIG. 48 shows a CD of p-dimethylaminobenzoyl derivative of (+)-cyclopentenone and a stereostructure of (+)-cyclopentenone.
Figure 48:
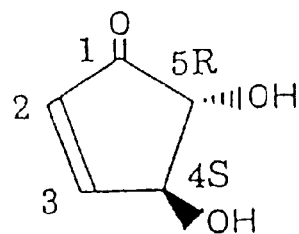

CD of p-dimethylaminobenzoyl derivative of (+)-cyclopentanone and stereostructure of (+)-cyclopentenone are shown in FIG. 48. In the drawing, the ordinate shows molar circular dichroism while the abscissa shows wave length (nm). Incidentally, the above stereostructure is given hereunder as the formula [VI]

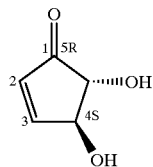

As shown in FIG. 47, FIG. 48, formula [V] and formula [VI], the (−)-cyclopentenone is (−)-(4R,5S)-trans-4,5-dihydroxy-2-cyclopenten-1-one while the (+)-cyclopentenone is (+)-(4S,5R)-trans-4,5-dihydroxy-2-cyclopenten-1-one.

The above-mentioned cyclopentenones or an optically active substance thereof may be manufactured by any method, i.e. they may be manufactured by a method disclosed in this specification or by means of chemical synthesis; and trans- and cis-cyclopentenone, a mixture thereof or optically active substances thereof may be used in the present invention as well.

Examples of the salt of the cyclopentenone or optically active substance thereof are pharmaceutically acceptable salts and they may be prepared by known converting methods.

When the cyclopentenone, an optically active substance thereof and/or a salt thereof are/is made to react with a compound containing an SH group, the compound of the present invention represented by the formula [I] is produced in the reaction solution.

When the cyclopentenone, optically active substance thereof and/or a salt thereof are/is made to react with a compound containing an SH group such as an amino acid containing an SH group or a derivative thereof under an acidic condition, the compound represented by the formula [II] (hereinafter, referred to as cyclopentenone thio derivative) is produced in the reaction solution.

There is no limitation at all for the compound containing an SH group and its examples are methanethiol, butanethiol, mercaptoethanol, amino acid containing an SH group and amino acid derivative containing an SH group. Examples of the amino acid containing an SH group are cysteine and homocysteine.

Examples of the amino acid derivative containing an SH group are derivatives of the above-mentioned amino acids such as cysteine derivatives, peptides containing cysteine and peptides containing cysteine derivatives. There is no particular limitation for the peptide containing cysteine so far as cysteine is a constituting component in the peptide. The peptide containing cysteine in accordance with the present invention covers from low molecular substances such as oligopeptides (e.g. glutathione) to high molecular ones such as protein. Peptide containing cystine or homocystine may also be used as the peptide containing cysteine or homocysteine of the present invention under the condition where it gives peptide cysteine or homocysteine during the reaction such as by combining with a reducing treatment. Incidentally, the peptide containing cysteine covers that which contains saccharide, lipid, etc. as well. In addition, it may be salt, acid anhydride, ester, etc. of the above-mentioned various substances as well. To sum up, the cyclopentenone reacts with a compound containing an SH group under an acidic condition forming a cycloptenone thio derivative.

The means for purification and isolation of the cyclopentenone thio derivative or optically active substance thereof which is prepared by the reaction of the cyclopentenone, optically active substance thereof and/or a salt thereof with a compound containing an SH group such as amino acid containing an SH group or a derivative thereof may be known purifying means such as chemical method and physical method. Thus, conventionally known methods such as gel filtration, fractionation using a molecular weight fractionating membrane, extraction with solvent, fractional distillation and various chromatographic methods using ion exchange resin, etc. are combined whereby the cyclopentenone thio derivative or an optically active substance thereof or a salt thereof can be purified and isolated. For example, when cyclopentenone and cysteine are made to react at pH 4 and at 60° C. for 16 hours, the cyclopentenone thio derivative represented by the following formula [VII] is formed in the reaction solution and, as a result of normal phase column chromatography of the reaction products containing said derivative, the cyclopentenone thio derivative can be purified and isolated.

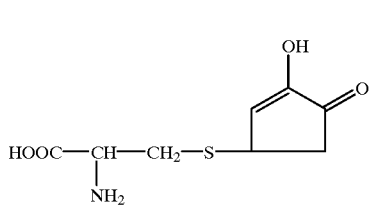

[VII]

Further, when the cyclopentenone and glutathione are made to react under an acidic condition for example, the cyclopentenone thio derivative represented by the following formula [VIII] is formed in the reaction solution and, as a result of reversed phase column chromatography or the like of the reaction products containing said derivative, said cyclopentenone thio derivative can be purified and isolated.

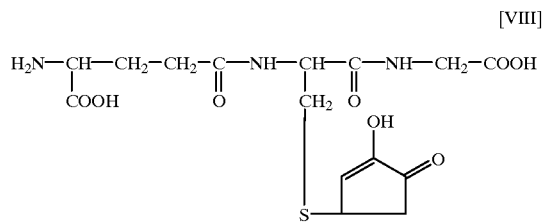

[VIII]

When the cyclopentenone, an optically active substance thereof and/or a salt thereof are/is made to react under a neutral condition with a compound containing an SH group for example, an amino acid containing an SH group or a derivative thereof for example, a compound represented by the formula [III] (hereinafter, referred to as cyclopentanone thio derivative) is formed in the reaction solution.

There is no particular limitation for the above compound containing an SH group and the above-mentioned compounds containing an SH group may be exemplified. The above reaction of the cyclopentenone, an optically active substance thereof and/or a salt thereof with a compound containing an SH group may be preferably conducted at a neutral pH.

The means for purification and isolation of the cyclopentanone thio derivative or an optically active substance thereof or salt thereof which is prepared by the reaction of the cyclopentenone, an optically active substance thereof and/or a salt thereof with a compound containing an SH group may be known purifying means such as chemical method and physical method. Thus, conventionally known methods such as gel filtration, fractionation using a molecular weight fractionating membrane, extraction with solvent, fractional distillation and various chromatographic methods using ion exchange resin, etc. are combined whereby the cyclopetanone thio derivative or an optically active substance thereof or a salt thereof can be purified and isolated.

For example, when cyclopentenone and cysteine are made to react at pH 7 and at 37° C. for 30 minutes, the cyclopentanone thio derivative represented by the following formula [IX] is formed in the reaction solution and, as a result of reversed phase column chromatography of the reaction products containing said derivative, the cyclopentanone thio derivative can be purified and isolated.

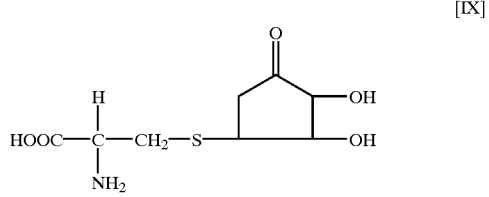

[IX]

Further, when the cyclopentenone and glutathione are made to react under a neutral condition for example, the cyclopetanone thio derivative represented by the following formula [X] is formed in the reaction solution and, as a result of reverse phase column chromatography or the like of the reaction products containing said derivative, said cyclopentanone thio derivative can be purified and isolated.

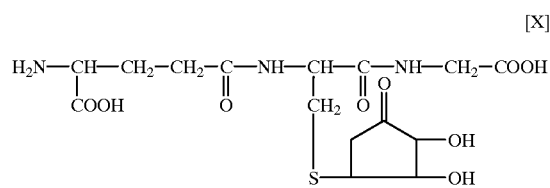

[X]

Separation of the optically active substances of the compound of the present invention can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used.

A method using a chiral stationary phase, a method using a chiral eluate, separation as a diastereomer, etc. may be used in an optical resolution by liquid chromatography.

A stationary phase of an amide type, that of a urea type, that of a ligand exchange type, polysaccharide-polysaccharide derivative stationary phase, protein stationary phase, polymethacrylate stationary phase, polymethacrylamide stationary phase, etc. may be used as a chiral stationary phase.

With regard to an eluting liquid, that of a hexane type, an alcohol type, an aqueous (buffer) type, etc. may be suitably used taking the combination with the above-mentioned stationary phase into consideration.

With regard to the salt of the compound of the present invent-on or optically active substance thereof, salts which are acceptable as pharmaceuticals are exemplified and they may be prepared by converting by means of known methods. the compound of the present invention, an optically active substance thereof or a salt thereof has physiological activities such as anticancer activity, activity of growth inhibition of cancer cells, apoptosis-inducing activity, activity of topoisomerase II inhibition, induction activity of the cancer cell differentiation, antirheumatic activity, activity of chronic articular rheumatism inhibition, activity of inducing the Fas antigen production, antibacterial activity, antiviral activity, activity of improving the hepatic function, activity of inducing the heat shock protein, normalizing activity of the blood components, enhancer activity of the cancer immunity, anti-inflammation activity, inhibition activity of tumor necrosis factor expression, inhibition activity of nitrogen monoxide production, immunomodulating activity such as inhibition activity of delayed type hypersensitivity, inhibition activity of lymphocyte transformation, inhibition activity of mixed lymphocyte reaction, inhibition activity of IgE production and inhibition activity of carrageenan edema and, due to those activities, pharmaceutical agent containing as an effective component at least one compound which is selected from the compound of the present invention, an optically active substance thereof and a salt thereof is useful as a drug acting biophylaxic function such as pharmaceutical preparation acting the antibody production function, anti-inflammatory agent, antiallergic agent, antirheumatic agent and interferon inducer, a drug acting the saccharide metabolism such as remedy for diabetes mellitus and a drug acting the pathogenic organisms such as antibacterial agent and antiviral agent. Accordingly, the pharmaceutical agent obtained by the present invention is quite useful as a drug for the diseases which show sensitivity to the compound of the present invention, an optically active substance thereof or a salt thereof, i.e. as a drug for therapy or prevention of, for example, cancer, viral diseases, rheumatism, diabetes mellitus, allergy, autoimmune diseases, inflammation, etc.

The compound of the present invention, an optically active substance thereof or a salt thereof has a cell growth suppressing action and anticancer action to cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colon cancer cells HCT 116, human colon cancer cells SW 480, human colon cancer cells WiDr, stomach cancer cells AGS and myeloma cells. Thus, the compound of the present invention, an optically active substance thereof or a salt thereof can be used as an effective component of anticancer agent. Further, those compounds have an apoptosis-inducing action to those cancer cells too. Mechanism of the action for inhibiting the cancer cell growth of the compound of the present invention, an optically active substance thereof or a salt thereof does not limit the scope of the present invention at all and, for example, a topoisomerase II inhibiting action and an apoptosis inducing action to cancer cells is covered by anticancer activity of the present invention as well.

When at least one of the compound selected from the compound of the present invention, an optically active substance thereof or a salt thereof having anticancer action is used as an effective ingredient and is made into a pharmaceutical preparation by compounding with known pharmaceutical carriers, it is now possible to prepare an anticancer agent. Generally, at least one of the compound selected from the compound of the present invention, an optically active substance thereof or a salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where at least one of the compound selected from the compound of the present invention, an optically active substance thereof or a salt thereof which is an effective ingredient of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The anticancer agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated and it is not constant but, usually, the amount of the cyclopentenone and/or its optically active substance contained in the preparation is from 0.1 $\mu$g to 200 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The compound of the present invention, an optically active substance thereof or a salt thereof has an anticancer action and, at low concentrations, it shows an ability of inducing the differentiation of cancer cells whereby it is useful as a differentiation inducer (a decancerizing agent) for cancer cells. An inducer for cancer cell differentiation containing at least one of the compound selected from the compound of the present invention, an optically active substance thereof or a salt thereof as an effective ingredient can be made into pharmaceutical preparations in accordance with the above-mentioned method for anticancer agents and can be administered by the method similar to that for anticancer agents.

Dose as an inducer for cancer cell differentiation is appropriately decided by its form of preparation, method of administration, purpose of use and age, body weight and symptom of the patient to be treated and it is not constant but, usually, the amount of at least one of the compound selected from the compound of the present invention, an optically active substance thereof or a salt thereof contained in the preparation is from 0.1 $\mu$g to 100 mg/kg per day (for adults). Of course, the dose may vary depending upon various conditions and, there ore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The above-mentioned inducer for cancer cell differentiation can be used in a method for induction of cancer cell differentiation. Thus, when at least one of the compound selected from the compound of the present invention, an optically active substance thereof or a salt thereof is used as an effective ingredient, it is possible to differentiate the cancer cells and such a method is useful for elucidation of mechanism for induction of cancer cell differentiation, for screening of the differentiation inducers, etc.

The compound of the present invention or an optically active substance thereof or a salt thereof has an antibacterial action and, when at least one compound selected from such compounds is used as an effective component and is made into a pharmaceutical preparation by combining with known pharmaceutical carriers, an antibacterial agent can be manufactured. Said pharmaceutical preparation can be manufactured by the same manner as in the case of the above-mentioned anticancer agent and can be administered by the same manner as in the case of the anticancer agent.

Dose as an antibacterial agent is appropriately decided by its form of preparation, method of administration, purpose of use and age, body weight and symptom of the patient to be treated and it is not constant but, usually, the amount of at least one compound selected from the compound of the present invention, an optically active substance thereof or a salt thereof contained in the preparation is from 10 $\mu$g to 20 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the absent can be taken on a routine basis. In addition, the compound of the present invention, an optically active substance thereof or a salt thereof may be used as a material for antibacterial food and beverage. Further, it may be used together with ethanol, glycine, sodium acetate, ascorbic acid, glycerol fatty acid esters, salt, EDTA and other antibiotic substances.

The antibacterial agent of the present invention containing at least one of the compound selected from the compound of the present invention, an optically active substance thereof or a salt thereof as an effective ingredient may be used as an antiseptic agent for improving the preservation of food or beverage. In addition, a compound selected from those compounds is added to food or beverage whereby it may be used in an antiseptic method for food or beverage. Amount of the compound of the present invention, an optically active substance thereof or a salt thereof to be added to food or beverage may vary depending upon the type of the food or beverage and the amount meeting with the object may be added.

One method of using the antibacterial agent of the present invention is that where the agent is added to food or to beverage by an appropriate method. Although the common method is to add them/it during the manufacturing steps of the food or beverage, a method where the food is dipped in a solution containing the compound of the present invention, an optically active substance thereof or a salt thereof may be used as well. It is also possible to conduct a method of adding it to the food together with a method of dipping the food in the solution.

When the antibacterial agent of the present invention is used as an antiseptic agent, preservation of food or beverage can be further improved. In the case of frozen food and frozen dessert, growth of contaminated microorganisms in the processing step prior to the freezing can be suppressed whereby a very favorable result in terms of hygiene can be obtained. The antibacterial agent of the present invention is effective to both gram-positive and gram-negative bacteria and is very effective to bacteria causing food poisoning, for example, to drug-resistant bacteria such as methicillin-resistant *Staphylococcus aureus* and Salmonella, enterotoxin-producing *Staphylococcus aureus*, *Bacillus cereus* of a emetic type, *Bacillus cereus* of a diarrheal type and enterohemorrhagic *Escherichia coli* 0–157. It is also effective to hiochi bacteria. Further, it shows an antibacterial action to microorganisms causing diseases which are caused by microorganisms such as *Legionella pneumophila* (a microorganism causing legionnaire's disease), *Vibrio parahaemolyticus* (a microorganism causing food poisoning), *Helicobacter pylori* (a microorganism causing ulcer), *Campylobacter jejuni* (a microorganism causing enterogastrisis), etc. including *Legionella pneumophila* (ATCC 33153), *Vibrio parahaemolyticus* (ATCC 17802), *Helicobacter pylori* (NCTC 11637), *Campylobacter jejuni* (ATCC 29428), etc. It is also effective to microorganisms such as yeast and fungi. Incidentally, sterilization of clothing, bed sheet, etc. can be conducted using the antibacterial agent of the present invention and, when the antibacterial agent of the present invention is sprinkled or when wiping-off with the antibacterial agent of the present invention is conducted, it is possible to sterilize (both to remove and to kill the bacteria) the thing to be sterilized. For example, when it is added to water for air-conditioning of office buildings, legionnaire's disease can be prevented.

The antibacterial agent of the present invention has an antibacterial activity to bacteria for dental caries and those for periodontal disease and an intraoral preparations containing the antibacterial agent of the present invention can be offered. The form of the intraoral preparation maybe a known one such as liquid or paste. An example of the intraoral preparation is a dentifrice. The dentifrice may be in a known form such as liquid, paste or powder. There is no particular limitation for the amount of the compound of the present invention, an optically active substance thereof or a salt thereof in the dentifrice and, if an effective concentration to the bacteria for dental caries and for periodontal disease is contained therein, that will be enough. Known additives such as moisturizing agents, surface-active agents, binders, perfumes, sweetening agents, etc. may be added to the dentifrice.

It is possible to offer antibacterial cosmetics using the antibacterial agent of the present invention. Examples of the antibacterial cosmetics of the present invention are in the forms of basic cosmetics such as cream, milky lotion, lotion, face-washing material and pack; make-up cosmetics such as lipstick and foundation; body soap; and soap containing an effective amount of at least one of the compound selected from the compound of the present invention, an optically active substance thereof or a salt thereof. This is useful to hair as well and can be made into the hair care products including hair products such as hair tonic, hair liquid, hair set lotion, hair blowing preparation, hair cream and hair coat; and hair toiletry products such as shampoo, rinse and hair treatment. Its amount in the cosmetics may be appropriately decided depending upon its antibacterial activity. With regard to other ingredients, those which have been commonly compounded with cosmetics may be used. The antibacterial cosmetic product effectively acts the microorganisms causing atopic dermatitis as well and it shows significant effect for improving and preventing the atopic dermatitis.

It is also possible to offer a bathing agent using the antibacterial agent of the present invention. The bathing agent of the present invention may be made into a form of powder, granules, solid, liquid, etc. containing the effective amount of at least one of the compound selected from the compound of the present invention, an optically active substance thereof or a salt thereof. The compounding amount to the bathing agent may be appropriately decided depending upon the desired antibacterial activity. With regard to other ingredients for the bathing agent, those which have been commonly compounded with bathing agents may be used. The bathing agent of the present invention effectively acts the microorganisms causing atopic dermatitis as well and it shows significant effect of improving and preventing the atopic dermatitis. It is effective to exterminate the causing microorganism from the bathroom.

Further, food or beverage containing at least one of the compound selected from the compound of the present invention, an optically active substance thereof or a salt thereof is very useful for improvement and/or prevention of food poisoning, enterogastrisis, etc.

The apoptosis inducer of the present invention contains at least one of the compound selected from the apoptosis-inducing compound of the present invention, an optically active substance thereof or a salt thereof as an effective ingredient. It can be made into pharmaceutical preparations by the same manner as in the above-mentioned case of anticancer agents and is administered by the same manner as in the anticancer agents.

The dose as the apoptosis inducers is not particularly specified but may be appropriately determined depending upon the dosage form, administration method, purpose of the use and age, body weight, conditions, etc. of the patient to whom the inducer is administered. Usually, however, the amount of at least one of the compound selected from the compound of the present invention, an optically active substance thereof or a salt thereof contained in the preparation for an adult is 0.1 $\mu$g-100 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

Unlike necrosis which is a pathogenic death of cells, apoptosis is believed to be a death which is initially programmed in the gene of the cell itself. Thus, the gene which programs the apoptosis is activated by certain external or internal causes whereby programmed cell death gene protein is produced based upon said gene and then the cell itself is decomposed and dead by the resulting programmed death protein.

The apoptosis inducer of the present invention is quite useful since it is capable of induction of such apoptosis in desired tissues and cells and able to exclude the unnecessary cells or the pathogenic cells from living organisms in a natural state.

The apoptosis inducer of the present invention can be used in a method for the induction of apoptosis. Thus, when at least one of the compound selected from the compound of the present invention, an optically active substance thereof or a salt thereof is used as an effective ingredient, it is possible to induce apoptosis and said method is useful, for example, for elucidation of a mechanism for apoptosis induction and for screening of apoptosis inducers and apoptosis induction inhibitors.

The compound of the present invention or an optically active substance thereof or a salt thereof has an antirheumatic activity and, when at least one compound selected from such compounds is used as an effective component and is made into a pharmaceutical preparation by combining with known pharmaceutical carriers, an antirheumatic agent can be manufactured. Said pharmaceutical preparation can be manufactured by the same manner as in the case of the above-mentioned anticancer agent and can be administered by the same manner as in the case of the anticancer agent.

The dose as the antirheumatic agent of the present invention is not particularly specified but may be appropriately determined depending upon the dosage form, administration method, purpose of the use and age, body weight, conditions, etc. of the patient to whom the agent is administered. Usually, however, the amount of at least one of the compound selected from the compound of the present invention, an optically active substance thereof or a salt thereof contained in the preparation for an adult is 0.1 $\mu$g-200 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well. Further, the compound of the present invention, an optically active substance thereof or a salt thereof may be used as a material for the pharmaceutical agent of the present invention.

The compound of the present invention, an optically active substance thereof or a salt thereof has various physiological activity such as anti-inflammatory activity to arthritis, etc., inhibition activity of carrageenan edema, inhibition activity of tumor necrosis factor production, increasing activity of interleukin-10 production, inhibition activity of nitrogen monoxide production, induction activity of Fas antigen production, immunomodulating activity such as inhibition activity of delayed type hypersensitivity, inhibition activity of lymphocyte transformation, inhibition activity to mixed lymphocyte reaction, inhibition activity to IgE production, etc. Thus, the drug such as anti-inflammatory agent or inflammation preventer, inhibitor of tumor necrosis factor production or preventer of tumor necrosis factor production, enhancer of interleukin-10 production, immunomodulator, inhibitor of nitrogen monoxide production, inducer of Fas antigen production, immunomodulator, inhibitor of IgE production, inhibitor of delayed type hypersensitivity and antiallergic agent containing at least one compound selected from the compound of the present invention, an optically active substance thereof or a salt thereof can be made into pharmaceutical preparations by the same manner as in the case of the above anti-rheumatic agent and can be administered by the same manner as above.

The dose of those preparations is not particularly specified but may be appropriately determined depending upon the dosage form, administration method, purpose of the use and the age, body weight, conditions, etc. of the patient to whom the inducer is administered. Usually, however, the amount of at least one of the compound selected from the compound of the present invention, an optically active substance thereof or a salt thereof contained in the preparation for an adult is 0.1 μg-200 mg/kg per day. As a matter of course, the dose may vary depending upon various factors and, therefore, the dose less than the above-mentioned one may be sufficient in some cases while, in other cases, the dose more than the above may be necessary. For example, in the case of anti-inflammatory agent and an inhibitor of tumor necrosis factor production, the amount of one or more compound selected from the compound of the present invention, an optically active substance thereof or a salt thereof contained in the preparation is preferably 10 pg-50 mg/kg per day for adult while, in the case of inhibitor of nitrogen monoxide production, the amount of one or more compound selected from the compound of the present invention, an optically active substance thereof or a salt thereof contained in the preparation is preferably 0.1 μg-20 mg/kg per day for adult. Depending upon the object of use, the amount of the effective component in the preparation may be controlled.

The agent of the present invention may be administered orally as it is and, further, the agent may be taken daily after adding to common food and/or beverage as well.

Rheumatism is an autoimmune disease where hindrance takes place in perisoteal cells and cartilage cells and the antiallergic agent of the present invention is useful as a therapeutic agent to autoimmune diseases as well.

The compound of the present invention, an optically active substance thereof and a salt thereof inhibits the production of tumor necrosis factor which is believed to directly cause the inflammation in organ-specific autoimmune diseases such as chronic rheumatoid arthritis or inflammatory diseases and enhances the production of interleukin-10 which is a ThI inhibiting cytokine. Accordingly, symptoms of inflammation such as rheumatism which is an organ-specific autoimmune disease, particularly chronic rheumatoid arthritis are improved; inflammation markers such as C-reactive protein (CRP) value, rheumatoid factor (RF) value and erythrocyte sedimentation rate (blood sedimentation) are greatly decreased; and complications such as dysbasia is significantly improved as well.

Tumor necrosis factor was found as a factor which induces hemorrhagic necrosis to tumor site and, at present, it is recognized as cytokine which broadly participates in inflammatory-based biophylaxis and immune function. Failure in a regulation of production of this tumor necrosis factor causes various inconveniences to the host, and excess or unmodulated production of tumor necrosis factor is related to many diseases including chronic rheumatoid arthritis, rheumatic myelitis, osteoarthritis, gouty arthritis, sepsis, septic shock, endotoxin shock, sepsis by gram-negative bacteria, toxic shock syndrome, cerebral malaria, chronic pneumonia, graft versus host disease, rejection reaction to allograft, influenza and other fever and muscular pain by infectious diseases, secondary cachexia to infection or malignant tumor, secondary cachexia to human acquired immunodeficiency syndrome (AIDS), AIDS, AIDS-related syndrome, keloid formation, ulcerative colitis, multiple sclerosis, autoimmune diabetes mellitus and systemic lupus erythematosus [Molecular Medicine, volume 33, pages 1010–1020 and pages 1182–1189 (1996)]. The inhibitor of tumor necrosis factor production of the present invention is useful for therapy of diseases which is mediated or worsened by tumor necrosis factor. The present invention further offers a method for controlling the production of tumor necrosis factor where at least one compound selected from the compound of the present invention, an optically active substance thereof or a salt thereof is used as an effective component. The present invention furthermore offers food or beverage containing at least one compound selected from the compound of the present invention, an optically active substance thereof or a salt thereof which improves the symptom of the disease or which prevents the disease mediated or worsened by tumor necrosis factor.

Nitrogen monoxide (hereinafter, abbreviated as NO) is a main factor of endothelium-dependent relaxing factor (EDRF) [Nature, volume 327, pages 524–526 (1987)]. The present invention offers a drug containing at least one compound selected from the compound of the present invention, an optically active substance thereof or a salt thereof as an effective component for the therapy or prevention of the diseases requiring the inhibition of NO production. There is no particular limitation for the diseases which require the inhibition of NO production and the examples thereof are systemic hypotension caused by toxic shock or by therapy of certain cytokine, lowering in blood pressure response, autoimmune diseases, inflammation, arthritis, rheumatic arthritis, diabetes mellitus, inflammatory intestine diseases, insufficiency of blood vessel function, etiological dilation of blood vessel, damage of tissues, cardiovascular ischemia, sensitivity to pain, cerebral ischemia, diseases caused by angiogenesis, cancer, etc. The diseases include those which are mentioned in the Japanese Laid-Open Patent Publications Hei-09/504,524; 09/505,288; 08/501,069; 08/512,318; and 06/508,849.

The inhibitor of NO production containing at least one compound selected from the compound of the present invention, an optically active substance thereof or a salt thereof as an effective component is useful for the study of mechanism of NO production and of mechanism of biological activity of NO and, in addition, it may be used for screening the substances participating in the mechanism of NO production.

The compound of the present invention, an optically active substance thereof or a salt thereof has an inhibition activity of NO production in the NO-productive cells. For example, when endotoxin (lipopolysaccharide or LPS) is added to macrophage cell strain, inducible NO synthetase (NOS) is expressed and NO is secreted into a medium while, when LPS is added tn the coaexistince of the compound of the present invention, an optically active substance thereof or a salt thereof, production of NO is inhibited. When NO production is induced by treating with LPS, survival rate of cells decreases due to cytopathy activity of NO but, when the compound of the present invention, an optically active substance thereof or a salt thereof is added during the treatment with LPS, production of NO decreases and disturbance to cells suppresses as well.

Angiogenesis is essential for growth of solid carcinoma and angioendothelial growth factor/vascular endothelial growth factor (VEGF) plays an important role in this step.

In various cancer cells, VEGF is induced by NO. When the compound of the present invention, an optically active substance thereof or a salt thereof inhibits the NO production, VEGF production of cancer cells is inhibited as well and, as a result, angiogenresis around the cancer tissues is inhibited. When the compound of the present invention, an optically active substance thereof or a salt thereof is administered to mouse wherein solid cancer is formed by a subcutaneous transplantation of cancer cells, formation of blood vessel around the cancer tissues becomes insufficient and cancer is detached therefrom.

Nitrosoamines are a series of compounds which is synthesized by nitroso group addition to secondary amine and several hundreds of nitrosoamines have been known. Many of them damage the DNA, and have carcinogenicity to animals. It has been said that nitrosoamines are greatly related to cancer generation in human being as well and are usually produced in stomach by the reaction of nitrite with amine. Even under a physiological condition of neutral pH, NO reacts with amine to afford nitrosoamine. In addition, NO production is increased in the patients infected by oriental liver fluke and those suffering from hepatic cirrhosis which is highly related to cancer immunologically. Accordingly, when increase of the NO production is suppressed by administration of the compound of the present invention, an optically active substance thereof or a salt thereof, it is possible to prevent the generation of cancer, especially in a high-risk group. As such, the compound of the present invention, optically active substance thereof or salt thereof exhibits an anticancer action in the two steps of inhibition of carcinogenesis and also of inhibition of angiogenesis in cancer tissues.

Further, NO induces the edema which is noted characteristically in inflammatory lesions, i.e. blood vessel permeability [Maeda, et al., Japanese Journal of Cancer Research, volume 85, pages 331–334 (1994)] and also induces the biosynthesis of prostaglandins which are inflammation mediators [Salvemini, et al., Proceedings of National Academy of Sciences, U. S. A., volume 90, pages 7240–7244 (1993)]. On the other hand, it is believed that NO quickly reacts with superoxide radicals and the resulting peroxy nitrite causes inflammatory cells and tissue damages.

When activated immune cells are taken in organ and cytokine is released therefrom, production of NO is induced. Insulin-dependent diabetes mellitus is a diseases caused by a specific destruction of Langerhans β cells and the destruction is done by NO. In addition, the joint fluid of lesions of patients suffering from chronic articular rheumatism, osteoarticular rheumatism, gouty arthritis and arthritis accompanied by Behcet disease contains higher concentrations of NO as compared with the joint fluid in the normal joints of such patients or in the joints of healthy persons. When the compound of the present invention, an optically active substance thereof or a salt thereof is administered to such patients, production of NO in the lesions is inhibited and the symptom is improved.

During cerebral ischemia and after re-perfusion, production of NO increases and, as a result, cerebral tissues are damaged. When the compound of the present invention, an optically active substance thereof or a salt thereof is administered to the patient during cerebral ischemia, damage of the cerebral tissues is reduced and prognosis is improved.

Cell surface antigen which is called as Fas antigen (APO-1 antigen or CD95) had been receiving attention as molecules for indicing the apoptosis [Cell, volume 66, pages 233–243 (1991); J. Exp. Med., volume 169, pages 1747–1756 (1989) J. Biol. Chem., volume 267, pages 1070–2901 (1992); and J. Immunology, volume 184, pages 1274–1279 (1992)].

Fas antigen is expressed in immune cells such as thymus cells, T cells, cytotoxics T cells, B cells and cells. Against invasion of foreign non-autoantigen, immune system induces immunoreaction whereby the non-autoantigen is excluded. However, it does not show immunoreaction but self tolerance is established. This is because lymphocytic stem cells having autoreactivity is subjected to removal of clones which is a negative selection whereby the exclusion takes place by death of cells by apoptosis. However, when those cells are not subjected to apoptosis due to some abnormality in living body such as genetic deficiency of Fas antigen, the autoreactive T cells for example are accumulated in peripheral areas. In normal Living body, self tolerance is available even for B cells which are the cells in charge of immune and those autoreactive B cells are usually dead due to apoptosis but, when the autoreactive B cells are not subjected to apoptosis due to abnormality such as genetic deficiency of Fas antigen, the autoreactive B cells are accumulated in peripheral areas. In addition, in the case of articular rheumatism, the above-mentioned abnormality in autoreactive lympocytes and abnormality in turn-over of synovial cells are some of the causes of the diseases.

An inducer for production of Fas antigen in which at least one compound selected from the compound of the present invention, an optically active substance thereof or a salt thereof is an effective component is useful for induction of apoptosis of unnecessary cells for constituting the living body which are not discharged from living body due to abnormality of turnover and autoreactive lymphocytes and can be used in a method of inducing the Fas antigen production. The agent containing at least one compound selected from the compound of the present invent-on, an optically active substance thereof or a salt thereof as an effective component is also useful as an agent for prevention or therapy of the diseases accompanied by abnormal production of Fas antigen. In the present invention, there is no particular limitation for the diseases accompanied by abnormal production of Fas antigen and its examples are articular rheumatism and autoimmune diseases caused by autoreactive T cells and autoreactive B cells, etc. including the diseases mentioned in the specification of WO97/0965.

The compound of the present invention, an optically active substance thereof or a salt thereof has an immunomodulating activity such as enhancer activity of interleukin-10 production, inhibition activity of delayed type hypersensitivity reaction, inhibition activity of lymphocyte transformation, inhibition activity of mixed lymphocyte reaction, inhibition activity of IgE production and inhibition activity of carrageenan edema and the immunomodulator containing at least one compound selected from the compound of the present invention, an optically active substance thereof or a salt thereof as an effective component is useful as an agent for therapy or prevention of the diseases caused by abnormality of those immune system and immune factor.

Thus, as a result of reduction of interleukin-10 production, Th1 is activated and inflammation of Th1-dominant autoimrrmune is induced. This inflammation participates in organ-specific autoimmune diseases such as nephritis and hepatitis as well as graft rejection and allergic contact dermatitis. The immunomodulator of the present invention enhances the interleukin-10 production and inhibits the Th1 activity whereby it is useful for the therapy and prevention of those diseases.

Lymphocyte transformation is a reaction in which mitogen is bonded to the receptor on the surface of lymphocyte to activate the lymphocyte whereby division and growth thereof are promoted. Mixed lymphocyte reaction is a reaction in which lymphocytes obtained from animals of the same species but different strain are subjected to a mixed culture whereupon activation of lymphocytes due to disagreement of main tissue-adaptable antigens is induced and division and growth of the lymphocytes are promoted. The above-mentioned immunomodulator inhibits those reactions and is particularly useful for therapy or prevention of the chronic autoimmune diseases caused by abnormal promotion of lymphocytes such as chronic nephritis, chronic colitis, diabetes mellitus of type I and chronic articular rheumatism and is also useful in inhibiting the graft rejection.

Carrageenan podedema model is a reaction in which carrageenan which is an inflammation inducer is subcutaneously injected to paws to induce inflammation cells such as macrophage and neutrophils whereby blood vessel permeability is enhanced by inflammatory factors produced from those cells inducing the edema. The inhibiting action of the above-mentioned immunonodulator to edema is useful for therapy or prevention of diseases requiring control of enhancement of blood vessel permeability such as chronic articular rheumatism.

In allergic diseases represented by asthma and atopic dermatitis, release of chemical mediators from mast cells plays an important role in allergic reaction. This reaction is induced when IgE is bonded to receptors on cell membrane to form a cross-linkage and the immunomodulator of the present invention inhibits the production of IgE and is quite useful for improvement of symptoms and/or prevention of diseases mediated or worsened by the IgE production such as allergic diseases caused by IgE including bronchial asthma, allergic rhinitis, atopic dermatitis, allergic conjunctivitis, urticaria, anaphylactic shock, etc. In addition, the immunomodulator of the present invention inhibits the delayed type hypersensitivity reaction and is useful for therapy and prevention of the diseases accompanied by the delayed type hypersensitivity such as contact hypersensitivity, allergic contact dermatitis, bacterial allergy, fungal allergy, viral allergy, drug allergy, thyroiditis and allergic encephalitis.

As a result of pathological studies for diabetes mellitus in recent years, it was reported that normal fat cells play an important role in normal systemic insulin action and that, for a smooth progress of saccharide metabolism, normal fat cells are necessary [Jikken Igaku, volume 14, pages 61–68 (1996)].

The compound of the present invention, an optically active substance thereof or a salt thereof has an ability of inducing the differentiation of precursor of fat cells such as precursor of fibroblast and induces the differentiation of said cells to fat cells. Therefore, when the compound of the present invention, an optically active substance thereof or a salt thereof is administered, normal fat cells increase whereby symptom of diabetes mellitus is improved.

The compound of the present invention, an optically active substance thereof or a salt thereof has a hypoglycemic activity and it is now possible to prepare an agent for therapy or prevention of diabetes mellitus containing at least one compound selected from the compound of the present invention, an optically active substance thereof or a salt thereof as an effective component.

Thus, when at least one compound selected from such compounds is used as an effective component and is made into a pharmaceutical preparation by combining with known pharmaceutical carriers, it is now possible to prepare an agent for therapy or prevention of diabetes mellitus. Said pharmaceutical preparation can be manufactured by the same manner as in the case of the above-mentioned anti-cancer agent and can be administered by the same manner as in the case of the above-mentioned drugs.

The dose as the agent for therapy or prevention of diabetes mellitus is not particularly specified but may be appropriately determined depending upon the dosage form, administration method, purpose of the use and age, body weight, conditions, etc. of the patient. Usually, however, the amount of at least one of the compound selected from the compound of the present invention, an optically active substance thereof or a salt thereof contained in the preparation for an adult is 10 pg-200 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

Further, the compound of the present invention, an optically active substance thereof or a salt thereof may be used as a material for the food or beverage for the improvement or prevention of diabetes mellitus. When a product containing the compound of the present invention, an optically active substance thereof or a salt thereof is taken, diabetes mellitus is improved and the amount of sugar in urine significantly decreases. In addition, complications such as hypogonadism is markedly improved. Further, hyperlipemia is improved as well.

The compound of the present invention, an optically active substance thereof or a salt thereof has an activity of improving the hyperlipemia or activity of reducing the total cholesterol in serum, activity of reducing the triglycerides in serum and activity of reducing the free fatty acids in serum and, when at least one compound selected from the compound of the present invention, an optically active substance thereof or a salt thereof having such an activity is used as an effective component and is made into pharmaceutical preparation by combining with known pharmaceutical carriers, it is now possible to manufacture an agent for therapy or prevention of hyperlipemia. Manufacture of such a preparation can be conducted by the same manner as in the case of the above-mentioned therapeutic or preventive agent for diabetes mellitus and such a preparation can be administered by the same manner as in said therapeutic or preventive agent for diabetes mellitus. In addition, the compound of the present invention, an optically active substance thereof or a salt thereof may be used as a material for food or beverage for improvement or prevention of hyperlipemia. When the product containing the compound of the present invention, an optically active substance thereof or a salt thereof is taken, hyperlipemia is improved and lipid level in blood is significantly reduced.

In addition, when the compound of the present invention, an optically active substance thereof or a salt thereof having an ability of inducing the differentiation of the fat cell precursor to fat cells is used as an effective component and made into pharmaceutical preparations combining with the known pharmaceutical carriers, it is now possible to manufacture an agent for inducing the differentiation of precursor fatty cells to fatty cells. Manufacture of said agent may be conducted by the same manner as in the case of above-mentioned therapeutic or preventive agent for diabetes mellitus and the agent may be administered by the same manner as in the case of the agent for therapy or prevention of diabetes mellitus.

Further, the compound of the present invention, an optically active substance thereof or a salt thereof has an inhibition activity of the production of tumor necrosis factor and is useful for therapy or prevention of non insulin dependent diabetes mellitus caused by tumor necrosis factor [Nature, volume 389, pages 610–614 (1997)].

The compound of the present invention, an optically active substance thereof or a salt thereof has an antiviral activity and, when at least one compound selected therefrom is used as an effective component and is made into a pharmaceutical preparation by combining with known pharmaceutical carriers, it is now possible to prepare an antiviral agent. Manufacture of the antiviral agent may be conducted by the same manner as in the case of the above-mentioned anticancer agent and can be administered by the same manner as in the case of the above-mentioned drugs.

The dose as the antiviral agent is not particularly specified but may be appropriately determined depending upon the dosage form, administration method, purpose of the use and age, body weight, conditions, etc. of the patient. Usually, however, the amount of at least one of the compound selected from the compound of the present invention, an optically active substance thereof or a salt thereof contained in the preparation for an adult is $0.1\mu g$-20 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well. Furthermore, the compound of the present invention, an optically active substance thereof or a salt thereof may be used as a material for the antiviral food and beverage.

The compound of the present invention, an optically active substance thereof or a salt thereof has antiviral activity against DNA virus, RNA virus, retrovirus and viroid.

Accordingly, it may be used as antiviral agent for human being, antiviral agent for non-human animals such as that effective to viral diseases (e.g. for domestic animals, domestic fowls and cultured animals such as fish and shrimp), antiviral agent for plants such as that for viral diseases of agricultural and horticultural products (e.g. flowers and vegetables) and antiviral agent for useful animate things.

Examples of DNA virus infecting the animals are pox virus, herpes virus, adenovirus, hepatitis B virus, papilloma virus, polyoma virus, Epstein-Barr virus and baculovirus while an example of DNA virus infecting the plants is cauliflower mosaic virus. Examples of RNA virus infecting the animals are rotavirus, rubella virus, Japanese encephalitis virus, dengue virus, Newcastle disease virus, measles virus, mumpus virus, distemper virus, influenza virus, vesicular stomatitis virus, human poliomyelitis virus, hepatitis A virus and hepatitis C virus while examples of RNA virus infecting the plants are tobacco mosaic virus, wheat dwarf virus, rice stripe virus and tobacco ringspot virus. Examples of retrovirus are adult T cell leukemia virus and human acquired immunodeficiency syndrome virus and an example of virus is potato spindle tuber viroid.

The compound of the present invention, an optically active substance thereof or a salt thereof is effective for therapy and prevention of viral diseases of non-human mammals and birds such as chicken and turkey and cold-blooded animals such as fish and such a compound has an antiviral activity to the following non-human viruses. They are sciruid herpesvirus of type 1, cavlid herpesvirus of type 1, lagomorph herpesvirus of type 1, phasianid herpesvirus of type 1, phasianid herpesvirus of type 2, turkey herpesvirus of type 1, anatid herpesvirus of type 1, catfish herpesvirus of type 1, equid herpesvirus of type 3, bovid herpesvirus of type 1, bovid herpesvirus of type 3, bovid herpesvirus of type 4, porcine herpesvirus of type 1, porcine herpesvirus of type 2, murid herpesvirus of type 1, cebid herpesvirus of type 1, cebid herpesvirus of type 2, tupalid herpesvirus of type 1, canine herpesvirus of type 1, feline herpesvirus of type 1, equid herpesvirus of type 1 and equid herpesvirus of type 2.

Viral diseases of birds such as Marek disease can be prevented and/or cured by the compound used in the present invention by the method known in veterinary or breeding such as that the antiviral agent of the present invention is injected to birds or added to feed or drinking water. Further, when the compound used in the present invention is directly added to pool, water tank, holding tank, or water, seawater, etc. in a breeding area or is mixed with the feed, the following diseases can be similarly prevented and/or cured. They are viral diseases of fish living in a narrow sector such as pool, water tank, holding tank or breeding area infected with herpesvirus such as petite catfish virus, herpesvirus solomons and nerka virus and their examples are infectious necrotizing disease of hematopoietic organs, infectious diseases of herpesvirus or infectious necrotizing disease of pancreas of fish of salmon family, viral hemorrhagic septicemia of rainbow trout, spring viremia of carps, lymphocystis of various fish, viral necrotizing disease of erythrocytes of sea fish and anadromous fish, rhabdoviral disease of flatfish and the like, viral necrotizing disease of pancreas and liver of fry of yellowtail and the like, snout ulcer of torafugu (a kind of glovefish), etc. Incidentally, the precise regulation in administering the compound used in the present invention and the antiviral agent of the present invention is naturally dependent upon the necessity for each animals to be treated, type of the treatment and judgement of the breeder.

The non-human animals to which the antiviral agent of the present invention is administered are able to maintain their health whereby the improvement in survival rate, growing rate, spawning rate, etc. is significant.

The compound of the present invention, an optically active substance thereof or a salt thereof used in the present invention inhibits the synthesis of those viral proteins and inhibits the synthesis of virus genome as well and, accordingly, it exhibits a powerful antiviral action. In addition, it selectively kills the cells infected by those viruses.

For example, even in the patients suffering from human immunodeficiency virus (hereinafter, abbreviated as HIV), all of the (CD4-positive cells are not infected by HIV but only a part of them are infected by it. The antiviral agent of the present invention inhibits the production of HIV in those infected cells, at the same time, selectively kills the infected cells, and induces the resisting ability to virus to the uninfected cells whereby it is possible to remove the HIV/ from the cells.

The compound of the present invention, an optically active substance thereof or a salt thereof has an ability of improving the hepatic function and an induction activity of the heat shock protein. An agent for improving the hepatic function and an agent for inducing the heat shock protein containing at least one compound selected from the compound of the present invention, an optically active substance thereof or a salt thereof can be made into a pharmaceutical preparation by the same manner as in the case of the above-mentioned antiviral agent and can be administered by the same manner as in the case of the antiviral agent.

The dose as the agent for improving the hepatic function and for inducing the heat shock protein is not particularly specified but may be appropriately determined depending upon the dosage form, administration method, purpose of the use and age, body weight, conditions, etc. of the patient. Usually, however, the amount of at least one of the compound selected from the compound of the present invention, an optically active substance thereof or a salt thereof contained in the preparation for an adult is 0.1 µg-20 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well. Further, at least one of the compound selected from the compound of the present invention, an optically active substance thereof or a salt thereof may be used as a material for the food or beverage for improving the hepatic function or for inducing the heat shock protein.

When the compound of the present invention, an optically active substance thereof or a salt thereof is taken, disorder in hepatic function is improved and GOT and GPT values become normal.

Moreover, the compound of the present invention, an optically active substance thereof or a salt thereof has an induction activity of heat shock protein 70 kDa (HSP70), etc. and has an antiviral activity to RNA virus and DNA virus such as hepatitis virus, AIDS virus, influenza virus, vesicular stomatitis virus and herpesvirus. Heat shock protein participates in cancer immunity and those compounds are effective to cancer immunity as well. Further, the compounds has biodefense activity such as anti-inflammation activity. When the compound of the present invention, an optically active substance thereof or a salt thereof is taken, viral diseases such as cold by influenza can be prevented and cured.

Incidentally, heat shock protein is a general name for the protein whose synthesis is induced when cell or individual is subjected to a sudden temperature change which is higher than normal temperature to an extent of around 5–10° C. and it widely exists in prokaryotes and high eukaryotes. Examples of known heat shock protein are HSP90, HSP70, ubiquitin and HSP26. Among them, JISP70 is a kind of molecular chaperone and is bonded to protein where folding is not completed or is incompletely done to assist the formation of stereostructure. Amino acid sequence of the heat shock protein has been well conserved during the course of evolution and HSP70 is identical with DnaK protein of *Escherichia coli*. In human being, there are about ten HSP70 genes and some of them are expressed constitutionally while other are induced by various stimulations. Besides the heat shock, synthesis of heat shock protein is induced by various chemical substances and by cellular hindrance such as oxidation.

C. Amici, et al. reported [Journal of Virology, volume 68, pages 6890–6899 (1994)] that, when animal cells infected with Sendai virus are incubated in the presence of prostaglandin Al having α, β-unsaturated carbonyl group, synthesis of HSP70 and HS?90 is induced and that, during the synthesis of HSP70 is induced, synthesis of virus protein is inhibited. Further, A. Rossi, et al. reported [The Journal of Biological Chemistry, volume 271, pages 32192–32196 (1996)] that, like in the case of prostaglandin Al, 2-cyclopenten-1-one induces the synthesis of HSP70 and inhibits the synthesis of vesicular stomatitis virus protein.

An ability of the compound of the present invention for inducing HSP70 is noted at 10 µM and becomes maximum at 20–30 µM and this can be said to be a very high inducing ability as compared with the fact that a concentration of several hundred µM is required for 2-cyclopenten-1-one for inducing the HSP70.

Since the compound of the present invention, an optically active substance thereof or a salt thereof has such a high inducing ability to heat shock protein, it has antiviral activity to DNA virus, RNA virus, retrovirus and viroid. Examples of such virus and viroid are those which were mentioned hereinabove.

In addition, the compound of the present invention, an optically active substance thereof or a salt thereof has an inhibition activity of the growth of cancer cells which are transformed by cancer gene and has an activity of preventing the carcinogenesis due to cancer gene. or example, papilloma virus is a DNA virus belonging to family Papovaviridae and genus Papillomavirus and, with respect to human papilloma virus (HPV), HPV of type 16 which is a cause of cervical cancer has been known for example. The compound of the present invention, an optically active substance thereof or a salt thereof has an inhibition activity to the growth of cells which are cancerated by cancer gene E7 of an HPV16 type. Thus, an inhibiting agent to the growth of cancer cells which are cancerated by virus can be offered by the use of at least one compound selected from the compound of the present invention, an optically active substance thereof or a salt thereof as an effective component whereby canceration by cancer gene can be prevented.

Incidentally, the compound of the present invention, an optically active substance thereof or a salt thereof has an inhibit-on activity to carcinogenesis in two steps as an initiator and a promoter and it is now possible to offer an inhibiting agent to chemical canceration containing at least one compound selected from the above compound as an effective component.

Accordingly, it is possible to offer food or beverage for prevention of carcinogenesis containing at lest one compound selected from the compound of the present invention, an optically active substance thereof or a salt thereof.

The compound of the present invention, an optically active substance thereof or a salt thereof has an inhibition activity of IgE production and of a delayed type hypersensitivity and, when at least one compound selected from the above compound is used as an effective component and made into a pharmaceutical preparation combining with known pharmaceutical carriers, an antiallergic agent can be manufactured. Manufacture of said preparation can be conducted by the same manner as in the case of the above-mentioned anticancer agent. Incidentally, the antiallergic agent of the present invention can be administered by an appropriate route depending upon the dosage form. There will be no particular limitation for the administering route and may be conducted by oral or external means or by injection. For example, tablets, pills, granules, diluted powder, liquid, suspension, syrup and capsules may be orally administered. Injection may be administered, for example, intravenously, intramuscularly, subcutaneously or intracutaneously. Ointment, cream, etc. may be administered percutaneously. Suppositories may be administered per rectum. It is also possible to prepare aqueous or non-aqueous eye drops and examples of the eye drops to be administered to eye are ophthalmic ointment, painting liquid, sprinkling preparation and inserting preparation. For inhalation, a solution or a suspension of the effective component in common pharmaceutical vehicles is used and is applied, for example, as an aerosol spray for inhalation. It is also possible that dry and powdery effective component is administered using an inhaling device or the like so that the component can directly contact the lung.

The dose as an antiallergic agent is not particularly specified but may be appropriately determined depending upon the dosage form, administration method, purpose of the use and age, body weight, conditions, etc. of the patient. Usually, however, the amount of at least one of the compound selected from the compound of the present invention, an optically active substance thereof or a salt thereof contained in the preparation for an adult is 10 pg-50 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

An agent for inhibiting the IgE production and the delayed type hypersensitivity containing at least one compound selected from the compound of the present invention, an optically active substance thereof or a salt thereof as an effective component can be Trade into a pharmaceutical preparation by the same manner as in the case of the above-mentioned antiallergic agent and can be administered by the same manner as in the case of the antiallergic agent.

Further, the compound of the present invention, an optically active substance thereof or a salt thereof may be used as a material for the antiallergic food or beverage. When the compound of the present invention, an optically active substance thereof or a salt thereof is taken, symptoms of the diseases caused by IgE production and delayed type hypersensitivity can be significantly improved and, in addition, said compound has an excellent preventive activity to said diseases as well.

The antiallergic agent of the present invention inhibits the IgE production and is very useful for improvement and/or therapy of the diseases which is mediated or worsened by the IgE production such as allergic diseases caused by IgE including bronchial asthma, allergic rhitinis, atopic dermatitis, allergic conjunctivitis, urticaria and anaphylactic shock. It also inhibits the delayed type hypersensitivity and is useful for therapy and prevention of the diseases accompanied by a delayed type hypersensitivity such as contact sensitivity, allergic contact dermatitis, bacterial allergy, fungal allergy, viral allergy, drug allergy, thyroiditis and allergic encephalitis.

The compound of the present invention, an optically active substance thereof or a salt thereof has physiological activities such as anticancer activity, activity of inhibiting the growth of cancer cells, activity of inducing the apoptosis, activity of inhibiting the topoisomerase II, activity of inducing the differentiation of cancer cells, antirheumatic activity, activity of inhibiting the chronic articular rheumatism, activity of inducing the Fas antigen production, antibacterial activity, antiviral activity, activity of improving the hepatic function, activity of inducing the heat shock protein, activity of normalizing the blood components, activity of potentiating the cancer immune, anti-inflammatory activity, activity of inhibiting the tumor necrosis factor production, activity of inhibiting the nitrogen monoxide production, immunomodulating activity such as activity for inhibiting the delayed type hypersensitivity, activity for inhibiting lymphocyte transformation, activity of inhibiting the mixed lymphocyte reaction, activity of inhibiting the IgE production and activity of inhibiting the carrageenan edema and, as a result of those activities, food or beverage containing at least one compounds selected from the compound of the present invention, an optically active substance thereof or a salt thereof is useful as a functional food or functional beverage having the above-mentioned various physiological activities.

Incidentally, in the manufacture of food or beverage of the present invention, it is possible to use a heat treated product containing the cyclopentenone or partially purified cyclopentenone or purified cyclopentenone from said heat treated product and a compound containing an SH group and the compound of the present invention which is produced during the manufacturing steps can be used.

Thus, food or beverage in which at least one compound selected from the compound of the present invention (which is a reaction product of a material selected from the cyclopentenone-containing heat treated product and partially purified cyclopentenone and purified cyclopentenone from the heat treated product with a compound containing an SH group), an optically active substance thereof or a salt thereof is contained therein, diluted therein and/or added thereto is covered by the food or beverage of the present invention.

There is no particular limitation for the method of manufacturing the food and beverage of the present invention but cooking, processing and commonly-used manufacturing methods for food and beverage may be applied provided that an effective amount of at least one compound selected from the compound of the present invention, an optically active substance thereof or a salt thereof is contained in the resulting food or beverage.

In the manufacture of food or beverage, a heating treatment may be conducted during any of the steps whereby the cyclopentenone is contained in the heat treated product followed by reacting with a compound having an SH group or, alternatively, a heat-treated substance which contains the compound of the present invention may be added thereto. It is also possible that food, beverage or a material thereof is added to a heat-treated substance containing the compound of the present invention so that the compound of the present invention in said heat treated product may be diluted. The addition may be conducted either at one time or by dividing into several times. Thus, food or beverage having novel physiological activity can be manufactured easily and conveniently.

There is no particular limitation for the shape of the food or beverage of the present invention so far as at least one compound selected from the present invention, an optically active substance thereof or a salt thereof having physiological activities such as anticancer activity, antibacterial activity, apoptosis-inducing activity, antiviral activity and activity of improving the hepatic function is contained therein, added thereto and/or diluted therein. Thus, the shape includes the ones which can be orally taken such as tablets, granules, capsules, gel and sol.

The food or beverage of the present invention contains the compound of the present invention, an optically active substance thereof or a salt thereof having the physiological activities and, due to various physiological activities of said compound such as anticancer activity, antibacterial activity, apoptosis-inducing activity, antiviral activity and activity of improving the hepatic function, it is a healthy food or beverage having carcinogenesis-preventing and cancer-inhibiting effects and also a symptom-improving effect, preventing effect to the diseases showing sensitivity to compound of the present invention, an optically active substance thereof or a salt thereof such as viral diseases, diabetes mellitus, rheumatism, allergy and autoimmune diseases, or hepatic function improving effect and, further, it is food or beverage which is useful for maintaining the consistency of living body or particularly for keeping the health of stomach and utensil. In addition, due to its antibacterial activity, it is food or beverage having a very good preservation.

No toxicity was observed in the compound of the present invention, an optically active substance thereof or a salt thereof even when the dose which is effective to achieve those physiological activities is administered. In the case of oral administration for example, no dead case was observed in rats by a single oral administration of 1,000 mg/kg of any of the compounds represented by the formulae [VII], [VIII], [IX] and [X] as well as an optically active substances and a salt thereof.

As such, the compound of the present invention, an optically active substance thereof or a salt thereof is a very useful compoundinbroadareasof pharmaceuticals, food, beverage, etc. because of its various physiological functions. Such a compound of the present invention can be produced even in food or beverage as a reaction product of the cyclopentenone with a compound having an SH group such as SH-containing amino acid and derivatives thereof including cysteine-containing amino acid derivatives and the use of those compounds which are artificially produced as such is covered by the present invention as well.

EXAMPLES

The present invention will be further illustrated by way of the following examples although the present invention is never limited to those examples. Incidentally, "%" used in the examples stands for "% by weight".

Referential Example 1

D-Glucuroic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm$^2$ using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a Palpack type S column (manufactured by Takara Shuzo) and, when a detection was conducted by an ultraviolet absorption of 215 nm, the purity was found to be 98%.

The above cyclopentenone (113.9 mg) was dissolved in 2.85 ml of ethanol. To this ethanolic solution was added 3.85 ml of hexane/ethanol (94/6) to prepare a cyclopentenone solution (17 mg/ml). This was filtered through a filter of 0.5 μm to prepare a sample solution for an optical resolution HPLC.

This sample solution was applied to an optical resolution HPLC, each of the fractions of the (−)-cyclopentenone in the earlier peak and the (+)-cyclopentenone in the later peak was collected and evaporated to dryness in vacuo to give 43.2 mg of the (−)-cyclopentenone and 43.0 mg of the (+)-cyclopentenone.

Conditions for Optical Resolution HPLC.

Columns: Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 μl (2.55 mg)

Each of the (−)-cyclopentenone and (+)-cyclopentenone obtained herein contains about 1% of enantiomer and, therefore, they were subjected to an optical resolution under the above-mentioned conditions again. As a result, 19.7 mg of the (−)-cyclopentenone containing no enantiomer was obtained from 30.0 mg of the (−)-cyclopentenone of the earlier peak while, from 37.4 mg of the (+)-cyclopentenone of the later peak, 27.7 mg of the (+)-cyclopentenone containing no enantiomer was obtained. Incidentally, the eluting times in optical resolution HPLC of the (−)-cyclopentenone and (+)-cyclopentenone were 33 minutes and 40 minutes, respectively.

Example 1

(1) Aqueous solution (1M) (100 μl) of cyclopentenone and 100 μl of IM L-cysteine hydrochloride (manufactured by Nacalai Tesque; 103-13) adjusted to pH 4 with NaOH were mixed and made to react at 60° C. for 16 hours. The reaction mixture was filtered through a 0.5 μm Cosmo Nice Filter (manufactured by Nacalai Tesque; 440-84), the filtrate was applied to an HPLC using a Capsule Pack Column $C_{18}$ SG120 (6 mm×250 mm; manufactured by Shiseido) using 0.1% aqueous solution of trifluoroacetic acid (manufactured by Nacalai Tesque; 349-01) as a mobile phase at the flow rate of 0.5 ml/minute and a detection was conducted at absorbance of 210 nm whereupon main peaks were noted at 19.1 minutes and 19.5 minutes. They were fractionated and concentrated to dryness in vacuo to isolate two diastereomers, i.e. CM1 (19.1 minutes) and CM2 (19.5 minutes).

(2) Structure of the reaction product of cyclopentenone with L—cysteine

Mass analysis of CM1 and CM2 isolated in Example 1-(1) was conducted using a mass spectrometer DX302 (manufactured by Nippon Denshi). Further, they were dissolved in 0.1N solution of DCl in heavy water and their structures were analyzed by means of nucleomagnetic resonance (NMR). JNM-A500 (manufactured by Nippon Denshi) was used as a nucleomagnetic resonance device. Ultraviolet (UV) absorption spectrum was measured using a UV-2500 spectrophotomer (manufactured by Shimadzu). The results are as given below.

CM1

FAB-MS m/z 218 [M+H]+

Glycerol was used as a matrix.

$^1$H-NMR

δ 2.32 (1H, dd, J=20.0, 1.5 Hz, 5-H), 2.89 (1H, dd, J=20.0, 6.0 Hz, 5-H), 3.01 (1H, dd, J=15.0, 7.0 Hz, 1'-H), 3.09 (1H, dd, J=15.0, 4.5 Hz, 1'-H), 4.01 (1H, m, 4-H), 4.16 (1H, dc, J=7.0, 4.5 Hz, 2'-H), 6.49 (1H, d, J=3.0 Hz, 3-H).

UV: $\lambda_{max}$ nm 250 nm (water)

CM2

FAB-MS m/z 218 [M+H]+

Glycerol was used as a matrix.

$^1$H-NMR,

δ 2.31 (1H, dd, J=20.0, 1.5 Hz, 5-H), 2.87 (1H, dd, J=20.0, 6.0 Hz, 5-H), 3.01 (1H, dd, J=15.0, 6.5 Hz, 1'-H), 3.11 (1H, dd, J=15.0, 4.5 Hz, 1'-H), 4.00 (1H, m, 4-H), 4.20 (1H, dd, J=6.5, 4.5 Hz, 2'-H), 6.46 (1H, d, J=3.0 Hz, 3-H).

In the above, chemical shift values for $^1$H-NMR were expressed when that of HOD was defined as 4.65 ppm.

Further, CM1 was dissolved in 0.1N solution of DCl in heavy water and $^{13}$C-NMR was measured using JNM-A500.

$^{13}$C-NMR

δ 30.3 (11-C), 39.4 (4-C), 42.0 (5-C), 53.4 (2'-C) 132.8 (3-C), 154.6 (2-C), 171.1 (3'-C), 205.5 (1-C).

In the above, chemical shift values for $^{13}$C-NMR were expressed when that of dioxane was defined as 67.4 ppm.

Incidentally, the numbers of assignment of the peaks of $^1$H-NMR and $^{13}$C-NMR are as shown in the following formula [VII].

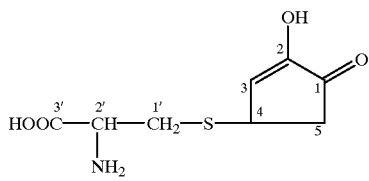

[VII]

Then infrared (IR) absorption spectrum of a mixture of CM1 and CM2 in equal amounts (hereinafter, referred to as CM) was measured by an infrared spectrophotometer (FTIR-8000PC; manufactured by Shimadzu). The result is as follows.

IR $v^{KBr}_{max}$ cm$^{-1}$ 3000, 1705, 1625, 1201.

Diffuse reflectance method was applied.

From those data, it was clarified that one of CM1 and CM2 had a structure of [VIII] while another has a structure of [IX].

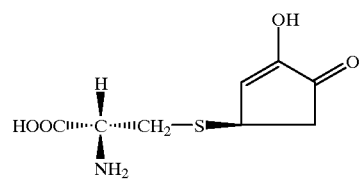

[VIII]

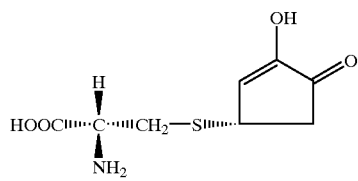

[IX]

Figure 2:
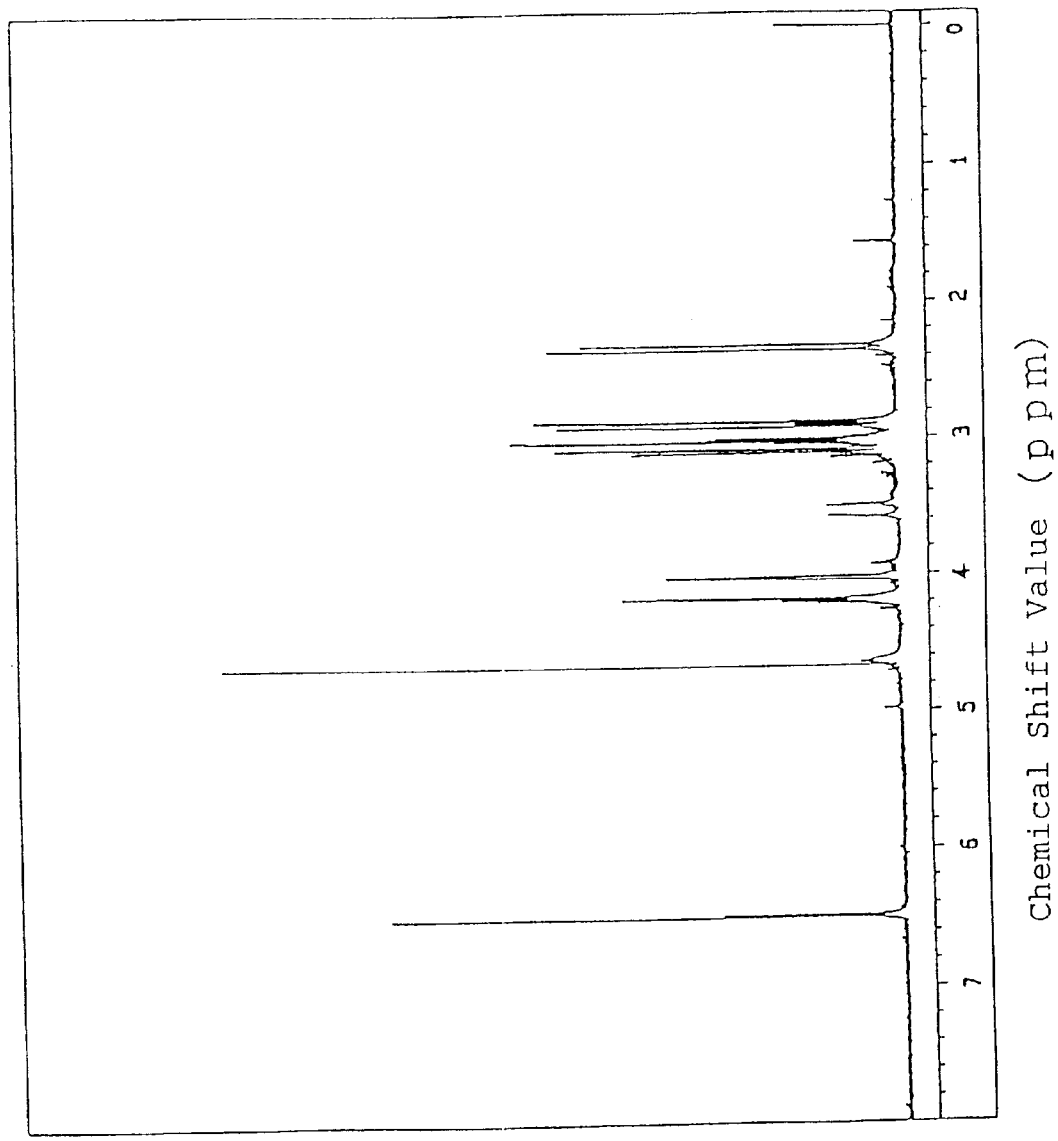
FIG. 2 shows a $^1$H-NMR spectrum of CM1.
Figure 3:
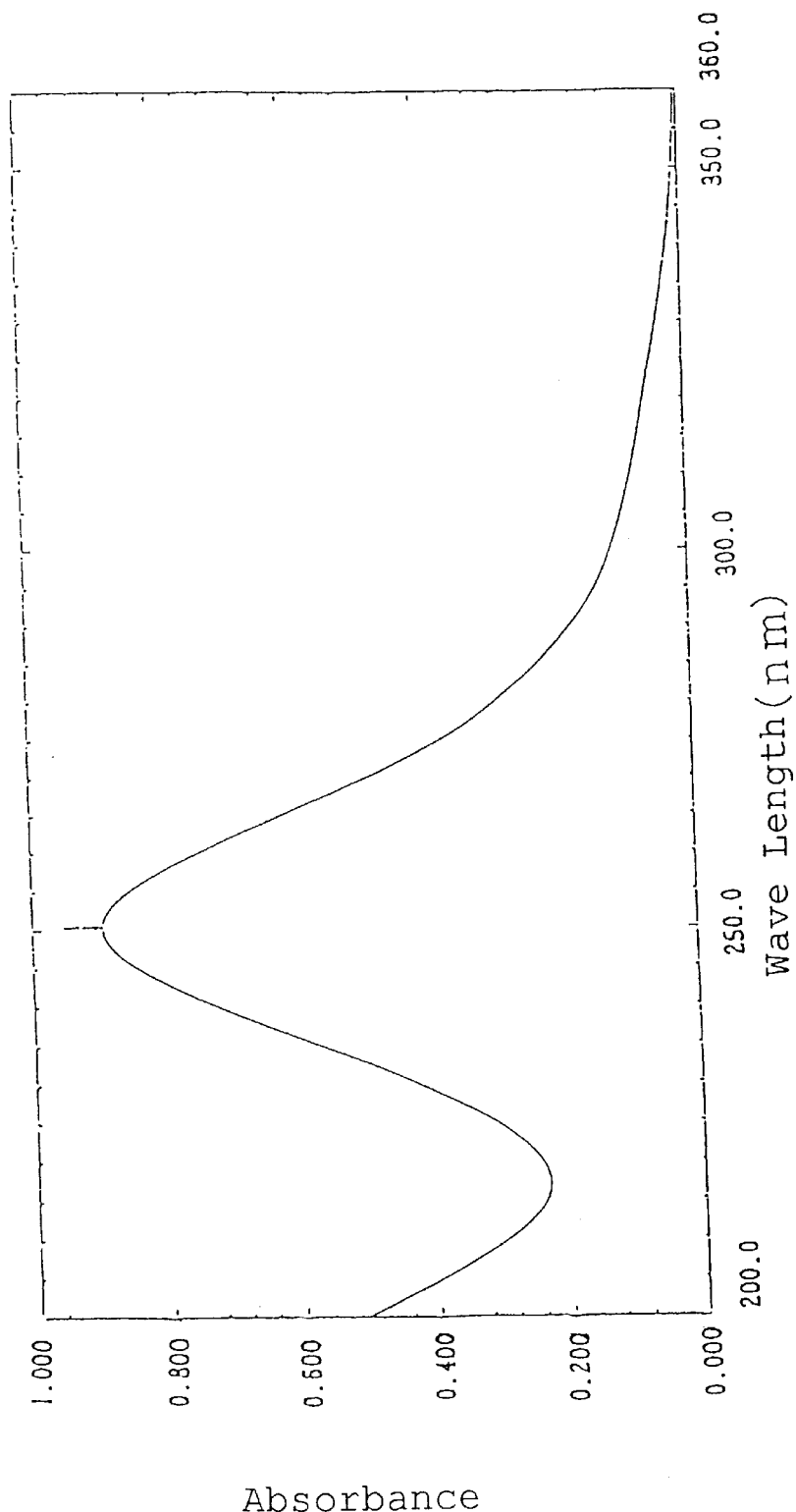
FIG. 3 shows a UV absorption spectrum of CM1.
Figure 4:
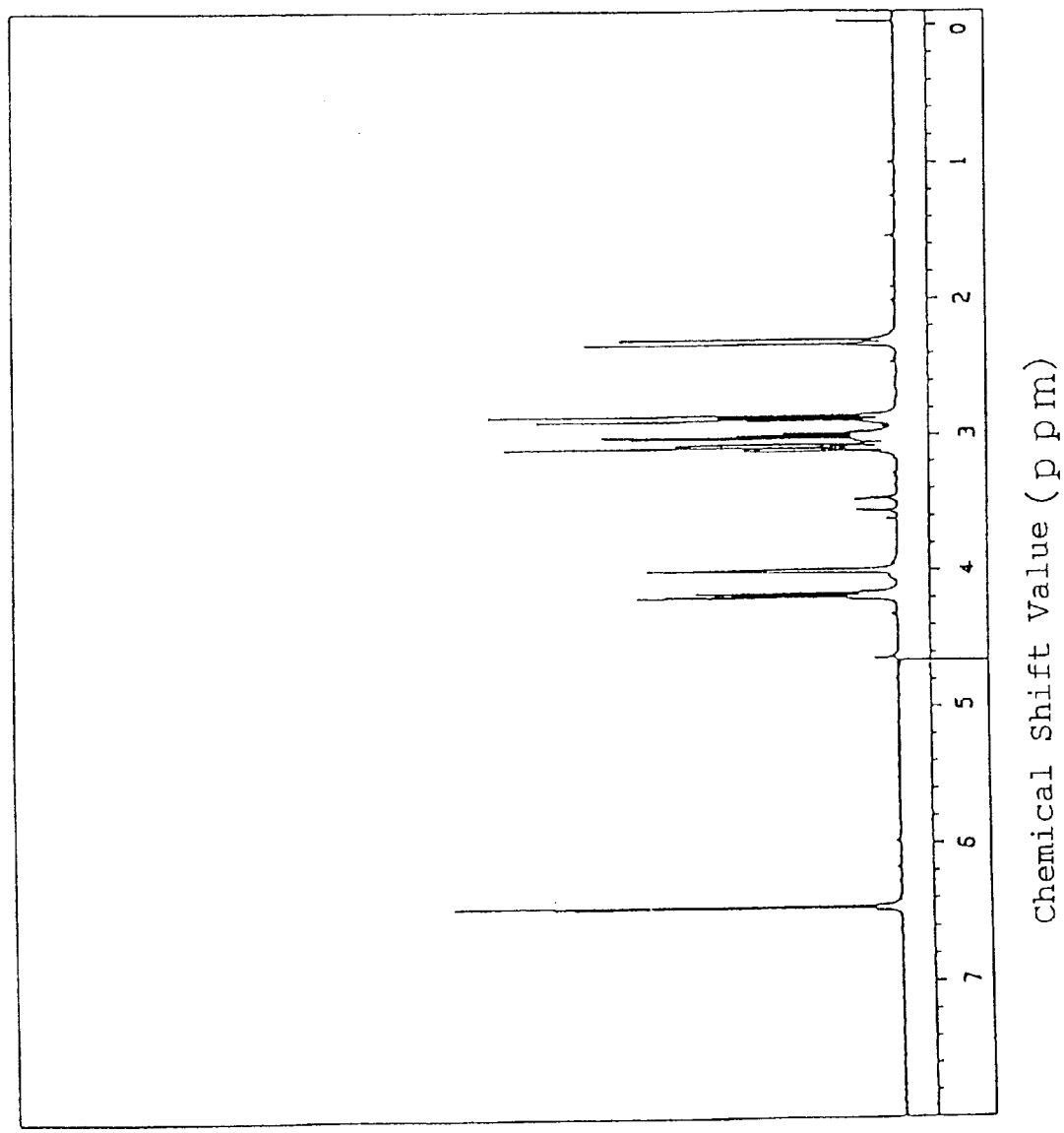
FIG. 4 shows a $^1$H-NMR spectrum of CM2.
Figure 5:
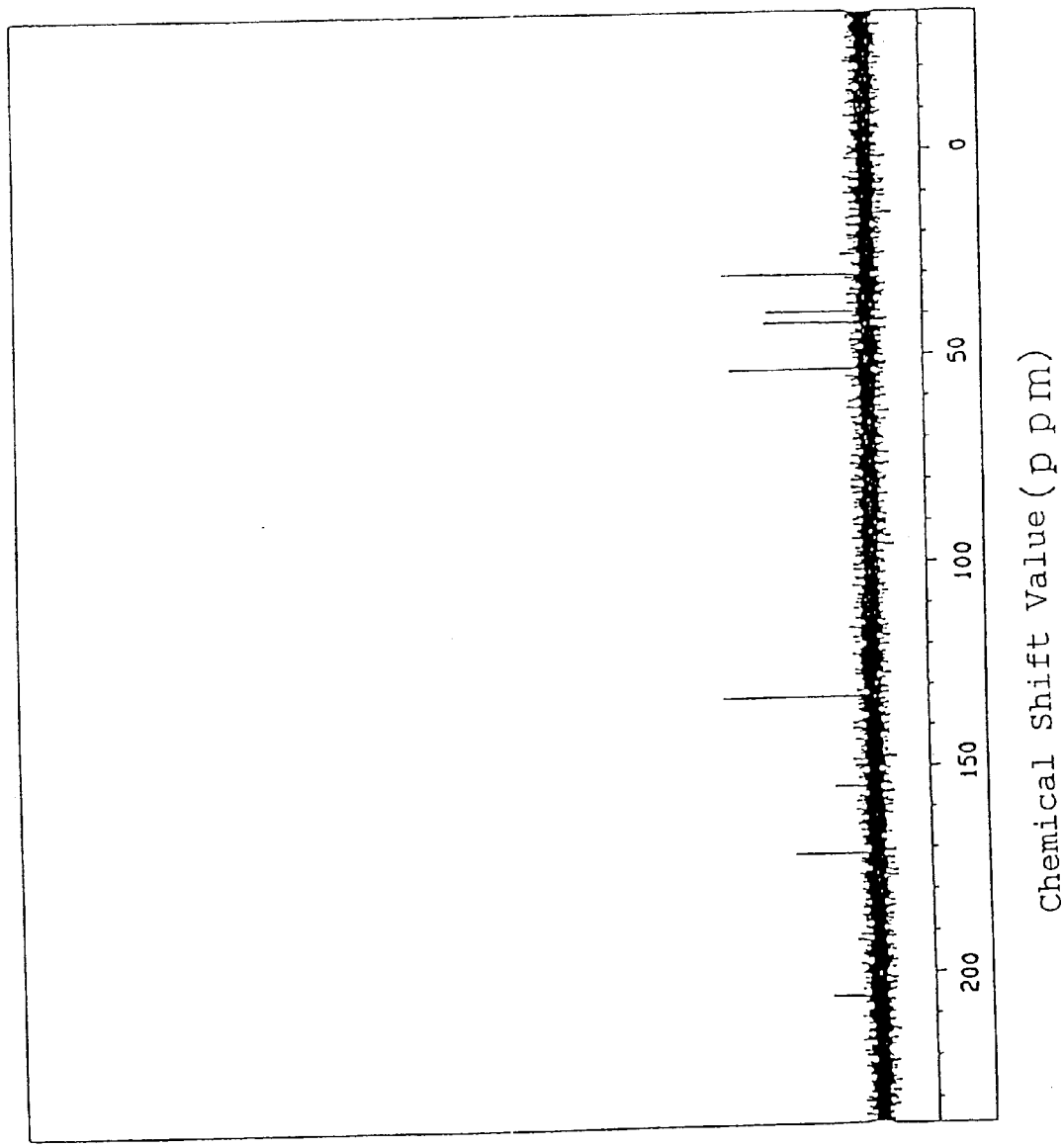
FIG. 5 shows a $^{13}$C-NMR spectrum of CM1.
Figure 6:
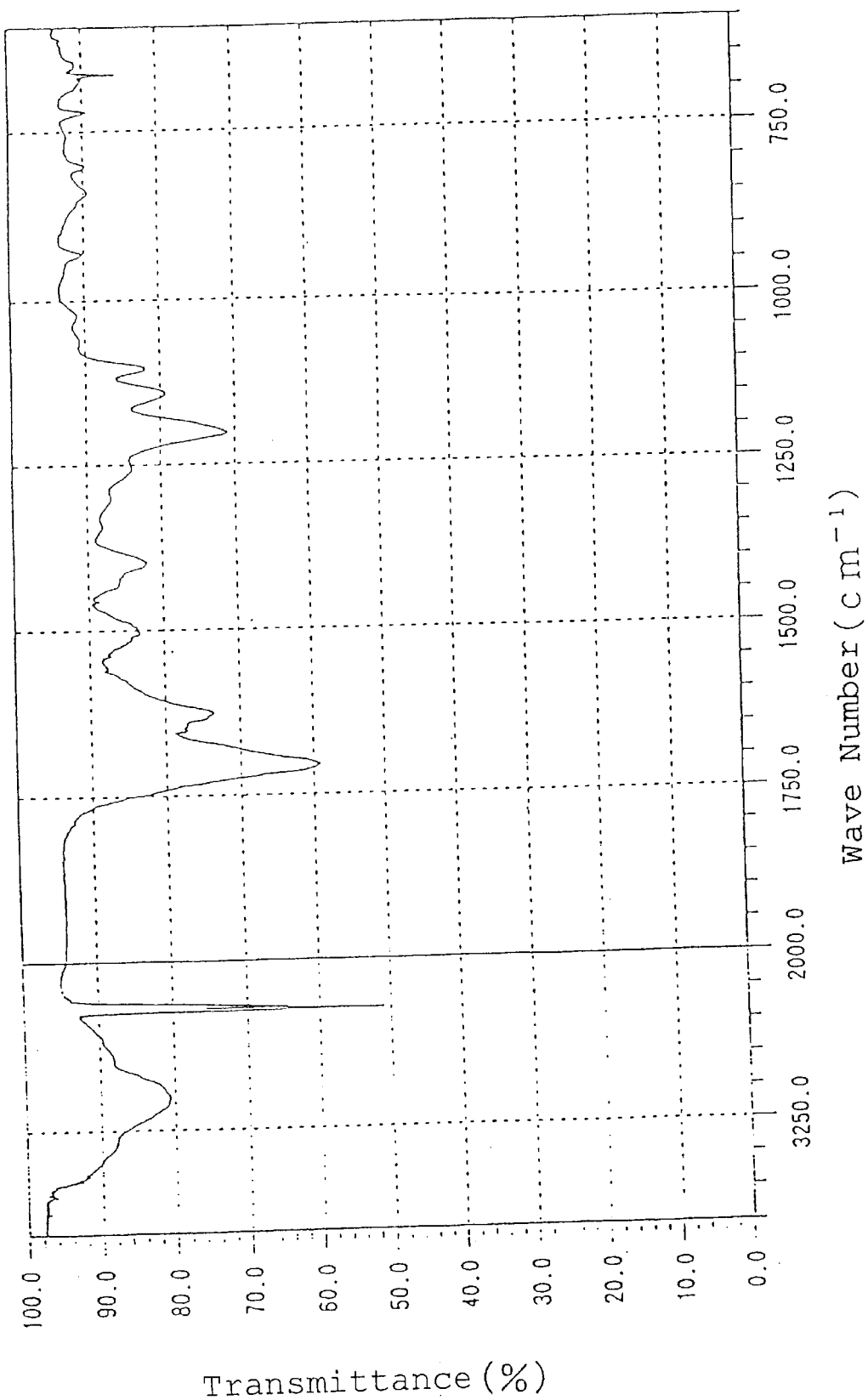
FIG. 6 shows an IR absorption spectrum of CM.

FIG. 1 shows mass spectrum of CM1; FIG. 2 shows $^1$H-NMPR spectrum of CM1; FIG. 3 shows UV absorption spectrum of CM1; FIG. 4 shows $^1$H-NMR spectrum of CM2; FIG. 5 shows $^{13}$C-NMR of CM1; and FIG. 6 shows IR absorption spectrum of CM. In FIG. 1, abscissa indicates m/z values while ordinate indicates relative intensity (%). In FIGS. 2, 4 and 5, abscissa indicates chemical shift value (ppm) while ordinate indicates intensity of the signal. In FIG. 3, abscissa indicates wave length (nm) while ordinate indicates absorbance. In FIG. 6, abscissa indicates wave number (cm$^{-1}$) while ordinate indicates transmittance.

Example 2

(1) Aqueous solution (1M) (100 μl) of the cyclopentenone and 500 μl of 200 mM aqueous solution of glutathione (reduced type; manufactured by Nacalai Tesque; 110-10) (pH 3.0 ) were mixed and made to react at 60° C. for five hours. The reaction solution was filtered through a 0.5 μm Cosmo Nice Filter and the filtrate was separated by means of an HPLC under the following condition.

Column: TSK gel ODS-80Ts (5 μm), 20 mm×25 cm
Mobile phase: A 0.1% aqueous solution of TFA
B 0.1% TFA/50% aqueous solution of acetonitrile
Flow rate: 7.5 ml/minute Gradient: mobile phase A for 10 minutes→from mobile phaseA to A:B=1:1 during 55 minutes→from A:B=1:1 to mobile phase B3 during 15 minutes
Detection: absorbance at 220 nm The above reaction solution (200 μl) was applied to an HPLC, peaks of retention times of 35.7 minutes and 36.1 minutes were collected and each of them was concentrated to dryness in vacuo to isolate two diastereomers, i.e. GM1 and GM2. Yield of GM1 was 2.5 mg while that of GM2 was 3.0 mg.

Figure 7:
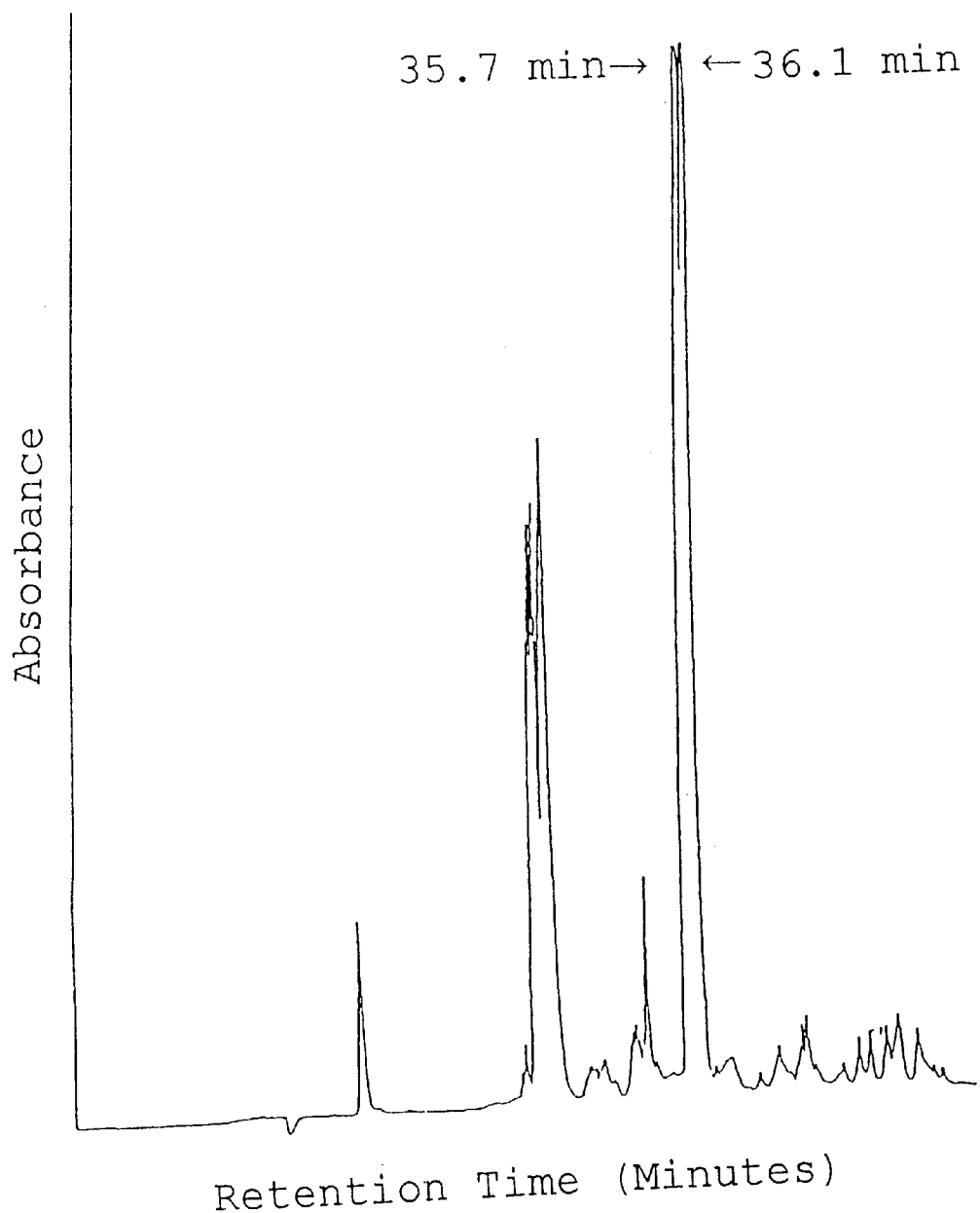
FIG. 7 shows a relation between retention time and absorbance.

FIG. 7 shows their chromatograms. Thus, FIG. 7 shows the relation between retention time and absorbance in which abscissa indicates retention time (minutes) while ordinate indicates absorbance at 220 nm.

(2) Structure of a mixture (hereinafter, referred to as GM) of same amounts of GM1 and GM2 prepared in Example 2-(1) was analyzed. Nuclear magnetic resonance (NMR) spectrum was measured by JNM-A500 (manufactured by Nippon Denshi); mass spectrum (MS) was measured by DX302 mass spectrometer (manufactured by Nippon Denshi); ultraviolet (UV) spectrum was measured by UV-2500 spectrophotometer (manufactured by Shimadzu); and infrared (IR) absorption spectrum was measured by FTIR-8000PC infrared spectrophotometer (manufactured by Shimadzu). The result is as follows.

$^1$H-NMR

δ 2.09 (2H, m, 5'-H), 2.28 (1H, dd, J=13.0, 20.0 Hz, 5-H), 2.44 (2H, m, 4'-H), 2.78 (1H, dd, J=8.5, 14.0 Hz, 1'-H), 2.85 or 2.89 (1H, dd, J=3.0, 6.0 Hz, 5-H), 2.92 or 2.95 (1H, dd, J=1.0, 5.5 Hz, 1'-H), 3.86 (2H, s, 9'-H), 3.95 (2H, m, 4-H, 6'-H), 4.46 (1H, m, 2'-H), 6.47 or 6.49 (1H, d, J=3.0 Hz, 3-H).

The sample was dissolved in 0.1N DCl solution in heavy water and chemical shift value of HOD was expressed as 4.65 ppm.

$^{13}$C-NMR

δ 26.3 (5'-C), 31.7 (4'-C), 31.9 or 32.1 (1'-C), 39.3 (4-C), 41.9 (9'-C), 42.2 or 42.3 (5-C), 53.3 (6'-C), 54.1 (2'-C), 133.5 (3-C), 154.4 (2-C), near 173 (3'-C, 7'-C, 8'-C, 10'-C), 205.8 (1-C).

The sample was dissolved in 0.1N DCl solution in heavy water and chemical shift value of dioxane was expressed as 67.4 ppm.

Incidentally, the assignment numbers for the peaks by $^1$H-NMR and $^{13}$C-NMR are as shown in the following formula [X].

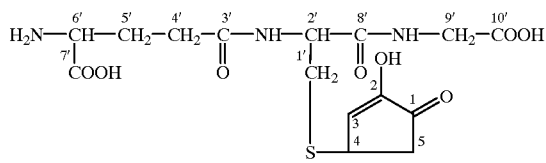

[X]

FAS-MS m/z 404 (M+H)$^+$, 426 (M+Na)$^+$

Glycerol was used as a matrix.

UV $\lambda_{max}$ 251 nm (water)

IR $\nu_{max}^{KBr}$ cm$^{-1}$ 2949, 1710, 1660, 1539, 1404, 1203

Diffuse reflectance method was used.

Figure 8:
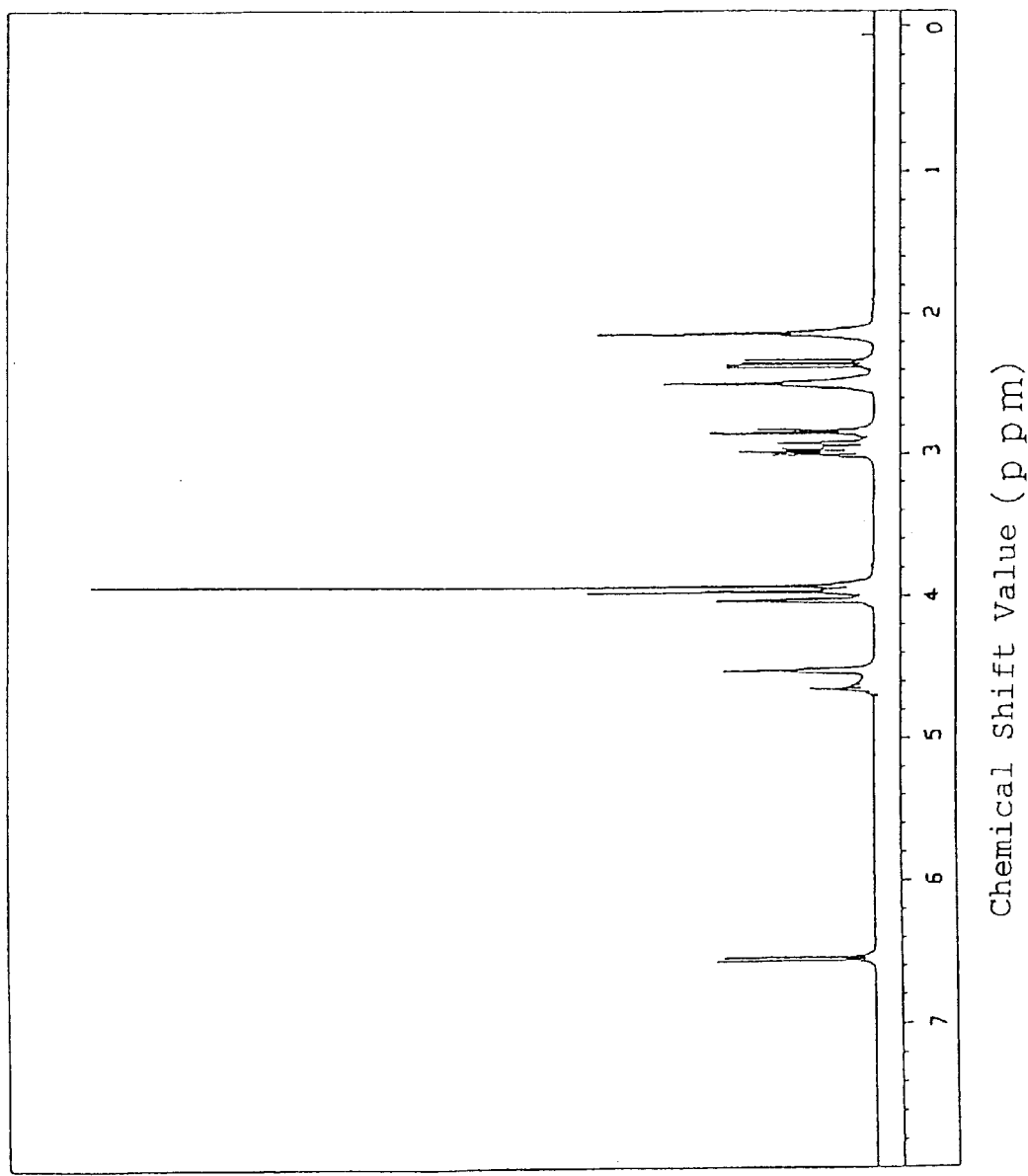
FIG. 8 shows a $^1$H-NMR spectrum of GM.
Figure 9:
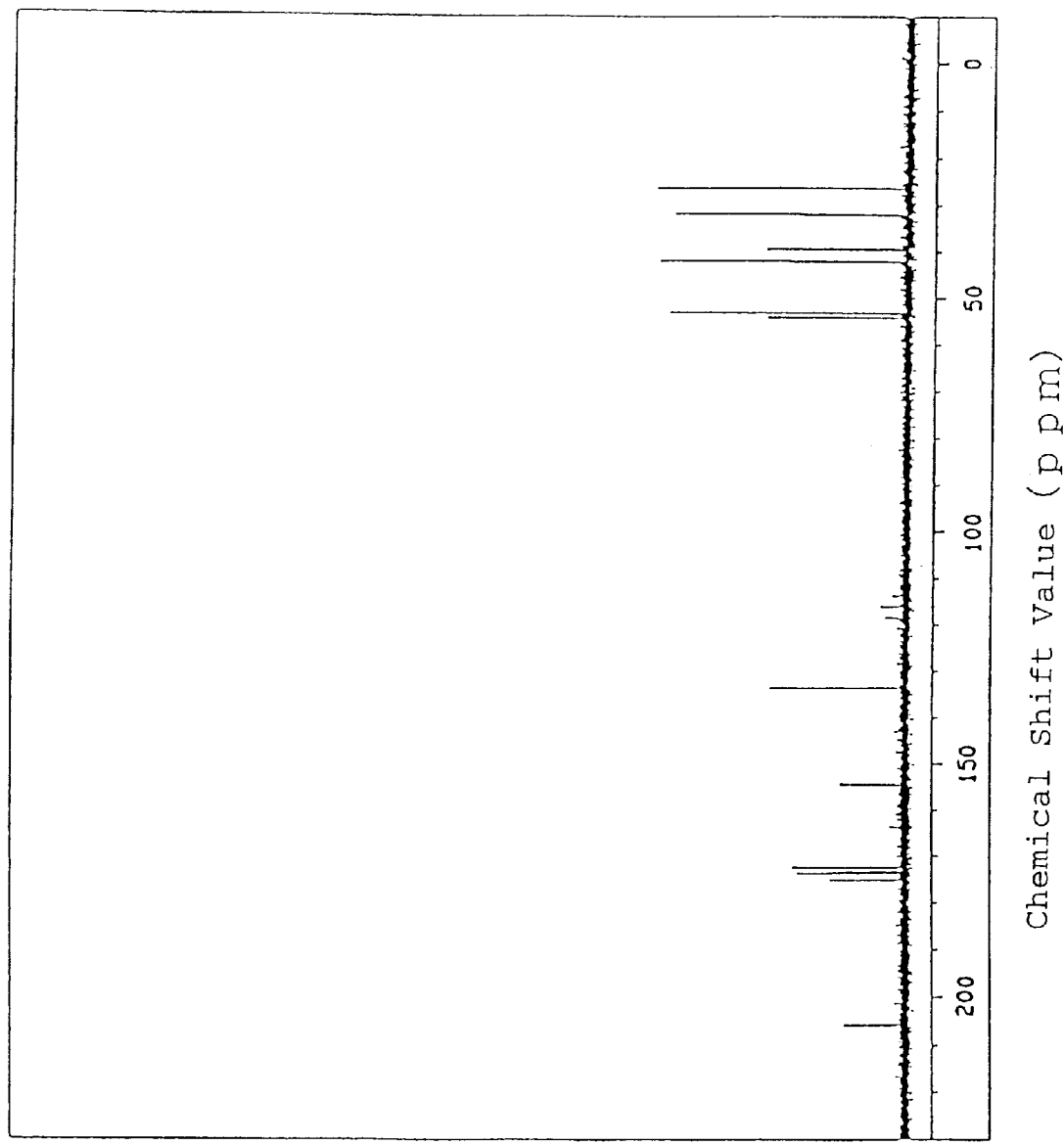
FIG. 9 shows a $^{13}$C-NMR spectrum of GM.
Figure 10:
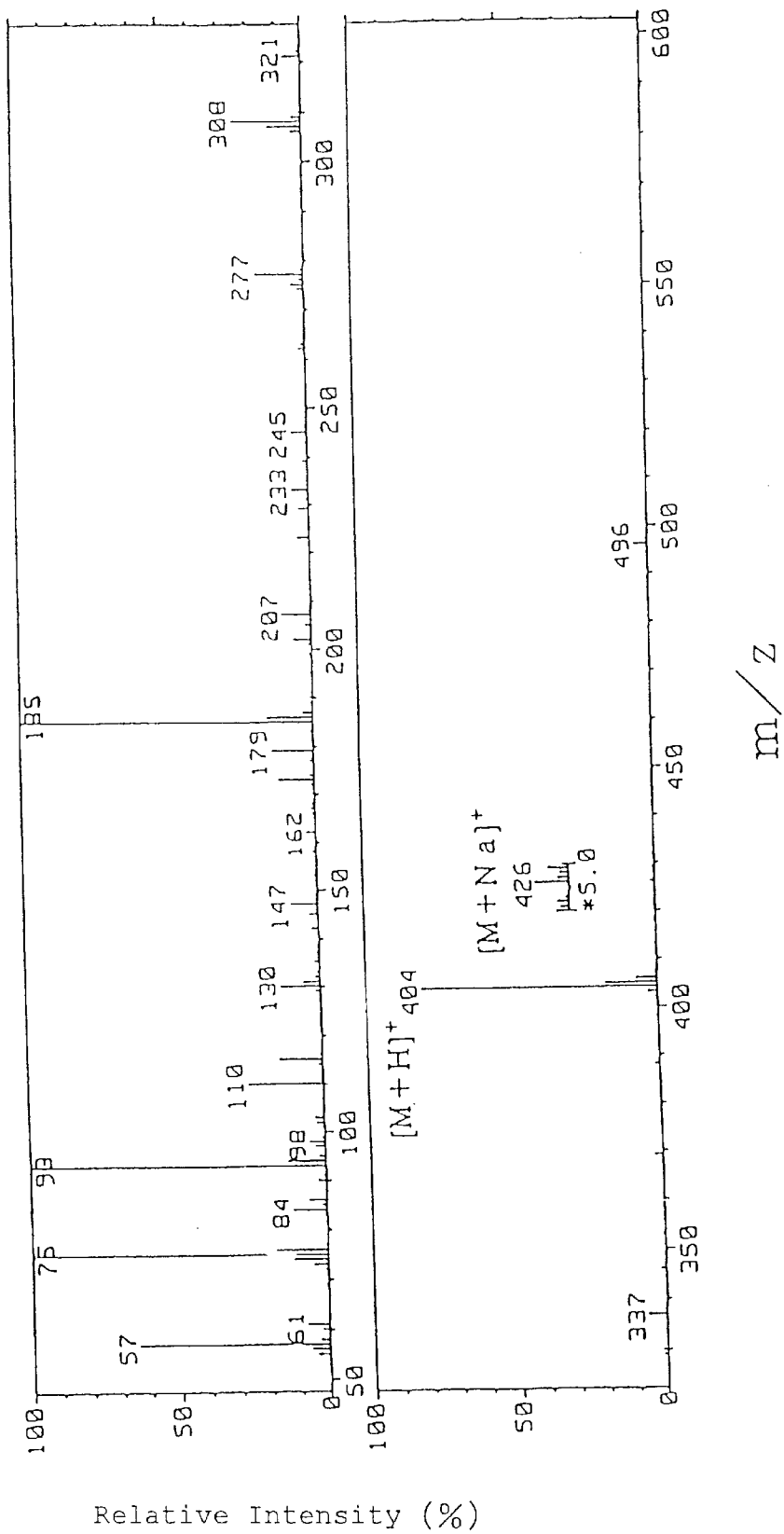
FIG. 10 shows a mass spectrum of GM.
Figure 11:
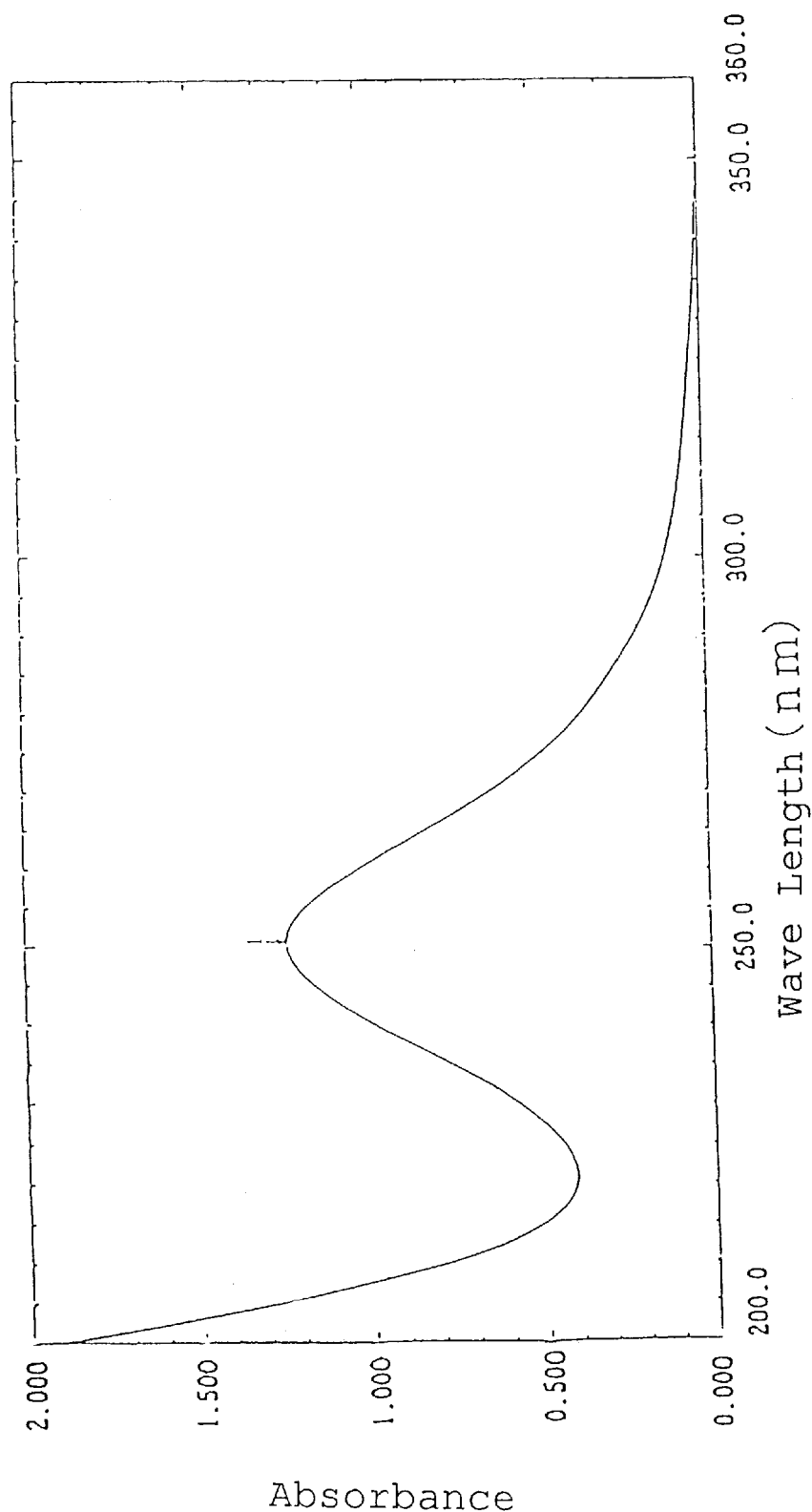
FIG. 11 shows a UV absorption spectrum of GM.
Figure 12:
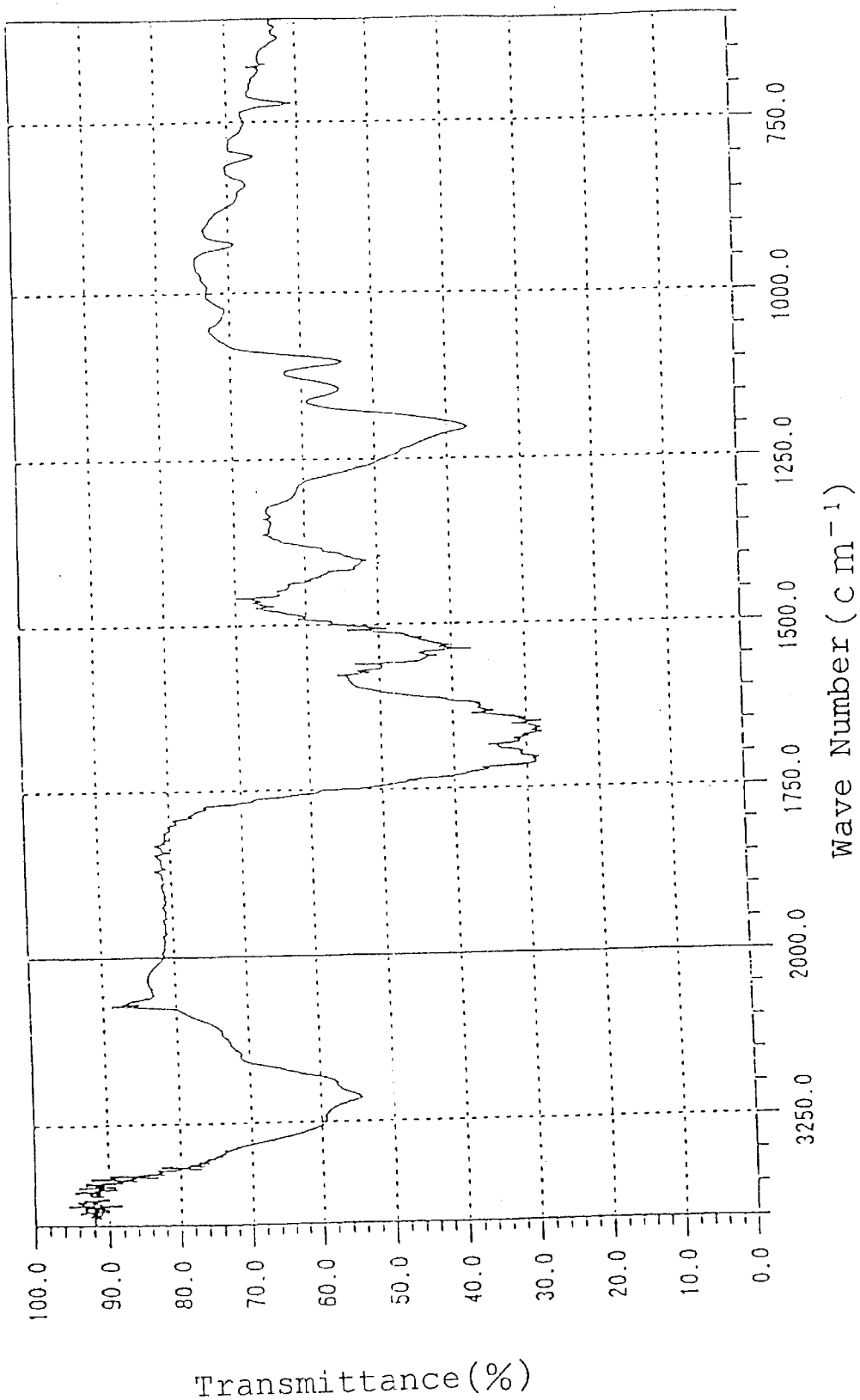
FIG. 12 shows an IR absorption spectrum of GM.
Figure 13:
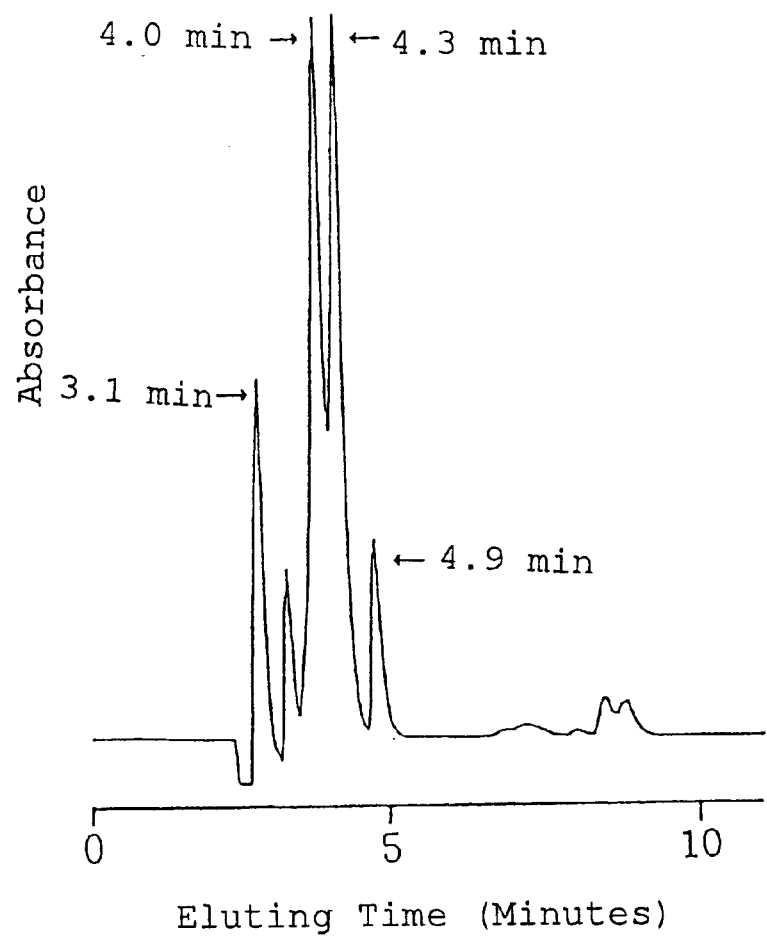
FIG. 13 shows an elution pattern of an example of the cyclopentanone thio derivatives.

The result is shown in FIGS. 8–12. FIG. 8 shows $^1$H-NMR spectrum of GM in which abscissa indicates chemical sift value (ppm) while ordinate indicates intensity of the signals; FIG. 9 shows $^{13}$C-NMR of GM in which abscissa indicates chemical sift value (ppm) while ordinate indicates intensity of the signals; FIG. 13 shows mass spectrum of GM in which abscissa indicates m/z value while ordinate indicates relative intensity (%); FIG. 11 shows UV spectrum of GM in which abscissa indicates wave length (nm) while ordinate indicates absorbance; and FIG. 12 shows IR absorption spectrum of GM in which abscissa indicates wave numbers (cm$^{-1}$) while ordinate indicates transmittance (%).

From the above result, it has been clear that GM1 and GM2 are diastereomers of 2-hydroxy-4-glutathion-S-yl-2-cyclopenten-1-one and that one of them has a structure as shown by [XI] while another has a structure as shown by [XII].

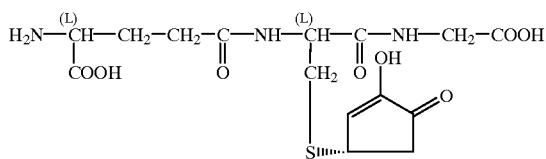

[XI]

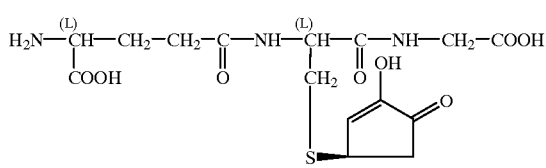

[XII]

Example 3

(1) Cyclopentenone and L-cysteine hydrochloride (manufactured by Nacalai Tesque; 103-13) were dissolved in a phosphate buffer saline solution (pH 7.2) to make concentration of each of them 10 mM followed by reacting at 37° C. for 30 minutes. The reaction mixture was filtered through a 0.5 μm Cosmo Nice Filter (manufactured by Nacalai Tesque; 440-84), the filtrate was applied to an HPLC using 0.1% aqueous solution of trifluoroacetic acid (manufactured by Nacalai Tesque; 349-01) as a mobile phase at a flow rate of 1 ml/minute using a TSK-Gel ODS 80 Ts (4.6 mm×250 mm; manufactured by Tosoh) and the detection was conducted by means of the absorbance at 210 nm whereupon peaks of cyclopentenone and L-cysteine decreased while main peaks at 4.0 minutes and 4. 3 minutes newly appeared.

The result is shown in FIG. 13. Thus, FIG. 13 shows the relation between eluting time and absorbance at 210 nm in which abscissa indicates eluting time (minutes) while ordinate indicates absorbance at 210 nm.

Incidentally, in FIG. 13, 3.1 minutes is an eluting position for L-cysteine while 4.9 minutes is that of cyclopentenone.

Figure 14:
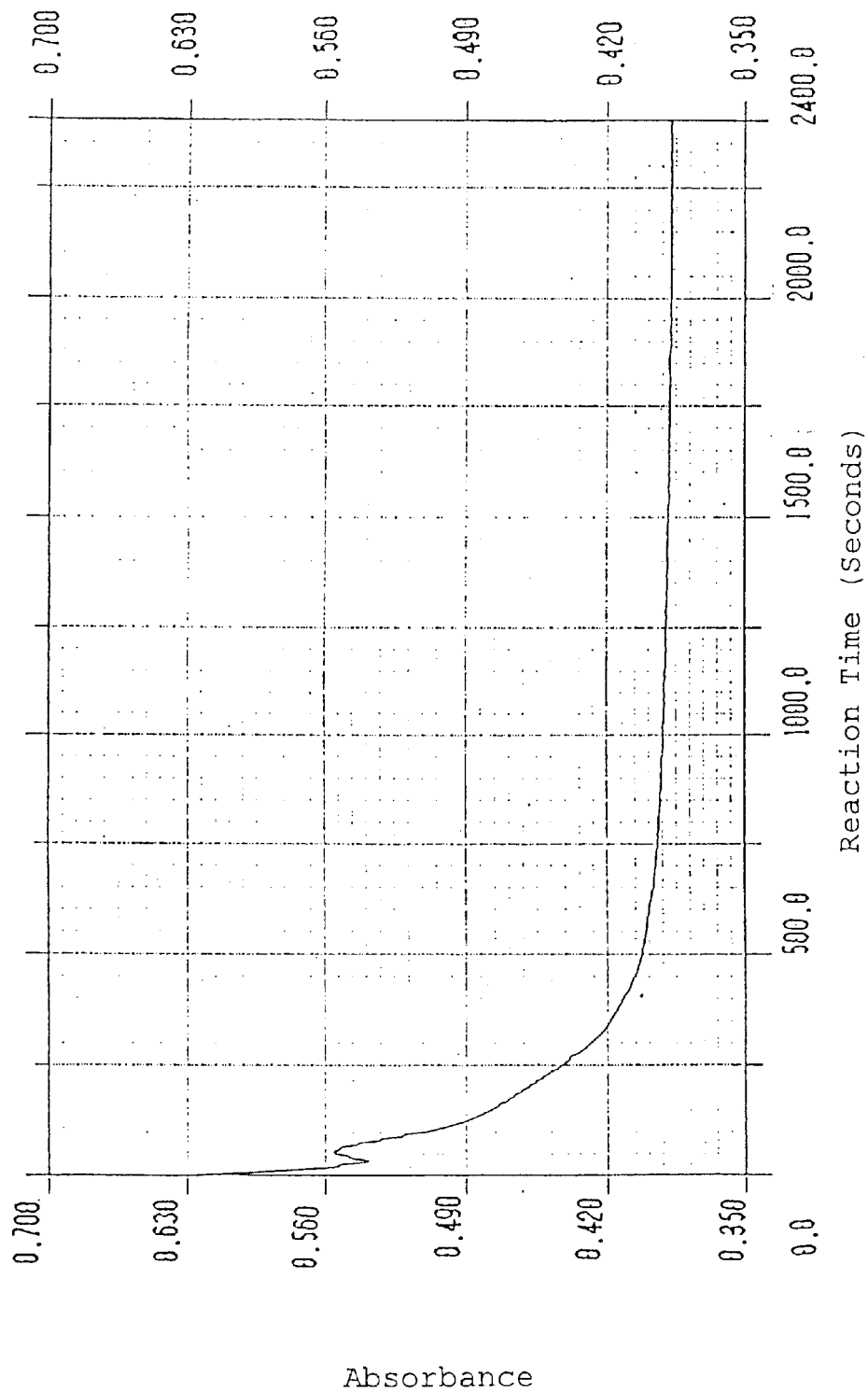
FIG. 14 shows a relation between the reaction time and the absorbance at 215 nm when L-cysteine is used.

(2) Cyclopentenone and L-cysteine hydrochloride were dissolved in a phosphate buffer saline solution (pH 7.2) to make the concentration of each of them 100 μM and the changes in absorbance at 215 nm at 37° C. with a lapse of time were measured by a UV-2200 spectrophotometer (manufactured by Shimadzu). As a result, the absorbance decreased with a lapse of reaction time and, after 500 seconds, it was nearly constant. The result is shown in FIG. 14. Thus, FIG. 14 shows the relation between the reaction time and absorbance at 215 nm using L-cysteine where abscissa indicates reaction time (seconds) while ordinate indicates absorbance at 215 nm.

Figure 15:
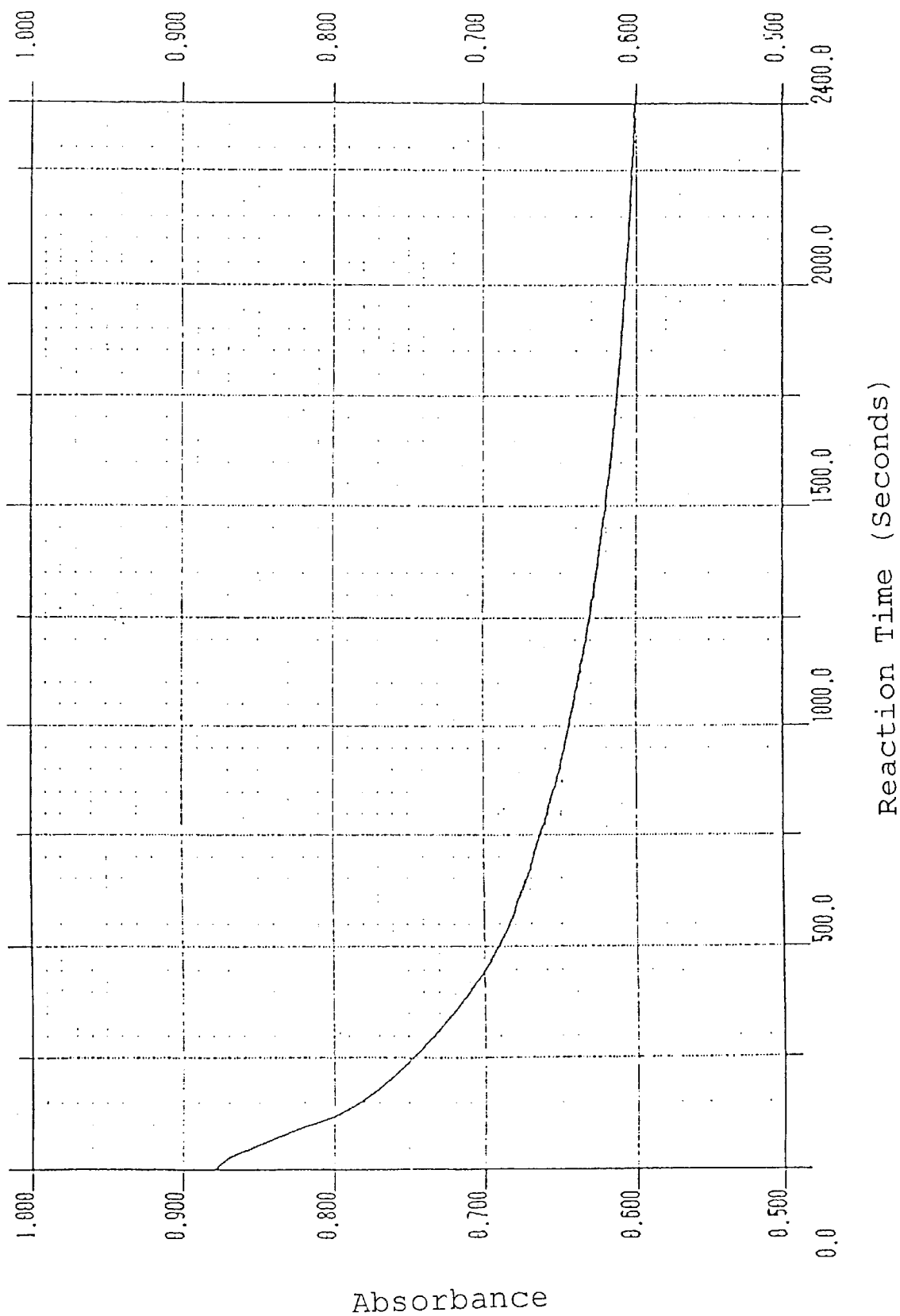
FIG. 15 shows a relation between the reaction time and the absorbance at 215 nm when glutathione is used.

When the same operation was conducted using glutathione (reduced type; sold by Nacalai Tesque; 170-10) instead of L-cysteine hydrochloride, the absorbance at 215 nm decreased with a lapse of the reaction time and, after 2,000 seconds, it was nearly constant. The result is shown in FIG. 15. Thus, FIG. 15 shows the relation between the reaction time and absorbance at 215 nm when glutathione was used where abscissa indicates reaction time (seconds) while ordinate indicates absorbance at 215 nm.

(3) Cyclopentenone and L-cysteine hydrochloride were dissolved in a phosphate buffer saline solution (pH 7.2) to make the concentration of each of them 10 mM and made to react at 37° C. for 30 minutes. The reaction mixture was filtered through a 0.5 μm Cosmo Nice Filter and the filtrate was applied to a high performance liquid chromatographic mass analysis using TSK-Gel ODS 80Ts (4.6 mm×250 mm; manufactured by Tosoh) and API 300 (manufactured by PE SCIEX) at the flow rate of 1 ml/minute using 0.1% aqueous solution of acetic acid as a mobile phase. The mass analysis was conducted in a positive ion mode. As a result, a signal of m/z=236.1 [M+H]$^+$was observed and the molecular weight of the substance which was newly produced by the reaction was 235.

Figure 16:
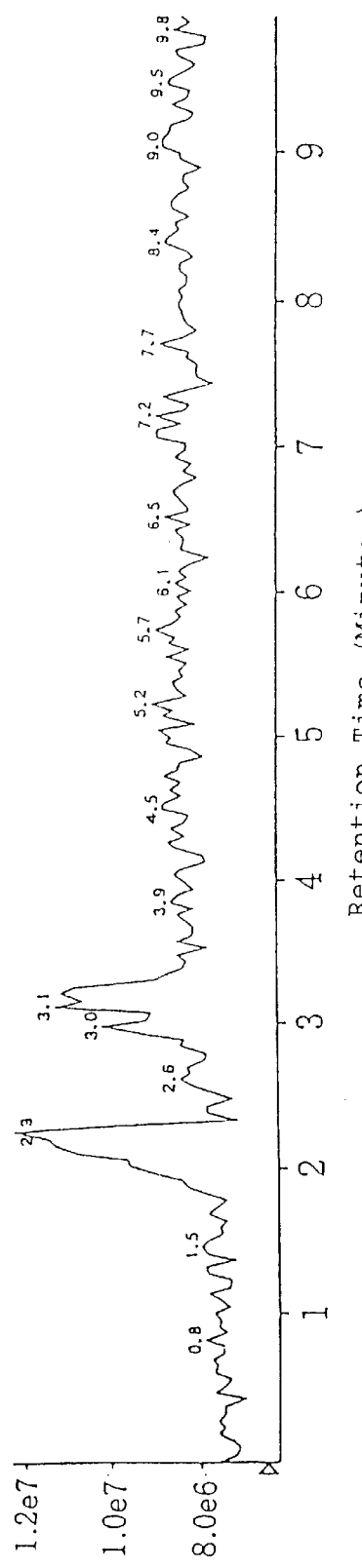
FIG. 16 shows a chromatogram of the reaction product in an example of the present invention.
Figure 17:
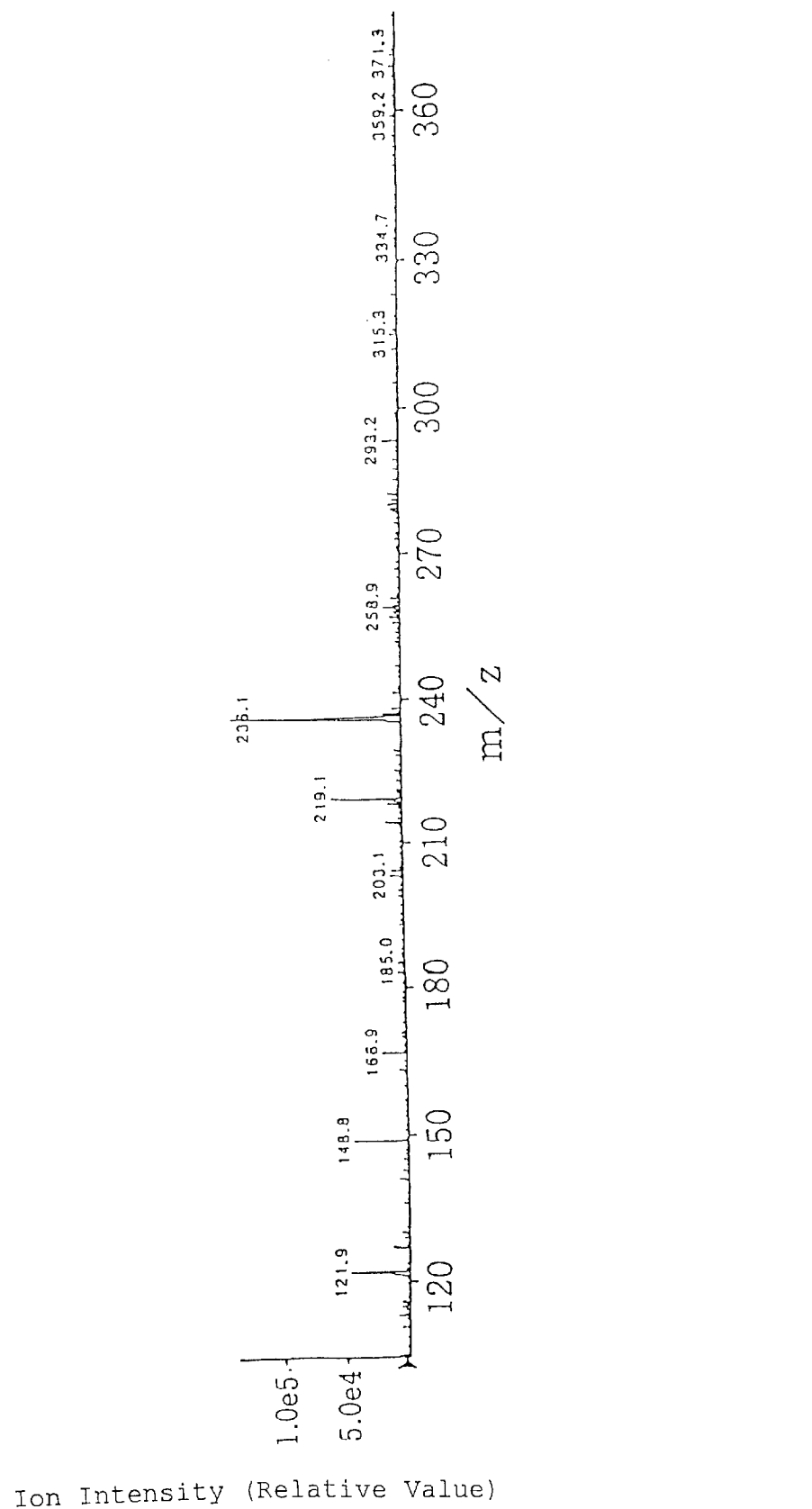
FIG. 17 shows a mass spectrum of a peak at 2.99 minutes in FIG. 4.

The result is shown in FIG. 16 and FIG. 17. Thus, FIG. 16 shows a chromatogram of the reaction product which is one of the examples of the present invention where abscissa indicates a retention time (minutes) while ordinate indicates total ion intensity (relative value). FIG. 17 shows a mass spectrum of the fraction eluted at 2.99 minutes in FIG. 16 where abscissa indicates m/z while ordinate indicates ion intensity (relative value). Incidentally, in the mass spectrum of the fractions eluted at 3.15 minutes and 3.24 minutes in FIG. 16, signal of m/z=236.1 [M+H]$^+$was observed as well.

(4) Cyclopentenone and L-cysteine hydrochloride were dissolved in a phosphate buffer saline solution (pH 7.2) to make the concentration of each of them 100 μM and made to react at 37° C. for 50 minutes. Ultraviolet absorption spectra before and after the reaction were measured by a UV-2200 spectrophotometer (manufactured by Shimadzu).

Figure 18:
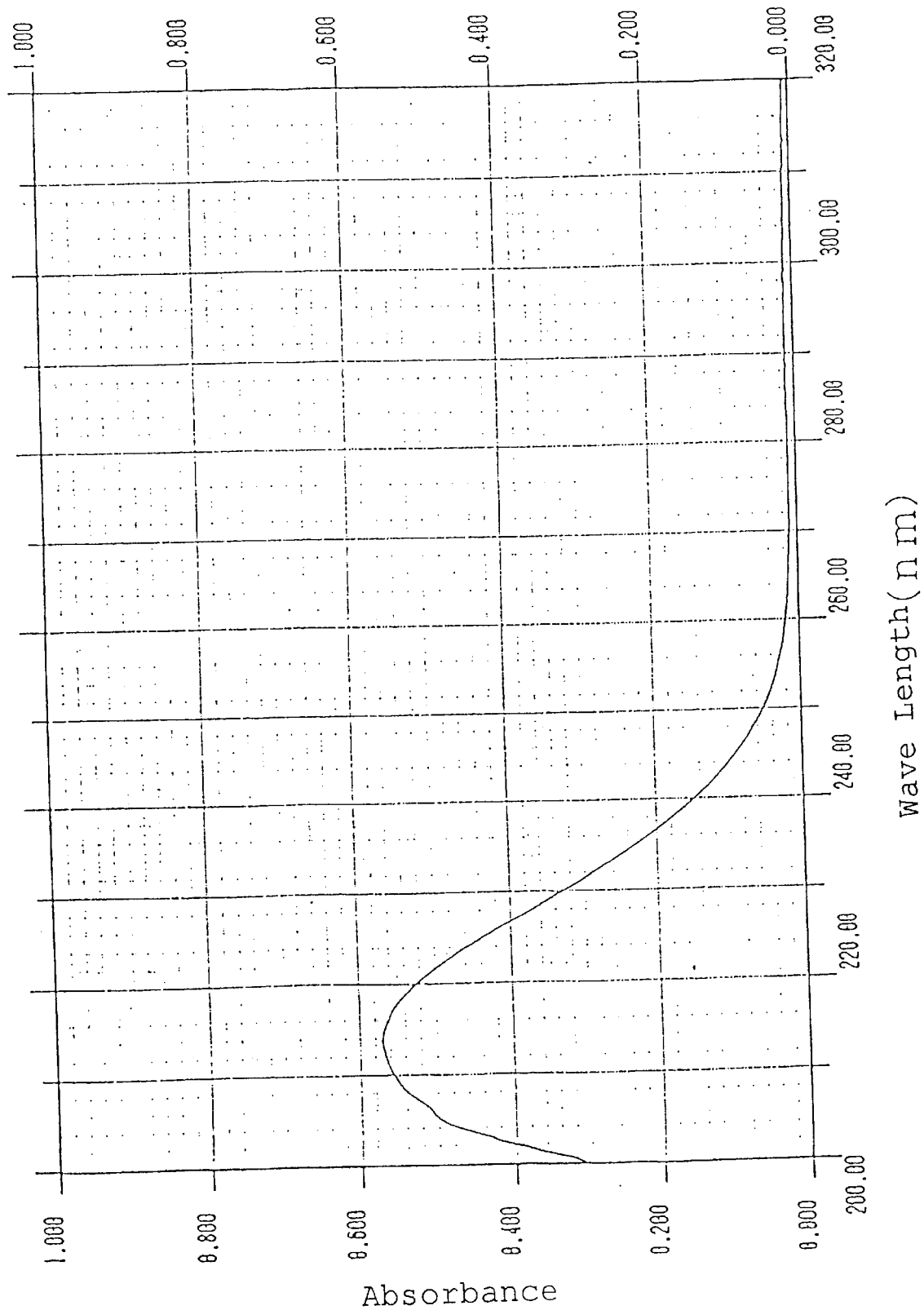
FIG. 18 shows a UV absorption spectrum of the reaction solution immediately after dissolution.
Figure 19:
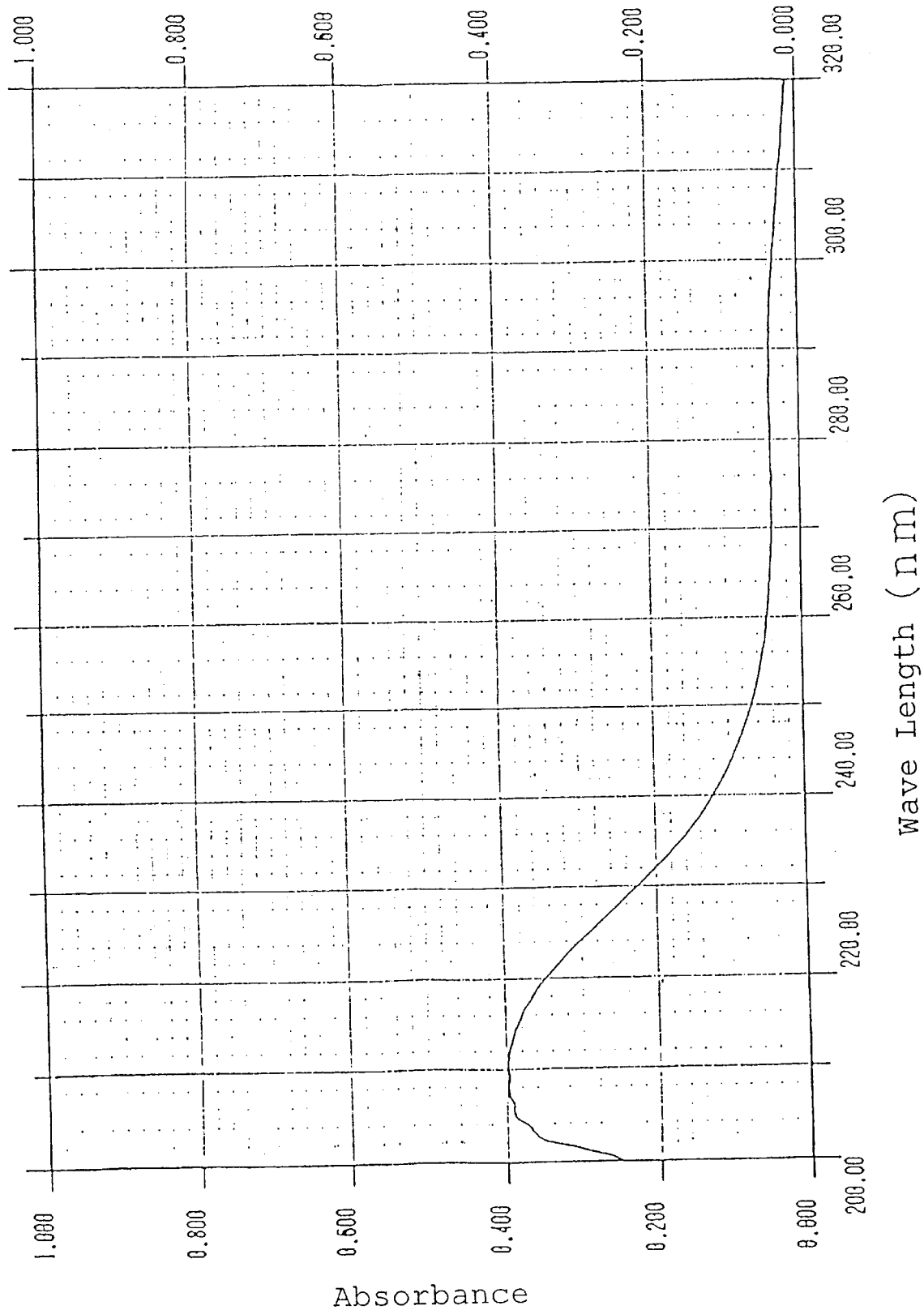
FIG. 19 shows a UV absorption spectrum of the reaction solution after the reaction for 50 minutes.

The result is given in FIG. 18 and in FIG. 19. Thus, Rig. 18 shows ultraviolet absorption spectrum of the reaction solution immediately after dissolution while FIG. 19 shows ultraviolet absorption spectrum of the reaction solution after the reaction for 50 minutes. In FIGS. 18 and 19, abscissa indicates wave length (nm) while ordinate indicates absorbance.

Figure 20:
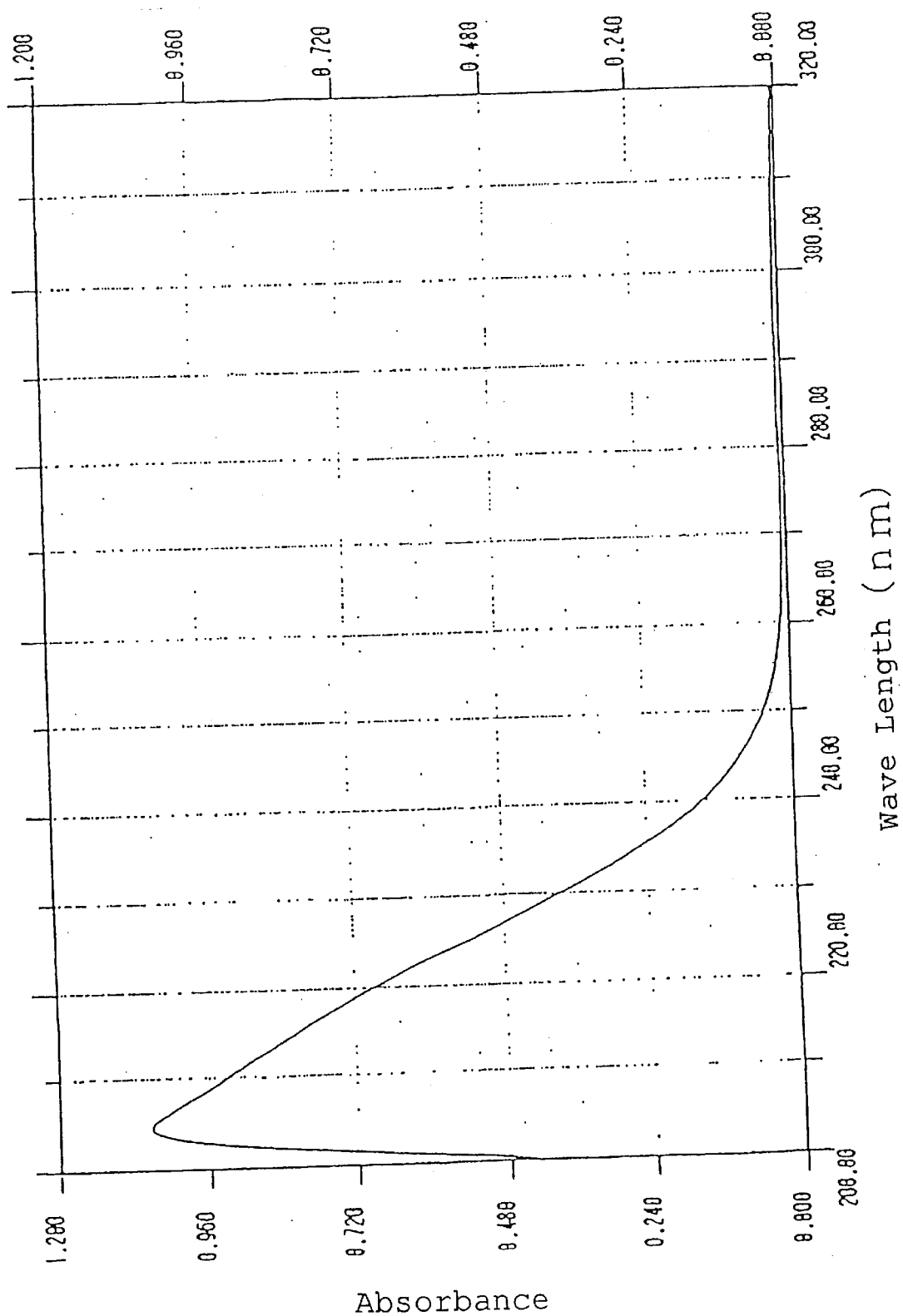
FIG. 20 shows a UV absorption spectrum of the reaction solution immediately after dissolution when glutathione is used.
Figure 21:
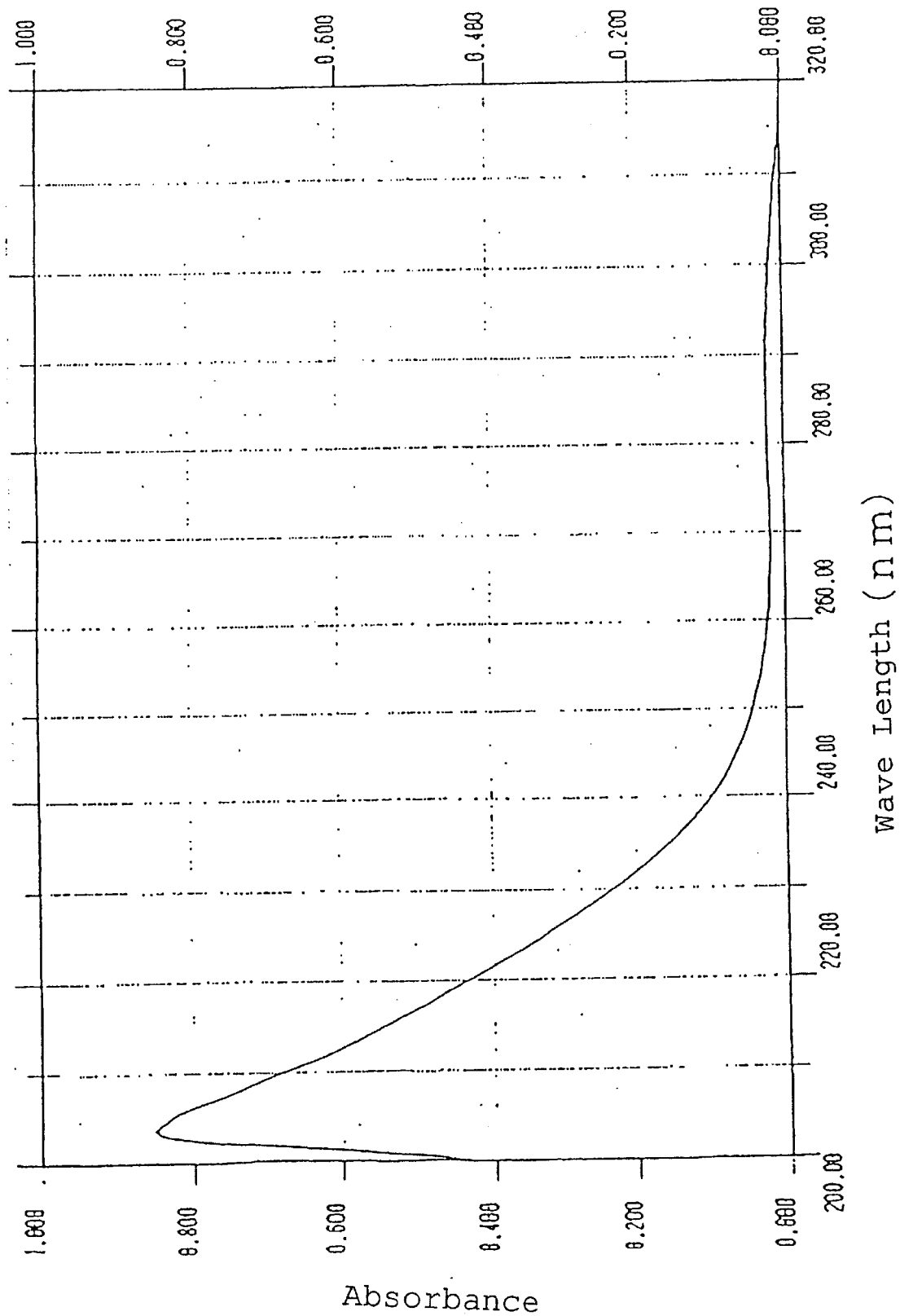
FIG. 21 shows a UV absorption spectrum of the reaction solution after the reaction for 50 minutes when glutathione is used.

The same operation was conducted using glutathione instead of L-cysteine hydrochloride. The result is shown in FIG. 20 and in FIG. 21. Thus, FIG. 20 shows ultraviolet absorption spectrum of the reaction solution immediately after dissolution using glutathione while FIG. 21 shows ultraviolet absorption spectrum of the reaction solution after reacting for 50 minutes using glutathione. In FIGS. 20 and 21, abscissa indicates wave length (nm) while ordinate indicates absorbance.

(5) A solution (60 μl) of 1.4M cyclopentenone in heavy water, 80 μl of 1M solution of L-cysteine in heavy water and a phosphate buffer saline solution (pH 7.2) prepared by the use of 160 μl of heavy water were mixed and made to react at 37° C. for three hours. $^{13}$C-Nucleomagnetic resonance (NMR) spectrum of the reaction solution was measured using a JNM-A500 (manufactured by Nippon Denshi). The result is shown below.

$^{13}$C-NMR

δ near 33 (1'-C), near 43 (4-C and 5-C), near 55 (2'-C) near 75 and near 78 (3-C), near 80 and near 81 (2-C), near 173 (3'-C), near 215 and near 217 (1-C).

Incidentally, the assignment numbers for the peaks in $^{13}$C-NMR are as shown in the following formula [XIII].

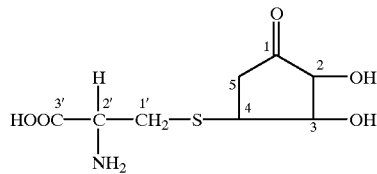

[XIII]

Figure 22:
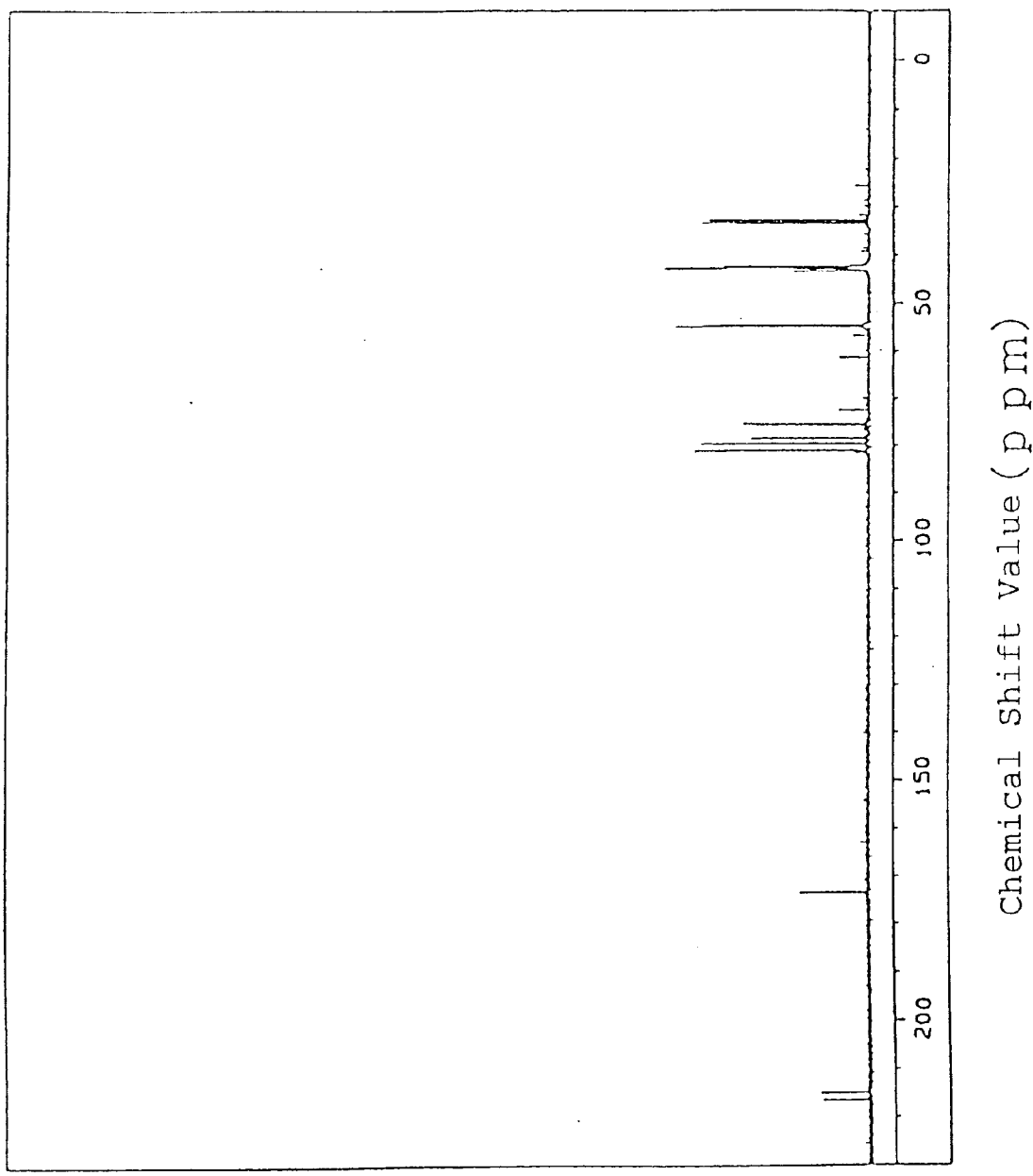
FIG. 22 shows a $^{13}$C-NMR spectrum of the reaction product.

$^{13}$C-NMR of this reaction product is shown in FIG. 22. In FIG. 22, abscissa indicates chemical shift values (ppm) while ordinate indicatres intensity of the signal.

Since the product in this reaction was a mixture of four kinds of diastereomers, four in maximum of signals were detected for each carbon atom and the chemical structure of the reaction product which was produced in this reaction solution was a cyclopentanone thio derivative illustrated by the above formula [IX].

As a result, it is apparent that the chemical structure of the reaction product having a peak eluting time of 4.0–4.3 minutes of FIG. 13 produced by the reaction of cyclopentenone with cysteine is the cyclopentanone thio derivative represented by the above formula [IX]. Said reaction product having a peak of eluding time of 4.0–4.3 minutes was fractionated to give the cyclopentanone thio derivative (hereinafter, referred to as CD) represented by the above formula [IX].

Example 4

(1) Aqueous solution (1.4M) (60 μl) of cyclopentenone, 600 μl of 200 mM aqueous solution (adjusted to pH 7.0 with NaOH) of glutathione (reduced type; sold by Nacalai Tesque; 170-10) and 1,340 μl of phosphate buffer saline solution (pH 7.2) were mixed and made to react at 37° C. for one hour. The reaction solution (700 μl) was filtered through a 0.5 μm Cosmo Nice Filter and a reaction product (hereinafter, referred to as GD1) of cyclopentenone with glutathione was separated by means of an HPLC under the following conditions.

Column: TSK gel ODS-80Ts (5 μm), 20 mm×25 cm (manufactured by Tosoh)

Mobile phase: A—0.1% aqueous solution of trifluoroacetic acid (TFA; manufactured by Merck; 8262); B—aqueous solution of 0.1% TFA/50% acetonitrile (manufactured by Nacalai Tesque; 004-30)

Flow rate: 9 ml/minute

Gradient: mobile phase A for 40 minutes from mobile phase A to B during 40 minutes after that, mobile B Detection: absorbance at 220 nm The above reaction solution (500 μl) was applied to an HPLC and the peak having a retention time of 27.7 minutes was fractionated and freeze-dried to isolate 5 mg of GD.

Figure 23:
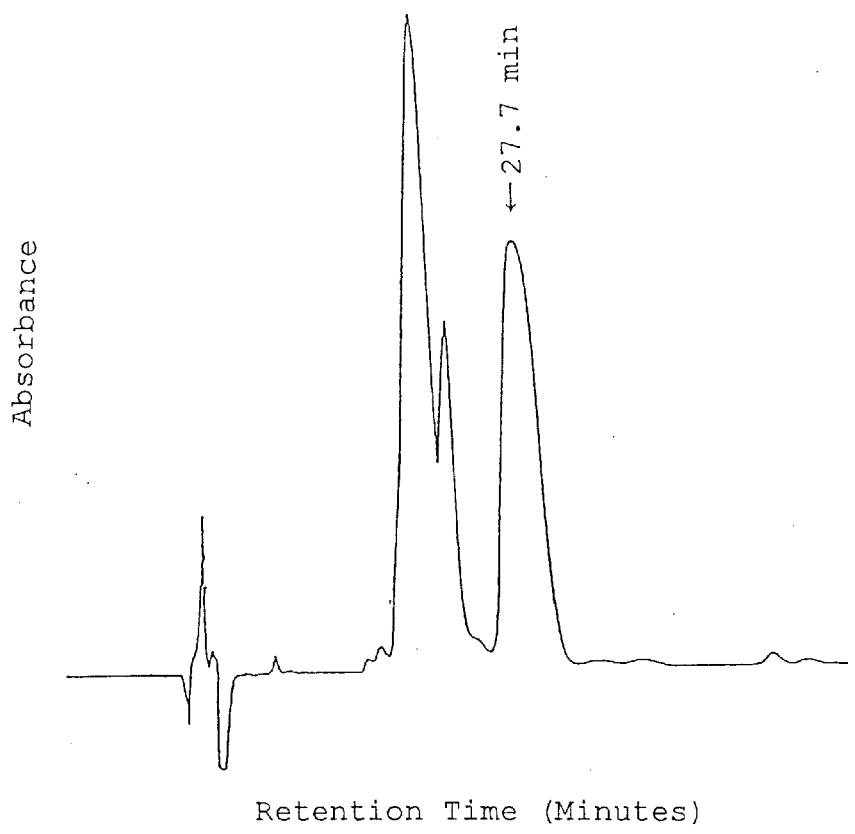
FIG. 23 shows a relation between retention time and absorbance.

The chromatogram is shown in FIG. 23. Thus, FIG. 23 shows a relation between retention time and absorbance where abscissa indicates retention time (minutes) while ordinate indicates absorbance at 220 nm.

(2) Structure of GD1 prepared in Example 4-(l) was analyzed. Nucleomagnetic resonance (NMR) spectrum was measured by a JNM-A500 (manufactured by Nippon Denshi); mass spectrum (MS) was measured by DX302 mass spectrometer (manufactured by Nippon Denshi); ultraviolet (UV) absorption spectrum was measured by a UV-2500 spectrophotometer (manufactured by Shimadzu); and infrared (IR) absorption spectrum was measured by an FTIR-8000PC infrared spectrophotometer (manufactured by Shimadzu). The result is as follows.

$^1$H-NMR

δ 2.07 (2H, m, 5'-H), 2.17 (1H, d-t, J=20.0, 11.0 Hz, 5-H), 2.45 (2H, m, 4'-H), 2.88 (1H, m, 1'-H), 2.95 (1H, m, 5-H), 3.08 (1H, m, 1'-H), 3.19 (1H, m, 4-H), 3.76 (1H, m, 3-H), 3.86 (3H, rm., 6'-H, 9'-H), 4.09 (1H, d, J=10.5 Hz, 2-H), 4.49 (1H, m, 2'-H).

The sample was dissolved in heavy water and the chemical shift of HOD was expressed as 4.65 ppm.

$^{13}$C-NMR

δ 26.4 (5'-C), 31.7 (4'-C), 33.3 (1'-C), 41.9 (9'-C), 42.4 or 42.6 (4-C), 42.8 (5-C), 53.4 (6'-C), 54.1 (2'-C), 79.4 or 79.6 (3-C), 81.1 (2-C), near 173 (3'-C, 7'-C, 8'-C, 10'-C), 214.9 (1-C)

The sample was dissolved in heavy water and the chemical shift value of dioxane was expressed as 67.4 ppm.

Incidentally, the assignment numbers for the peaks in $^1$H-NMR and $^{13}$C-NMR are as shown in the following formula [XIV]

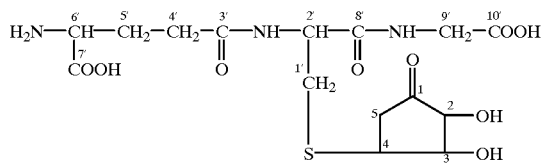

[XIV]

FAB-MS m/z 422 [M+H]$^+$

Glycerol was used as a matrix.

UV: terminal absorption

IR: $\lambda^{KBr}_{max}$ cm$^{-1}$ 3275, 1749, 1654, 1541, 1203, 1145 Diffuse reflectance method was used.

Figure 24:
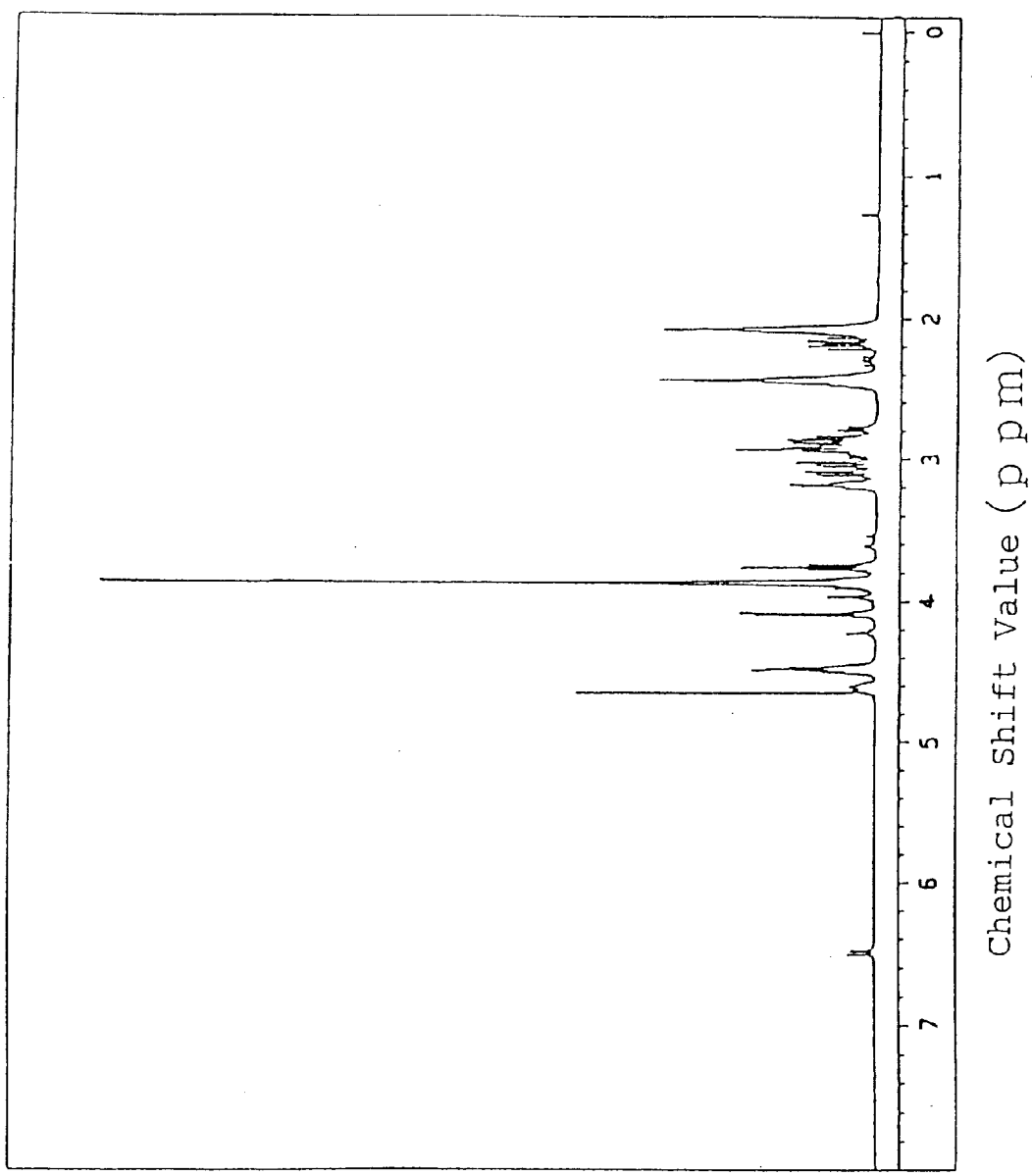
FIG. 24 shows a $^1$H-NMR spectrum of GD.
Figure 25:
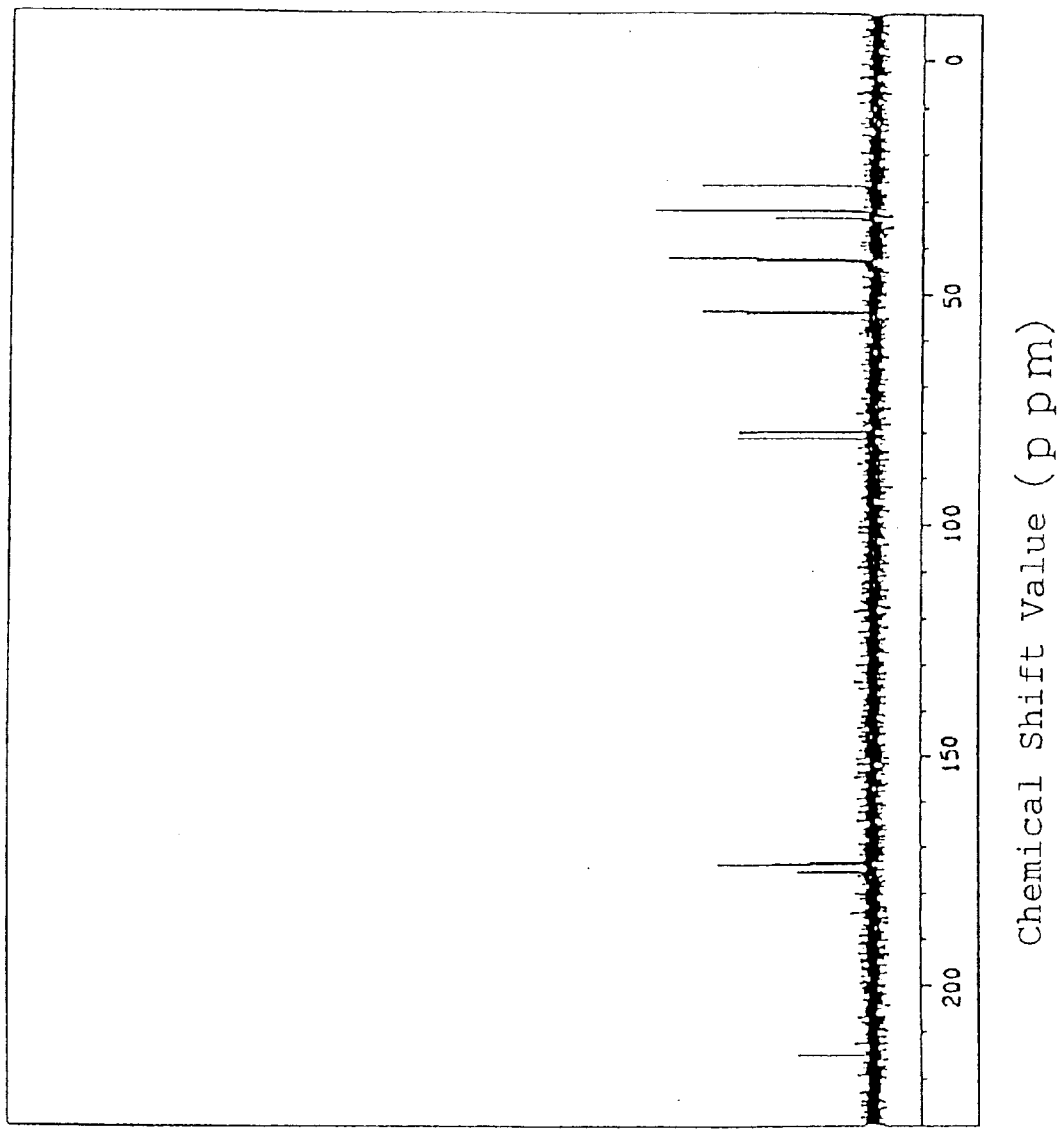
FIG. 25 shows a $^{13}$C-NMR spectrum of GD.
Figure 26:
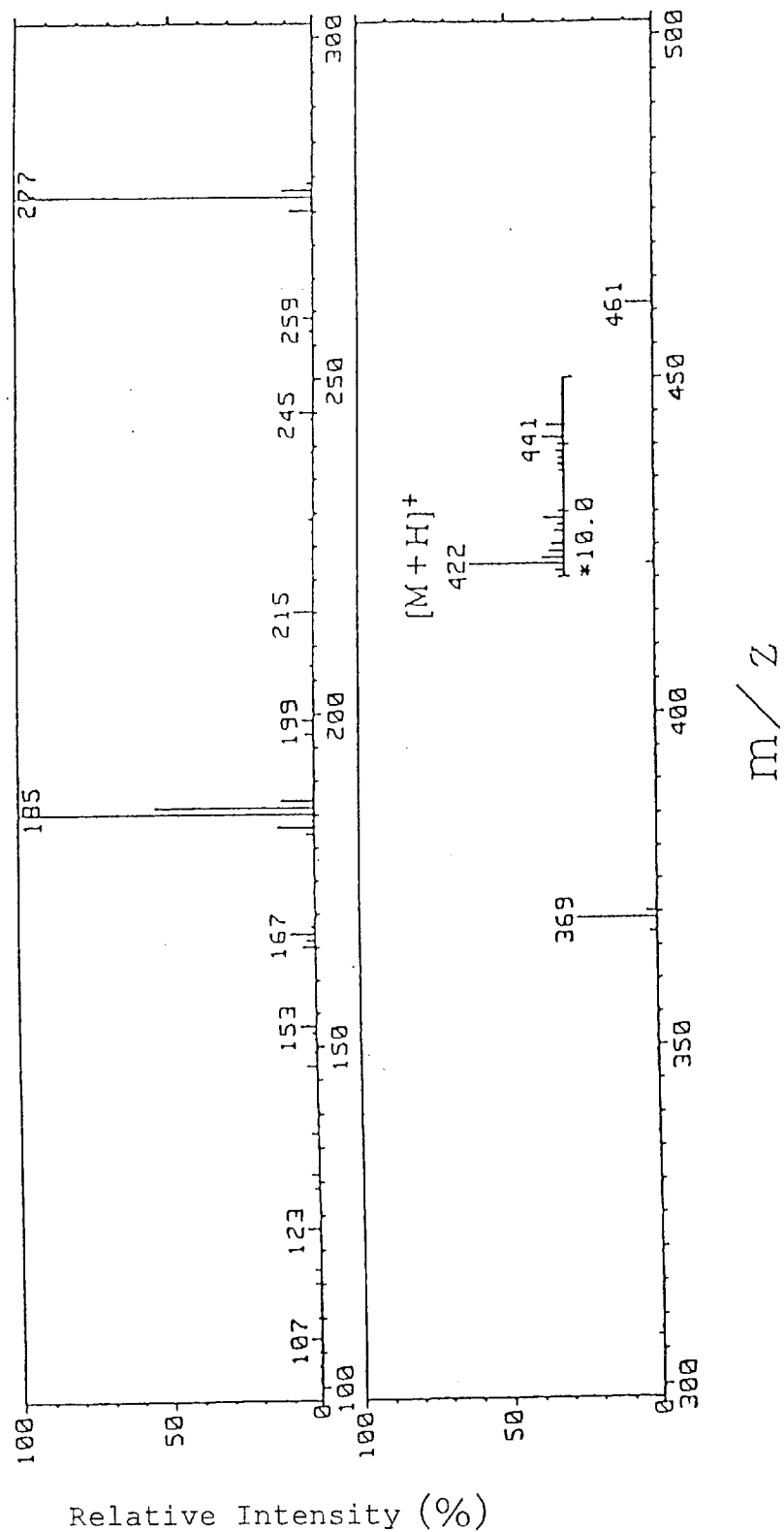
FIG. 26 shows a mass spectrum of GD.
Figure 27:
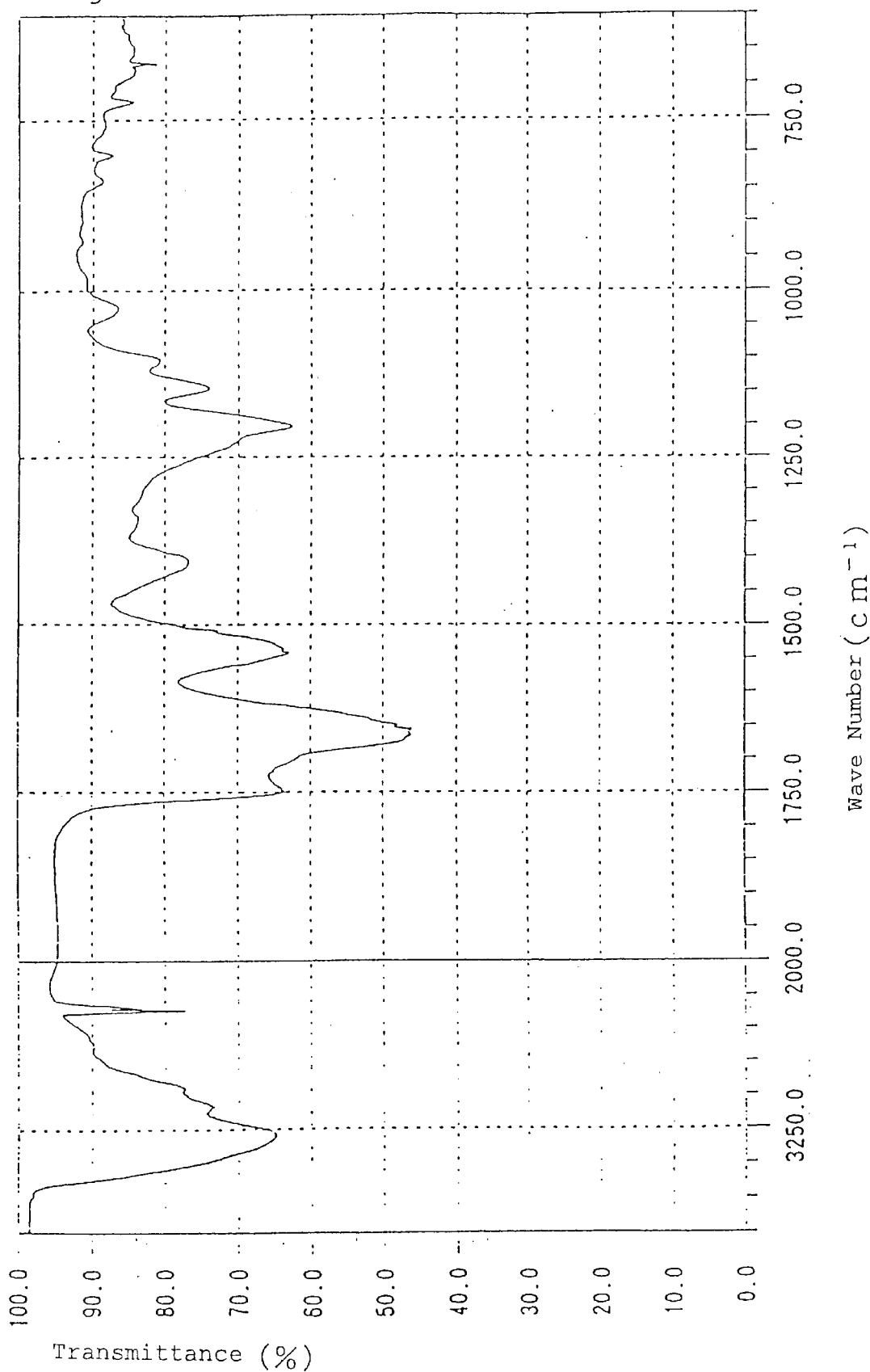
FIG. 27 shows an IR absorption spectrum of GD.

The results are shown in FIG. 24 to FIG. 27. Thus, FIG. 24 shows $^1$H-NMR spectrum of GD in which abscissa indicates chemical shift values (ppm) while ordinate indicates intensity of the signal; FIG. 25 shows $^{13}$C-NMR of GD in which abscissa indicates chemical shift values (ppm) while ordinal indicates intensity of the signal; FIG. 26 shows mass spectrum of GD in which abscissa indicates m/z values while ordinate indicates relative intensity (%); and FIG. 27 shows IR absorption spectrum of GD in which abscissa indicates wave number (cm$^{-1}$) while ordinate indicates transmittance (%).

From the above result, it has now been clear that GD is 2,3-dihydroxy-4-glutathion-S-yl-cyclopentanone shown as [X] hereinabove. Incidentally, GD is a mixture of four kinds of diastereomers and each diastereomer was separated from GD.

Example 5

(1) Each 0.5 ml of 0.2 mM CM, 0.8 mM CM or 1.6 mM CM was added to 4.5 ml of RPMI 1640 medium containing 10% of fetal calf serum and 2.5×10$^5$ HL-60 cells (promyelocytic leukemia cell) (ATCC CCL-240) and incubated at 37° C. for 24 hours or 48 hours in the presence of 5% carbon dioxide gas and the numbers of viable cells were measured.

As a result, CM has an intensive inhibition activity of the growth of cancer cells. In addition, apoptic bodies were detected in the cells under each of the cell-growth inhibiting concentrations.

Figure 28:
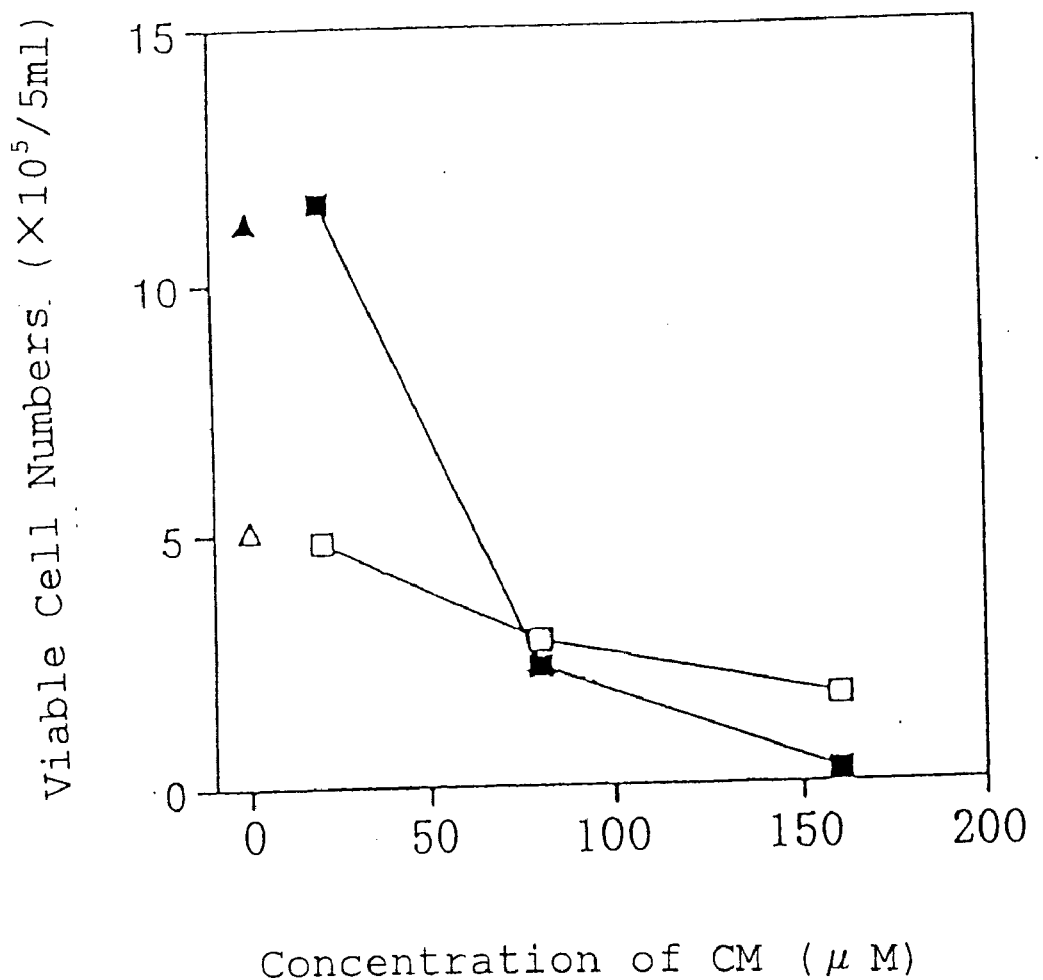
FIG. 28 shows an inhibition activity of CM to growth of cancer cells.

The result is shown in FIG. 28. Thus, FIG. 28 shows a relation between the concentration of the added sample (i.e. concentration of the CM in the medium) and the viable cell numbers where abscissa indicates concentration (μM) of the CM while ordinate indicates viable cell numbers (×10$^5$/5 ml) contained in 5 ml of the culture liquid. In FIG. 28, open square (□) indicates the case where CM is added followed by culturing for 24 hours; black square (■) indicates the case where CM is added followed by culturing for 48 hours; open triangle (Δ) indicates the case where no sample was added followed by culturing for 24 hours; and black triangle (▲) indicates the case where no sample was added followed by culturing for 48 hours.

(2) To each of the wells of a 96-well microtiter plate was added 8, 40, 200 or 1000 μM aqueous solution of GM or 10 μl of water as a control. HL-60 (ATCC CCL-240) was suspended in an RPMI 1640 medium containing 10% of fetal calf serum to make the concentration 5×10$^4$ cells/ml and each 90 μl thereof was placed in each well of the above-mentioned microtiter plate and incubated at 37° C. for 48 hours in the presence of 5% carbon dioxide. Incubation was conducted for four hours more after addition of 10 μl of a solution (5 mg/ml) of 3-(4,5-dimethylthiazol-2-yl)-2,5-diphenyltetrzolium bromide (MTT; manufactured by Sigma) in a phosphate-buffered saline solution and the state of growth of the cells was observed under a microscope. Further, 100 μl of 2-propanol containing 0.04N hydrochloric acid was added followed by stirring and an absorbance at 590 nm was measured.

AS a result, no growth of cells was detected in the section where 40 μM of GM was added (final concentration: 4.0 μM). Accordingly, it was clarified that GM completely inhibited the growth of HL-60 cells at the concentration of 4.0 μM. In the meanwhile, apoptic bodies were formed in the cells in each of the cell-growth-inhibiting concentrations.

(3) To each well of the 96-well microtiter plate was added 100, 200 or 400 μM aqueous solution of GM or CM or 10 μl of water as a control and the inhibition activity of growth of HL-60 was measured by the same method as mentioned in Example 5-(2). The degree of cell growth was, however, expressed in terms of the ratio (%) of the absorbance at 590 nm of the sample-added section to that of the water-added section (the control). The result is given in Table 1.

TABLE 1

|  | GM | CM |
|---|---|---|
| 40 μM | 3.2 | 2.8 |
| 20 μM | 1.8 | 16.1 |
| 10 μM | 14.8 | 48.9 |

(4) HL-60 cells (ATCC CCL240) which were incubated at 37° C. in an RPMI 1640 medium (manufactured by Nissui) containing 10% of fetal calf serum (manufactured by Gibco) treated at 56° C. for 30 minutes were suspended in the above medium to make the concentration 2.5×10$^5$ cells/4.5 ml. To this suspension was added 0.5 ml of 100 μM aqueous solution of GM (final concentration: 10 μM) followed by incubating at 37° C. in the presence of 5% carbon dioxide gas for 24 hours, 48 hours and 72 hours.

The incubated cells were stained with Trypan Blue and numbers of viable cells and dead cells were counted whereupon viable cell numbers and viability of cells were significantly reduced in the section to which 10 μM of GM was added as compared with the control where water was added. When the cultured cells were observed under an optical microscope, aggregation of nuclei, reduction in size of the cells and production of apoptic bodies were detected. Further, DNA was extracted from the cells and applied to an agarose gel electrophoresis whereupon fragmentation of DNA into a chromatin unit was observed. Incidentally, none of such a phenomenon was observed in the control where water was added.

Figure 29:
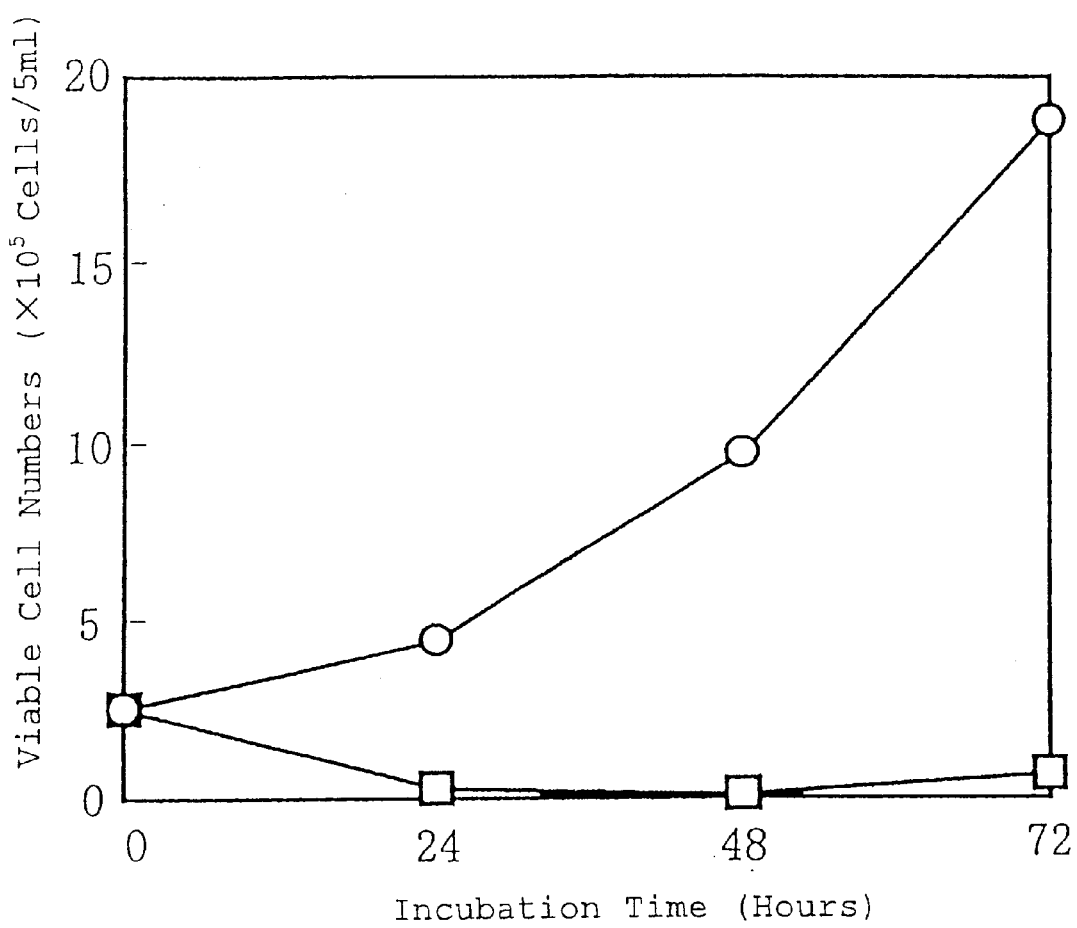
FIG. 29 shows an inhibition activity of CM to growth of cancer cells.

The result is shown in FIG. 29. Thus, FIG. 29 shows the relation between the incubation time and viable cell numbers in the incubated liquid when 10 μM of GM was added to a culture liquid of HL-60 where abscissa indicates an incubation time (hours), while ordinate indicates viable cell numbers (×10$^5$ cells/5 ml) in the incubated liquid. In FIG. 29, open square (□) indicates the case where 10 μM of GM was added while open circle (○) indicates the control where water was added.

(5) To each well of the 96-well microtiter plate was added 4.12, 12.3, 37.0, 111, 333 or 1000 μM aqueous solution of GD or 10 μl of water as a control. HL-60 (ATCC CCL-240)

was suspended in an RPMI 1640 medium containing 10% of fetal calf serum to make the concentration $5\times10^4$ cells/ml and each 90 µl thereof was placed in each well of the above-mentioned microtiter plate followed by incubating at 37° C. for 48 hours in the presence of 5% carbon dioxide gas. The incubation was conducted for four hours more after addition of 10 µl of 5 mg/ml solution of 3-(4,5-dimethylthiazol-2-yl)-2,5-diphenyltetrazolium bromide (MTT; manufactured by Sigma) in a phosphate-buffered saline solution and the state of growth of the cells was observed under a microscope. In the meanwhile, 100 µl of 2-propanol containing 0.04N HCl was added followed by well stirring and the absorbance at 590 nm was measured.

As a result, no cell growth was detected in the section to which 37.0 µM of GD was added (final concentration: 3.70 µM). Accordingly, it was clarified that GD completely inhibited the growth of HL-60 cells at the concentration of 3.70 µM. Incidentally, apoptic bodies were detected in the cells in each of the cell-growth-inhibiting concentrations.

(6) Cyclopentenone and L-cysteine hydrochloride were dissolved in a phosphate buffered saline solution (pH 7.2) to make their concentrations 55 mM and 80 mM, respectively and made to react at 37° C. for 15 minutes at pH 7.2. Apart of the reaction solution was analyzed by a reversed phase HPLC using a column of TSK gel ODS-80Ts (4.6 mm×250 mm; manufactured by Tosoh)at the flow rate of 1 ml/minute using 0.1% aqueous solution of trifluoroacetic acid as a mobile phase whereupon no cyclopentenone was detected. This reaction solution was a solution containing 55 mM of CD.

Inhibition activity of the growth of cancer cells was measured for 100, 200 or 400 µM aqueous solution of GD or CD by the same manner as in Example 5-(4). Degree of cell growth was, however, expressed in terms of the ratio (%) of the absorbance at 590 nm of the section to which the sample was added to that of the control where water was added.

The result is shown in Table 2.

TABLE 2

|  | GD | CD |
| --- | --- | --- |
| 40 µM | 2.1 | 5.3 |
| 20 µM | 5.8 | 56.2 |
| 10 µM | 47.2 | 89.0 |

As shown in Table 2, GD and CD has inhibition activity of the growth of cancer cells. Apoptic bodies were produced in the cells at each of the concentrations whereby the cell growth was inhibited.

Thus, as shown in Example 5, each of the compounds showed an inhibition activity of the growth of cancer cells and an induction activity of the apoptosis. Each of the diastereomers showed the same effect as well.

Example 6

GM was diluted with a physiological saline solution to a predetermined concentration and subjected to the following tests.

(1) Meth A cells ($2\times10^6$ cells/mouse) were subcutaneously injected to abdomen of female BALB/c mice (body weight: about 20 g) of eight weeks age. After that, GM (5 mg/kg/day) was subcutaneously injected for consecutive five days to the same site. On the other hand, a physiological saline solution was subcutaneously injected to the control group by the same manner. After two weeks, the cancer tissues generated in abdomen of the mice were excised and their weight were measured. As compared with the control group, the group to which GM was administered showed a significant inhibiting action to the growth of cancer. CM, CD and GD gave the similar results as well.

(2) Mouse leukemia P-388 ($1.1\times10^6$ cells/mouse) was intraperitoneally injected to female DBA/2 mice (body weight: about 20 g) of seven weeks age. After that, GM, CM, GD or CD (10 mg/kg/day) was intraperitoneally injected for consecutive five clays. In the meanwhile, a physiological saline solution was intraperitoneally injected to the control group by the same manner. In the two group each consisting of eight mice, survived numbers, average survived days and macrobiotic rate of the mice were calculated. As compared with the control group, average survived days were prolonged in each of the sample-administered group whereby a significant macrobiotic effect was noted. The systems using Sarcoma-180/ICR mice, IMC/CDF1 mice and EAC/DDY mice showed the same macrobiotic effect as well.

Thus, as shown in Example 6 as hereinabove, GM, CM, GD or CD showed anticancer effect. Each of the diastereomers showed the same result as well.

Example 7

Bacillus subtilis IFO 3021 was incubated (by mans of a seed culture) overnight in a sensitive bouillon medium (manufactured by Nissui). Absorbance at 600 nm was measured and viable cell numbers were calculated from the previously-prepared calibration curve showing the relation between the viable cell numbers and absorbance at 600 nm. The seed-cultured liquid was diluted with a fresh sensitive bouillon medium to make the concentration $1\times10^6$ cells/ml and each 180 µl thereof was placed in each well of the 96-well microtiter plate. Each 20 µl of aqueous solution of GM (4 mg/ml or 2 mg/ml) or water was added to each well followed by allowing to a stationary culture at 37° C. for one night (main incubation) In the meanwhile, a part of the seed culture liquid was diluted with sterilized water, spread onto a sensitive bouillon agar plate medium and incubated at 37° C. for one night and the colonies were counted to measure the precise viable cell numbers.

The cultured liquid in each of the wells was diluted with sterilized water, spread onto a sensitive bouillon agar plate medium and incubated at 37° C. for one night and the colonies were counter to measure the viable cell numbers.

As a result, the viable cell numbers at the section to which 4 mg/ml of GM was added (final concentration: 400 µg/ml) were $4.4\times10^7$ cells/ml and were lower than the water-added section where the numbers were $1.3\times10^8$ cell/ml. Accordingly, GM has an inhibition activity to the growth of the above-mentioned microbe at the concentration of 400 µg/ml. CM, GD, CD or each of the diastereomers thereof and diastereomer of GM showed the same results. Further, those compounds has similar antibacterial activity to other microbes as well.

Example 8

(1) LPS (lipopolysaccharide manufactured by Sigma) was intraperitoneally injected (10 µg/mouse) to female CDF1 mice of eight weeks age (purchased from Nippon SLC at seven weeks age with bodyweight of 20 g followed by subjecting a preliminary breeding for one week at our end) and endotoxin-shock models were prepared. GM was orally administered at the dose of 100 and 1000 mg/kg at thirty minutes before administration of LPS. After one hour from the administration of LPS, blood was collected from the mice, serum was separated and amount of the tumor necrosis factor-α in the serum was measured by a commercially available ELISA kit (manufactured by Endogen). The result is shown in Table 3. Thus, production of tumor necrosis factor was significantly inhibited in a group administered with 1000 mg/kg of GM as compared with the control to which distilled water was administered.

TABLE 3

| Group | Dose (mg/kg) | Numbers of Mice | TNF in Serum (ng/ml) (Mean ± SE) |
| --- | --- | --- | --- |
| Control | | 4 | 2.32 ± 0.15 |
| GM-Given Group | 1000 | 5 | 1.16 ± 0.26 |
| | 100 | 5 | 2.22 ± 0.26 |

(2) Paraffin oil (Cosmo Bio) (2 ml) was intraperitoneally administered to female CDF1 mice of eight weeks age to induce celiac macrophage (Mφ). After one week from administration of paraffin oil, 4 ml of an RPMI-1640 medium (Gibco) was intraperitoneally infused, well massaged and recovered to give celiac cells.

The celiac cells were washed with an RPMI-1640 medium twice and suspended in an PPMI1640 medium containing 10% of fetal calf serum (FCS; High-Clone) to adjust the cell concentration to $1 \times 10^6$ cells/ml. The cell solution (1 ml) prepared as such was planted on a 24-well plate and incubated in a $CO_2$ incubator at 37° C. for two hours. Non-adhesion cells contained in the supernatant liquid after incubation was removed and the adhesion cells were used as celiac M.

To each of the well of the plate was added 800 μl of RPMI-1640 medium containing 10% of FCS, then 100 μl of 1, 10, 100 and 1000 μM GM dissolved in a physiological saline solution (manufactured by Otsuka Pharmaceutical) was added thereto and incubation was conducted in a $CO_2$ incubator at 37° C. for one hour.

After the incubation, 100 μl of 100 ng/ml LPS (manufactured by Sigma) was added and incubation was conducted for 24 hours more. After completion of the incubation, the supernatant liquid was recovered therefrom and the amount of TNF-a produced therein was determined using a commercially available ELISA kit (manufactured by Endogen).

Figure 30:
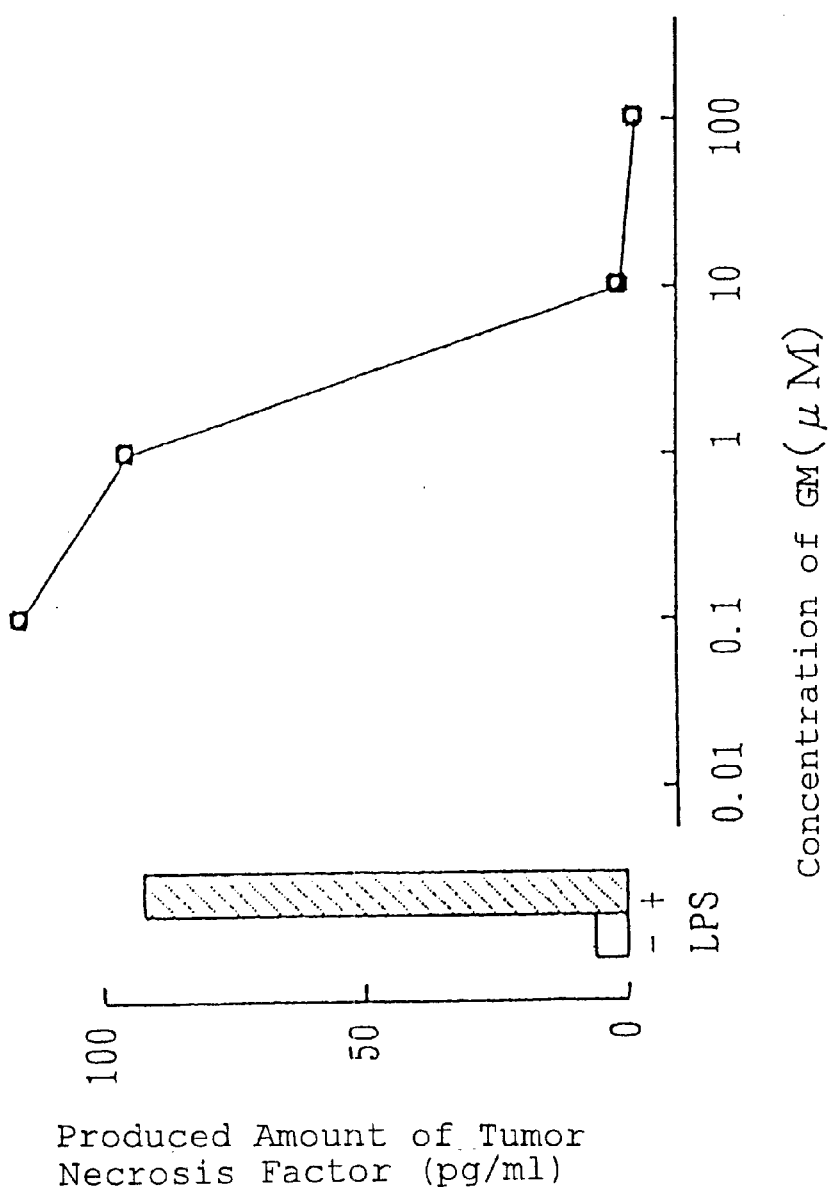
FIG. 30 shows a relation between the quantity of GM and the amount of production of tumor necrosis factor.

The result is shown in FIG. 30. Thus, FIG. 30 shows the relation between the amount of GM and the produced amount of tumor necrosis factor in which ordinate indicates a produced amount of tumor necrosis factor (pg/ml) while abscissa indicates concentration of GM (μM). Incidentally, bar graph shows the case of the control where no GM was added.

GM in a concentration of not less than 10 μM significantly inhibited the production of tumor necrosis factor from celiac macrophage of mice induced by LPS.

As shown in the above-mentioned Example 8, GM has an inhibition activity of the production of tumor necrosis factor. CM, GD, CD or each of diastereomers thereof and each diastereomer of GM showed the similar results as well.

Example 9

Carrageenan-induced pedal edema models which were animal model of chronic articular rheumatism were prepared as follows using male Lewis rats [purchased from Seac-Yoshitomi when five weeks age (body weight: about 130 g) followed by subjecting to a preliminary breeding for one week at our end] and the test drugs were evaluated.

To the rats which were fasted since 18 hours before initiation of the experiment was orally administered with 10 ml/kg of GM which was prepared with distilled water (manufactured by Otsuka Pharmaceutical) to make 10 and 100 mg/ml.

After 0.5 hour from administration of the test drug, 100 μl/rat of 1% suspension of carrageenan (manufactured by Wako) in a physiologically saline solution (manufactured by Otsuka Pharmaceutical) was injected to right paw to induce pedal edema. After three hours from the carrageenan injection, volume of right paw of the rat was measured by a pedal volume measuring device (manufactured by UGO BASILE). Incidentally, the measured value was expressed by calculating the increasing rate from the right paw volume of each rat measured before the carrageenan administration.

Figure 31:
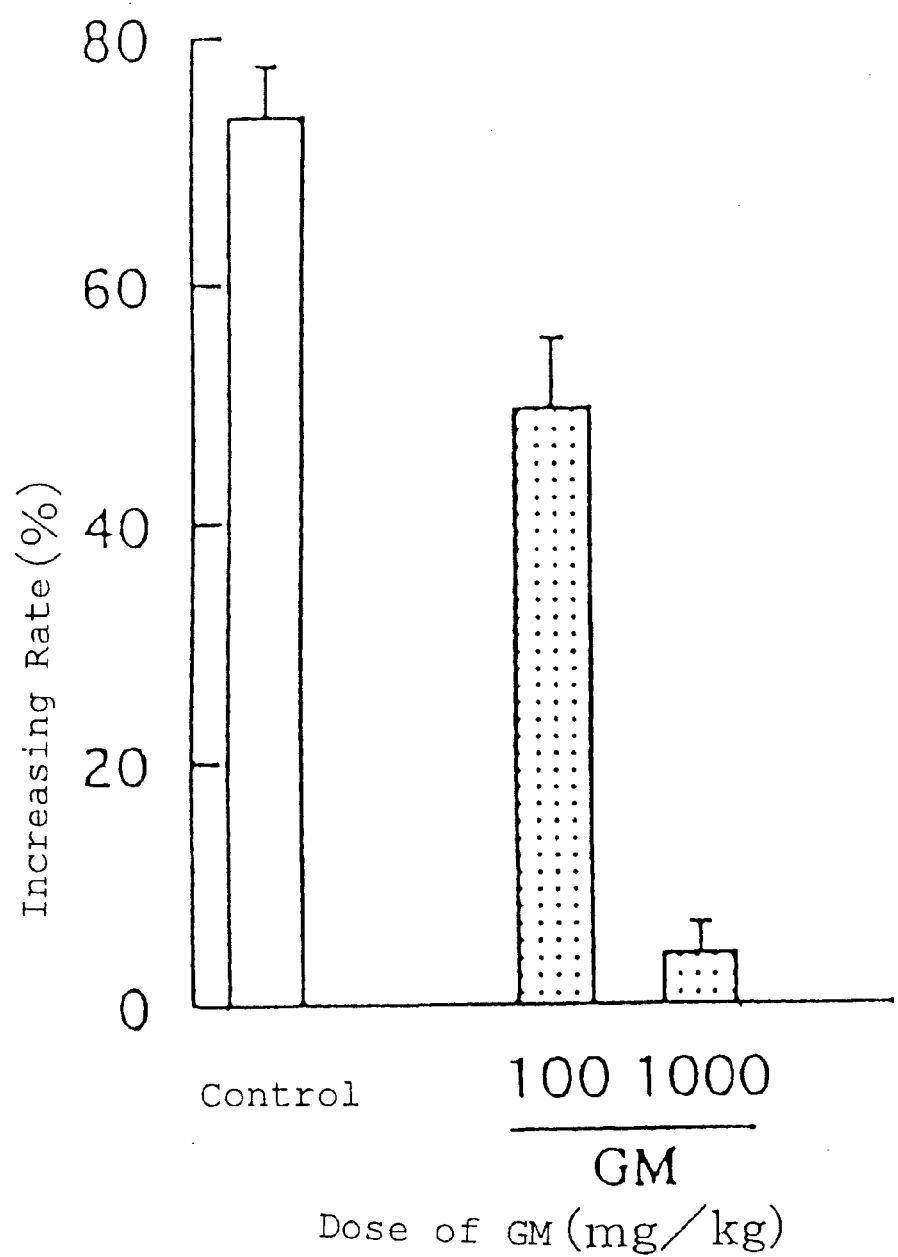
FIG. 31 shows a relation between the quantity of GM and the increasing rate of pedal edema.

The result is shown in FIG. 31. Thus, FIG. 31 shows the relation between the amount of GM and the increasing rate of the pedal edema in which ordinate indicates an increasing rate (%) while abscissa indicates a dose of GM (mg/kg).

GM has a significant inhibition activity at the dose of 100 mg/kg and higher.

CM, GD, CD or each of diastereomers thereof and each diastereomer of GM showed the similar result as well.

Example 10

Inhibition activity of GM to NO production and to cell damage was measured as follows using mouse macrophage cell strain RAW264.7 cells (ATCC TIB 71) and LPS.

Dulbecco-modified Eagle's medium (manufactured by Life Technologies Oriental; 11054-020) containing 2 mM of L-glutamine (manufactured by Life Technologies Oriental; 25030-149) containing no Phenol Red containing 5 ml of 10% fetal calf serum (manufactured by Gibco) containing $1.5 \times 10^6$ cells of RAW 264.7 was incubated in a six-well tissue culture plate in the presence of 5% carbon dioxide gas at 37° C. for 12 hours, 50μl of 50μg/ml LPS (manufactured by Sigma; L-2012) was added, then each 50 μl of 250 )i M Mn or 100 μH GM was added to each well, incubation was further continued for additional 12 hours and, after that, $NO_2^-$ produced by oxidation of NO in the medium and amount of viable cell numbers were measured. Incidentally, a sect-Lon where no LPS was added and a section where no GM was added were prepared as controls.

For the measurement of $NO_2^-$, 100 μl of incubated supernatant fluid was separated from each well, 20 μl of 50 μg/ml solution of 2,3-diaminonaphthal-ene (manufactured by Dojindo Laboratories; 341-07021) (a solution in 0.62N hydrochloric acid) was added, there mixture was allowed to stand for 15 minutes, then 5 μl of 2.8N aqueous solution of sodium hydroxide was added and the fluorescence of the resulting naphthalene triazole was measured by a Titertec Fluoroscan II (sold by Dainippon Pharmaceutical) at excitation wave length of 355 nm and measuring wave length of 460 nm. All experiments were conducted in two series, a control value of the section to which no LPS was added was deducted from the average value thereof and a comparison was conducted in terms of the relative value of each section to the value of the section to which LPS was added.

The result was that GM inhibited the NO production induced by LPS in RAW 264.7 cells and further that it inhibited the cell damage in RAW 264.7 cells caused by LPS.

Figure 32:
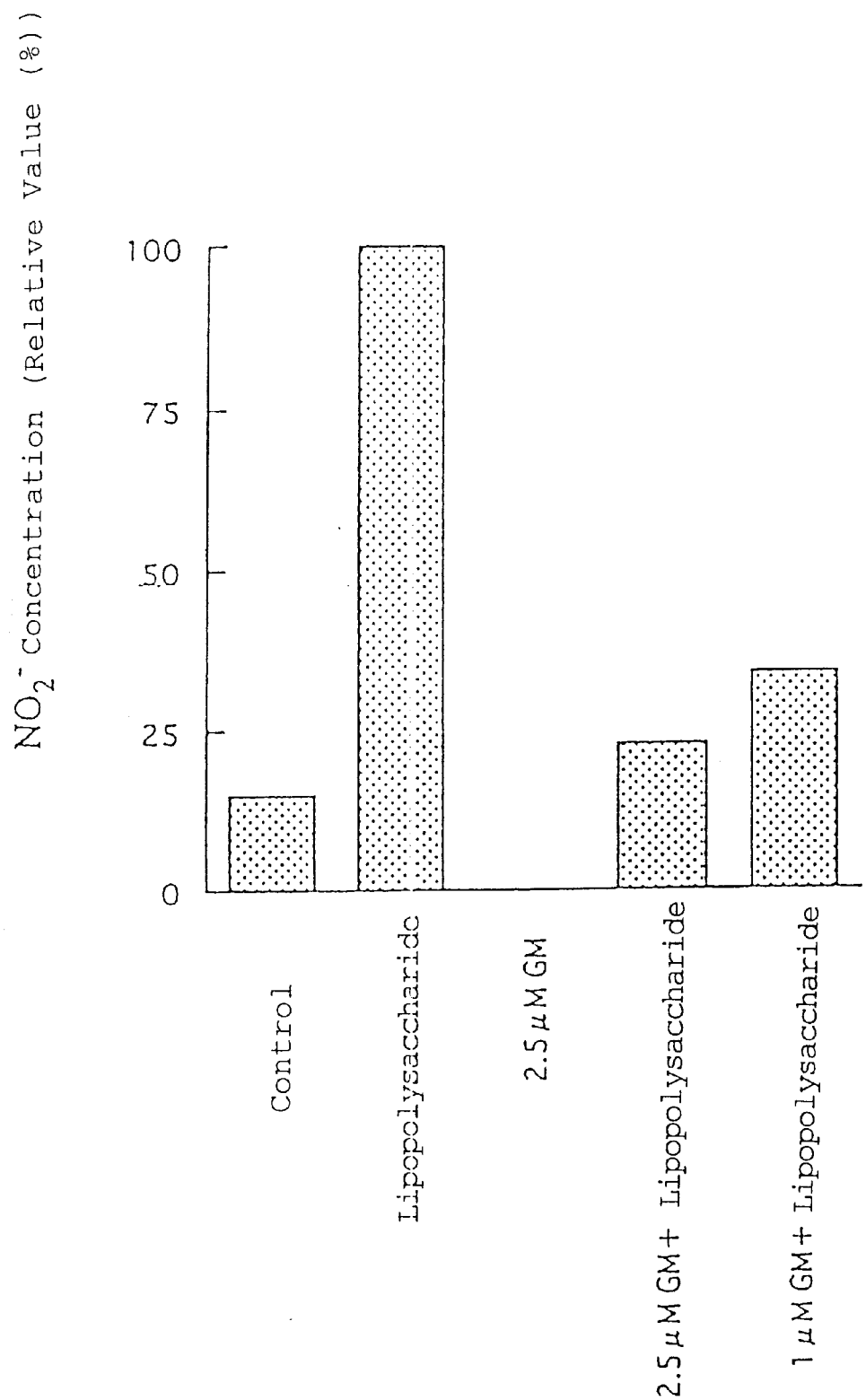
FIG. 32 shows a relation between the $NO_2^-$ concentration and the GM concentration in a medium.
Figure 33:
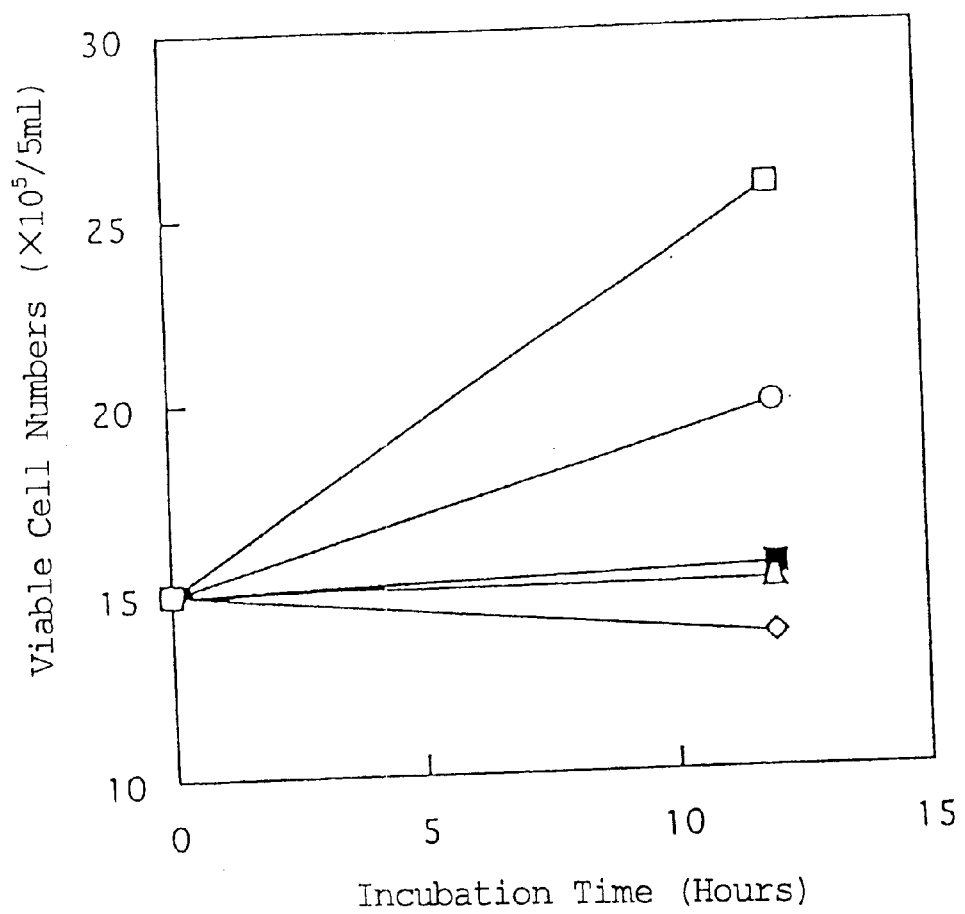
FIG. 33 shows a relation between the incubation time and viable cell numbers.

The results are shown in FIG. 32 and in FIG. 33. FIG. 32 shows the relation between the GM concentration and $NO_2^-$ concentration in the culture liquid in which ordinate indicates a relative value (%) of the $NO_2^-$ concentration. FIG. 33 shows the relation between the incubation time and viable cell numbers in the presence of GM in which abscissa indicates an incubation time (hours) while ordinate is viable cell numbers ($\times 10^5/5$ ml) contained in 5 ml of the culture liquid. In FIG. 33, open square (□) indicates the case where no LPS was added; open rhomb (◇) indicates the case where LPS was added; open circle (○) indicates the case where 2.5 μM GM was added; open triangle (△) indicates the case 2.5 μM GM and LPS were added; and black square (■) indicates the case where 1 μM GM and LPS were added.

As such, GM showed an inhibiting action to the NO production. CM, GD, CD or each of diastereomers thereof and each diastereomer of GM gave the similar results as well.

Example 11

DSEK cell (cell strain stored at the Department of Second Internal Medicine, Integrated Medical Center, Saitama College of Medicine) which was a fibroblast strain established from synovial membrane of a patient suffering from chronic articular rheumatism was incubated in an Iscob-modified Dulbecco medium (IMDM, manufactured by Gibco, 12440-053) containing 10% fetal bovine serum (FBS, manufactured by Gibco, 26140-079) at 37° C. in the presence of 5% carbon dioxide gas until confluent and then the cells were collected by peeling off with trypsin-EDTA (manufactured by Gicbo, 25300-054). The cells were suspended in the above-mentioned medium until 25,000 cells/ml were resulted and each 100 μl was placed in each well of a 96-well microtiter plate. After five days from incubation when the state of confluence was almost achieved, the medium was discarded and then the above-mentioned medium containing 2.5, 5, 10, 20 or 30 μM of GM was added. After incubating for 24, 48 or 72 hours, 10 μl of a premix WST-1 (manufactured by Takara Shuzo, MK400) was added thereto followed by subjecting to a reaction at 37° C. for four hours. The value obtained by deducting the absorbance at 650 nm ($A_{650}$) from that at 450 nm ($A_{450}$) was defined as a degree of growth of cell.

The result is as shown in Table 4.

TABLE 4

| Concentration (μM) | $A_{450}-A_{650}$ after | |
|---|---|---|
| | 24 hours | 48 hours |
| 0 | 0.846 | 1.270 |
| 2.5 | 0.768 | 1.133 |
| 5 | 0.621 | 0.942 |
| 10 | 0.420 | 0.486 |
| 20 | 0.238 | 0.185 |
| 30 | 0.241 | 0.196 |

In both cases of incubating for 24 hours and 48 hours, cell growth was inhibited in the sections where 5 μM or more GM was added as compared with the control where water was added and, in the section where 10 μM of GM was added, production of apoptic bodies was noted. In the section where 20 μM or more GM was added, viable cells were hardly noted.

As such, GM showed apoptosis-inducing action and growth-inhibiting action to synovial cells. CM, GD, CD or each of the diastereomers thereof and each diastereomer of GM showed the similar results as well.

Example 12

(1) Jurkat cells (ATCC TIB-152) and Molt-3 cells (ATCC CRL-1552) which were human T cell leukemia cell stain were incubated in an RPMI 1640 medium (manufactured by Gibco BRL) containing 10% fetal calf serum (FCS, manufactured by Bio Whittaker) at 37° C. in the presence of 5% $CO_2$ and the cells were then suspended in the above-mentioned medium containing 0, 5, 10 or 20 μM of GM to make the cell numbers $5 \times 10^5$ cells/ml followed by incubating for 24 hours. Cell growth was measured by an MTT method [Mosmann, et al.: J. Immunol. Methods, volume 65, pages 55–63 (1983)] wherein degree of cell growth was determined by the absorbance at 560 nm.

The result was that, in both cell strains, cell growth was inhibited to an extent of about 50% and not less than 75% in the sections where 10 μM and 20 μM of GM were added, respectively as compared with the control where water was added. In case 5 μM or less GM was added, there was no significant effect in the growth of cells.

As such, GM inhibited, in a concentration-dependent manner, the growth of Jurkat cells and Molt-3 cells which were T cell leukemia cell strains.

Figure 34:
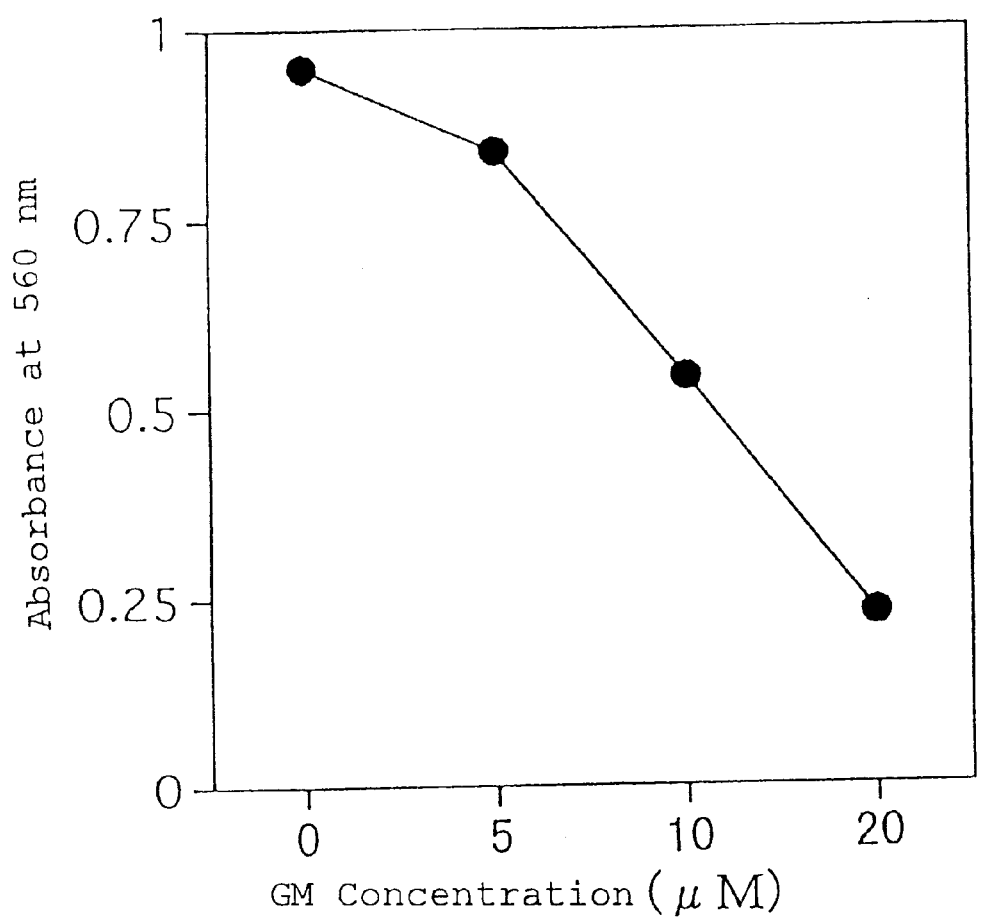
FIG. 34 shows an influence of GM on the growth of Jurkat cells.
Figure 35:
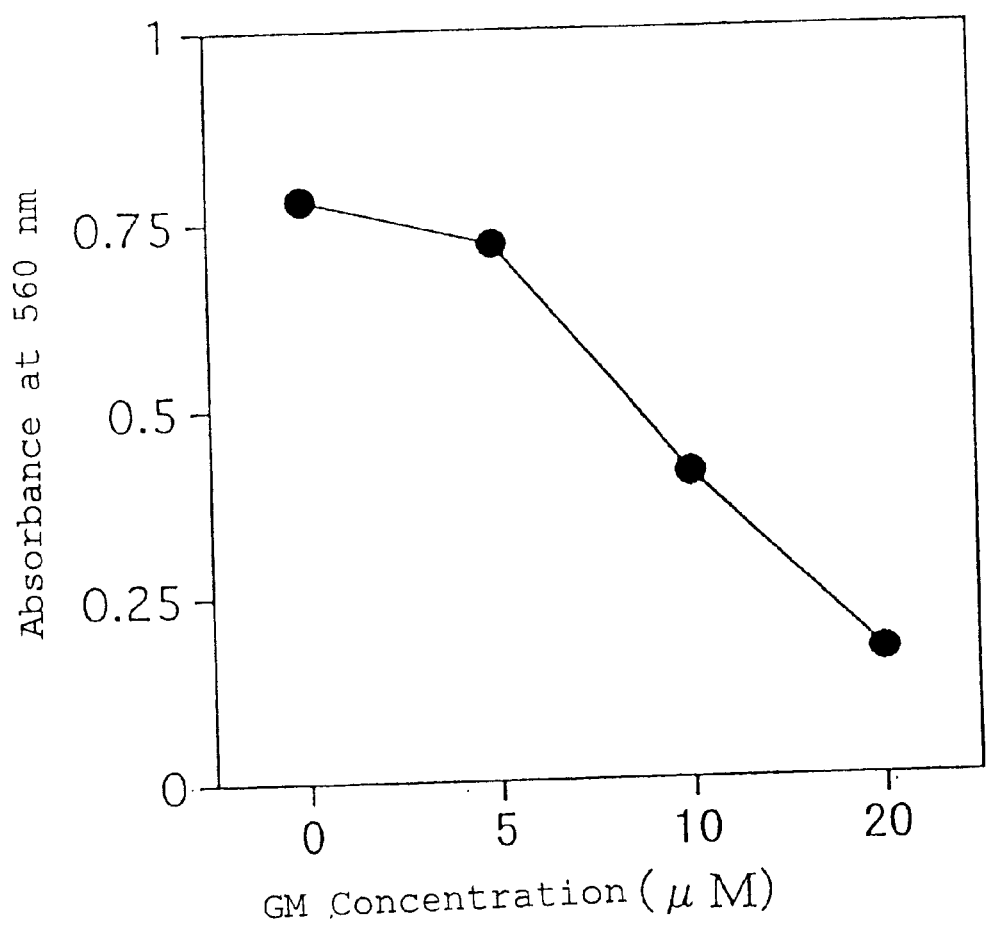
FIG. 35 shows an influence of GM on the growth of Molt-3 cells.

The results are given in FIG. 34 and FIG. 35. FIG. 34 shows an influence of GM on the growth of Jurkat cells while FIG. 35 shows an influence of GM on the growth of Molt-3 cells. In FIG. 34 and FIG. 35, abscissa indicates GM concentration (a M) while ordinate indicates absorbance at 560 nm.

(2) Influence of GM on Fas antigen expression (productive induction) in Jurkat cells and Molt-3 cells was measured as follows. In a 10% FCS-containing RPMI 1640 medium containing 0, 1, 5, 10 or 20 μM of cyclopentenone or GM, $5 \times 10^5$ cell/ml of Jurkat cells or Molt-3 cells were incubated at 37° C. for 24 hours in the presence of 5% of $CO_2$ and then subjected to a two-step immunostaining using an anti-Fas antibody (manufactured by Boehringer-Ingelheim) in accordance with a method of Munker [Munker, R.: Ann. Hematol., volume 70, pages 15–17 (1995)].

Fluorescence intensity of the stained $1 \times 10^4$ cells was measured by a flow cytometer (Orthocytron; manufactured by Ortho Diagnostic Systems) and ratio of the cell showing a predetermined or higher fluorescence intensity which were Fas antigen-expressing cells was calculated.

The result was that, in both cell strains, the ratio of Fas antigen-expressing cells increased on a concentration-dependent manner when 1–10 μM of GM was added and, when 20 μM was added, the outcome was almost same as that in the case of addition of 10 μM.

Figure 36:
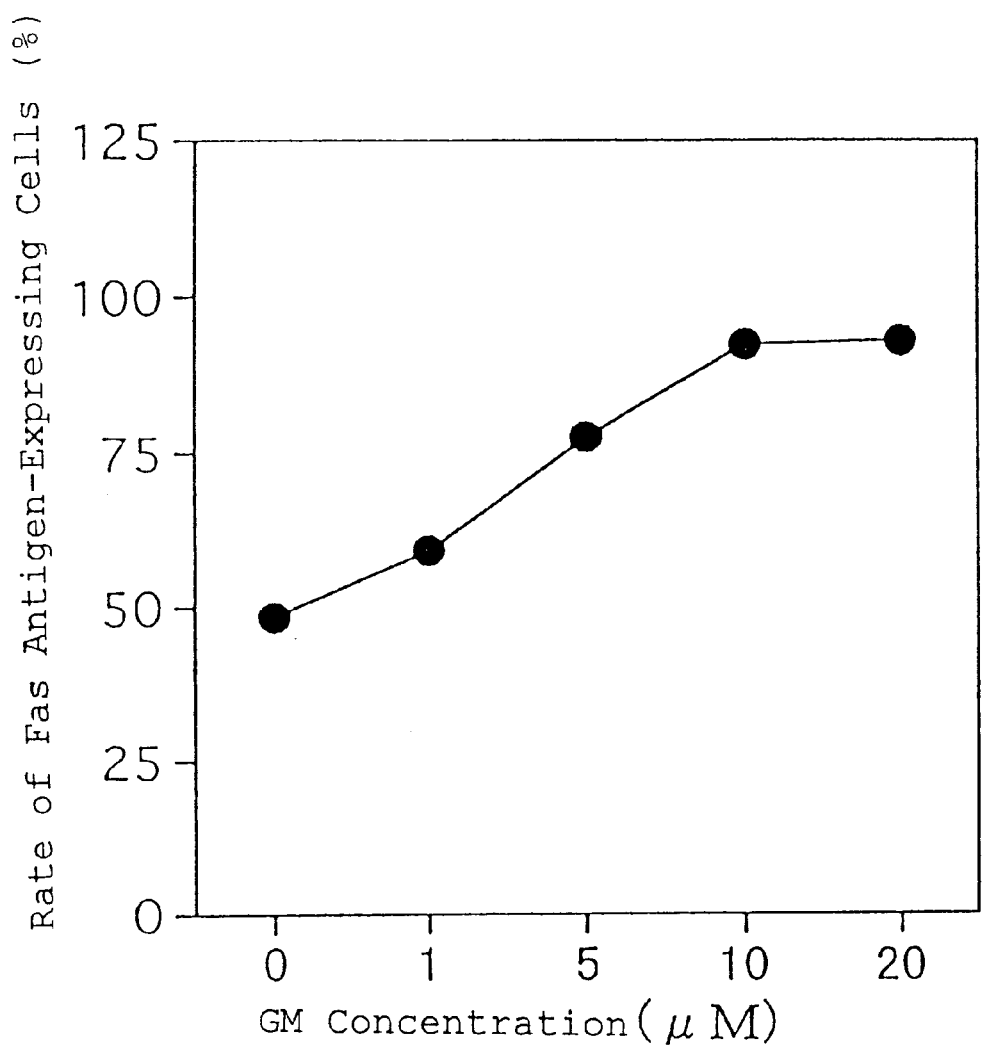
FIG. 36 shows expression of Fas antigen in Molt-3 cells.
Figure 37:
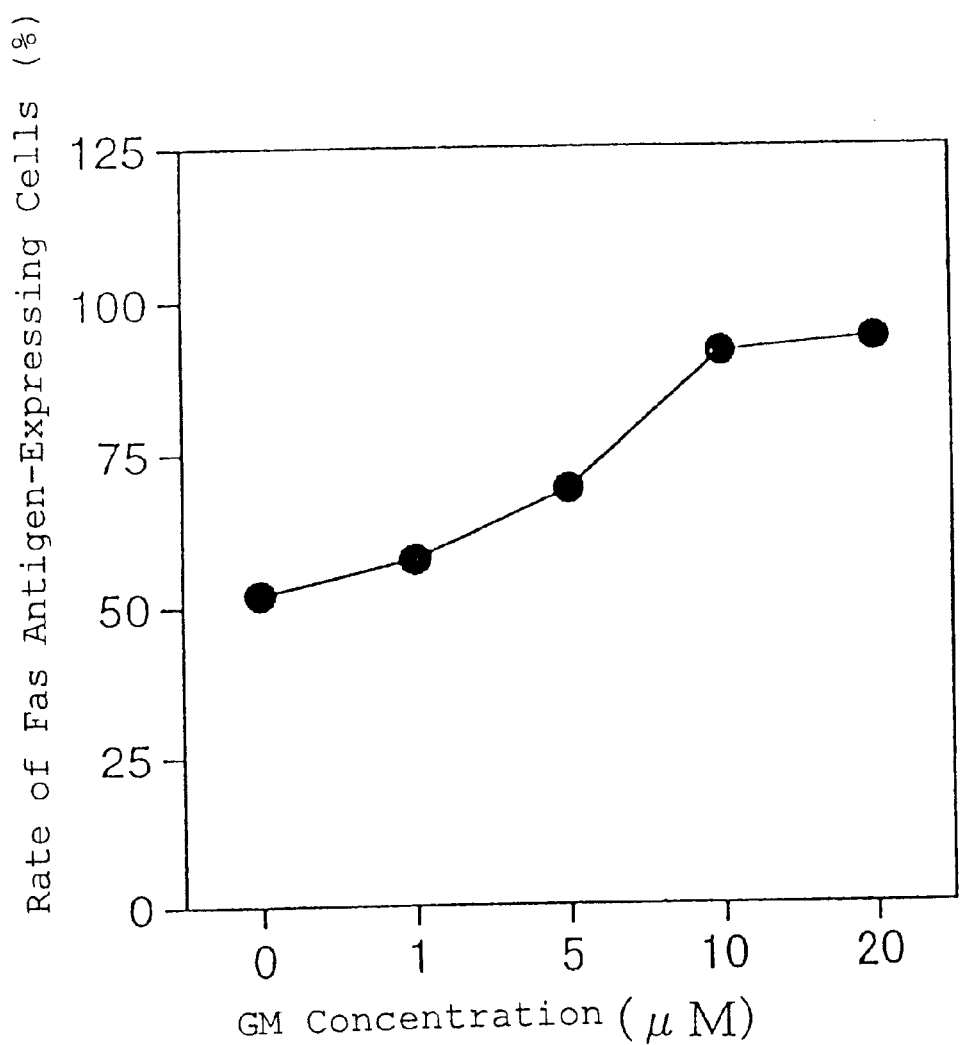
FIG. 37 shows expression of Fas antigen in Jurkat cells.

The results are shown in FIG. 36 and FIG. 37. Thus, FIG. 36 shows the expression of Fas antigen in Molt-3 cells while FIG. 37 shows that in Jurkat cells. In FIG. 36 and FIG. 37, abscissa indicates GM concentration (μM) while ordinate indicates the rate (%) of Fas antigen-expressing cells whereby an action of inducing the Fas antigen production by GM was noted.

(3) Molt-3 cells were incubated for 1, 3, 6, 12 or 24 hours after addition of 10 (i M of GM by the same manner as in Example 12-(2) and then the ratio of the cells which expressed Fas antigen was measured by the same method as in Example 12-(2)sa The result was that, when 10 μM of GM was added, the ratio of the Fas antigen-expressing cells increased after 12 hours from the incubation and further increase was noted after 24 hours.

Figure 38:
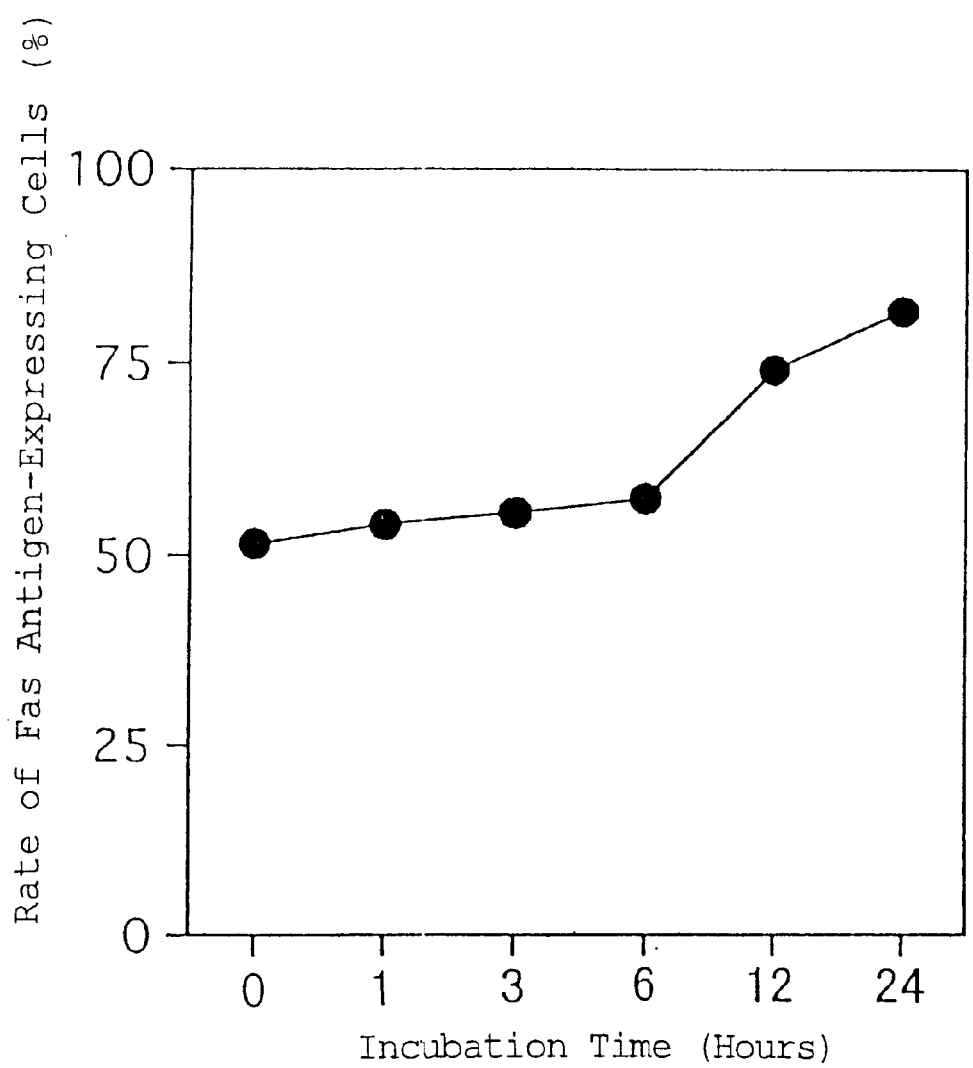
FIG. 38 shows a change in ratio of the cells expressing the Fas antigen.

The result is shown in FIG. 38. Thus, FIG. 38 shows a change in the ratio of Fas antigen expressing cells when incubation was conducted after adding 10 μM of GM to Molt-3 cells in which abscissa indicates incubation time (hours) while ordinate indicates the ratio (%) of Fas antigen-expressing cells.

Thus, as mentioned hereinabove in Example 12, an action of GM for inducing the expression of Fas antigen was ascertained. CM, GD, CD or each of the diastereomers thereof and each diastereomer of GM gave the similar results as well.

Example 13

Figure 39:
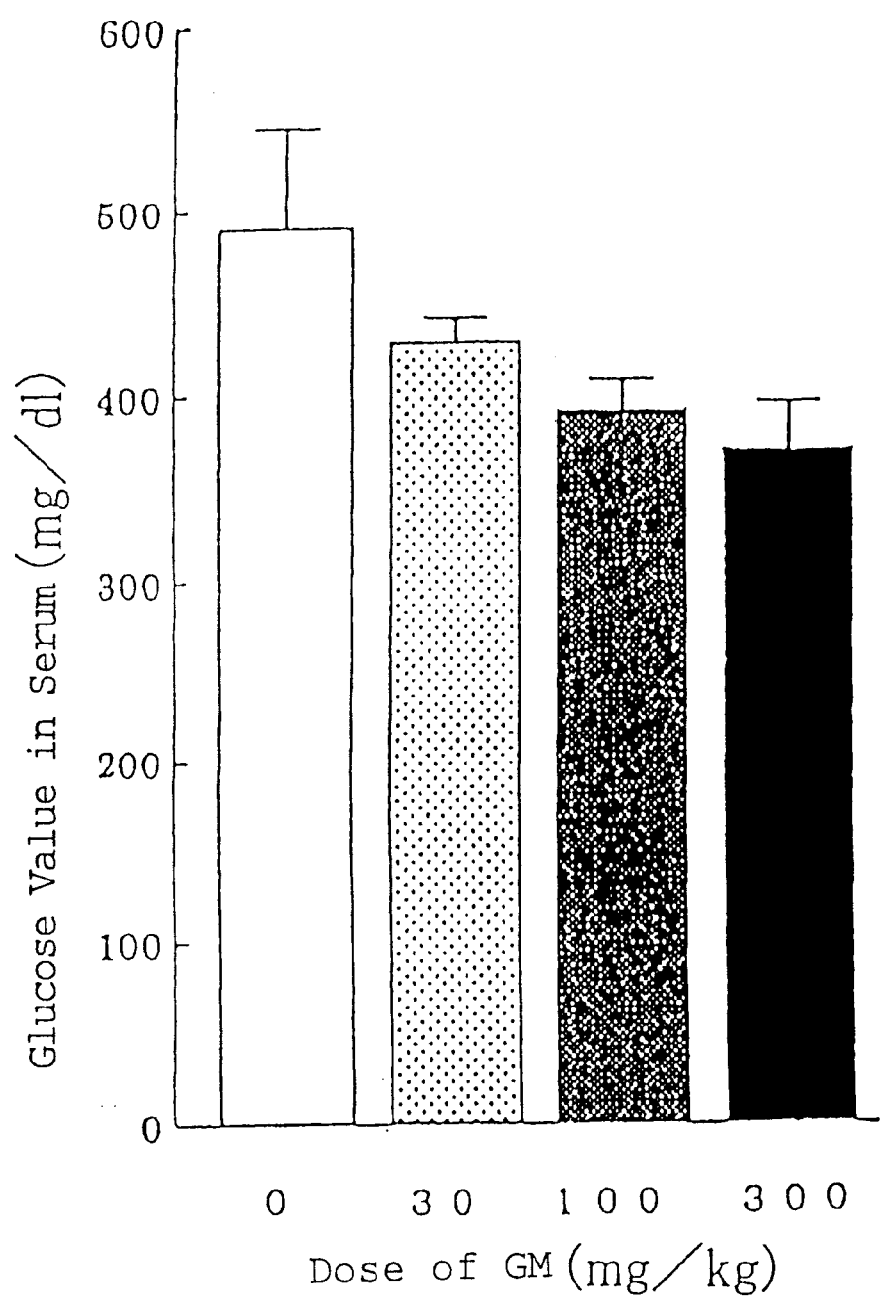
FIG. 39 shows a relation between the dose of GM and blood sugar level.
Figure 42:
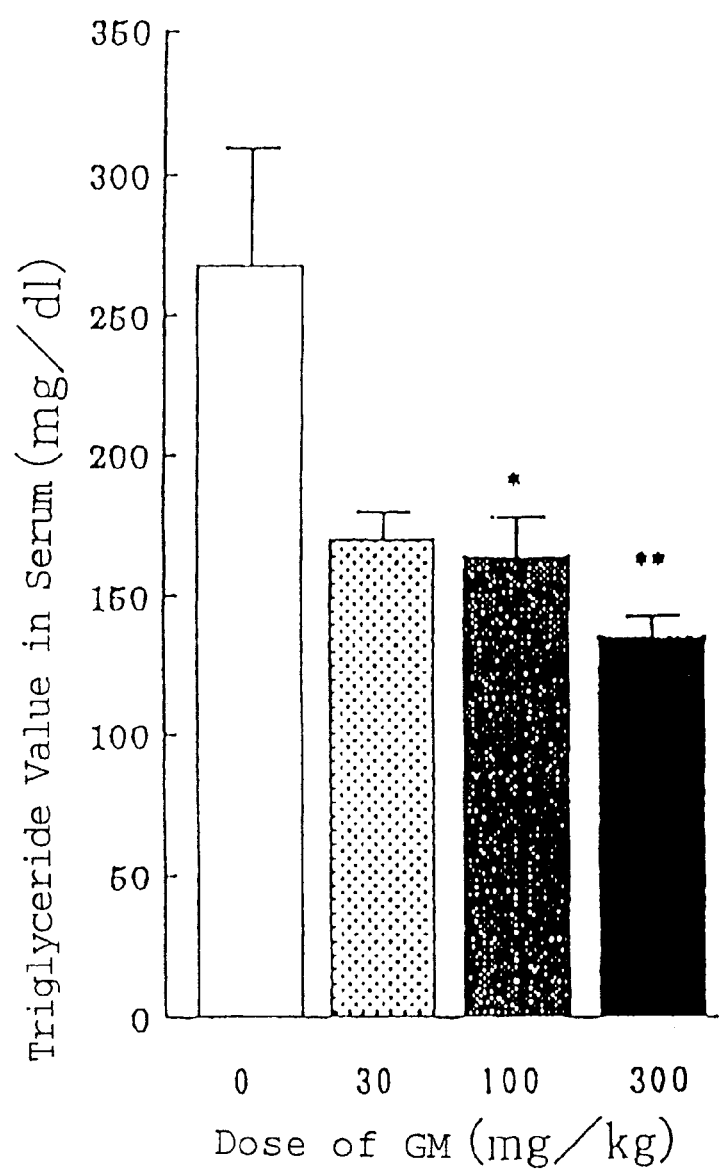
FIG. 42 shows the relation between the dose of GM and the triglyceride level in serum.
Figure 43:
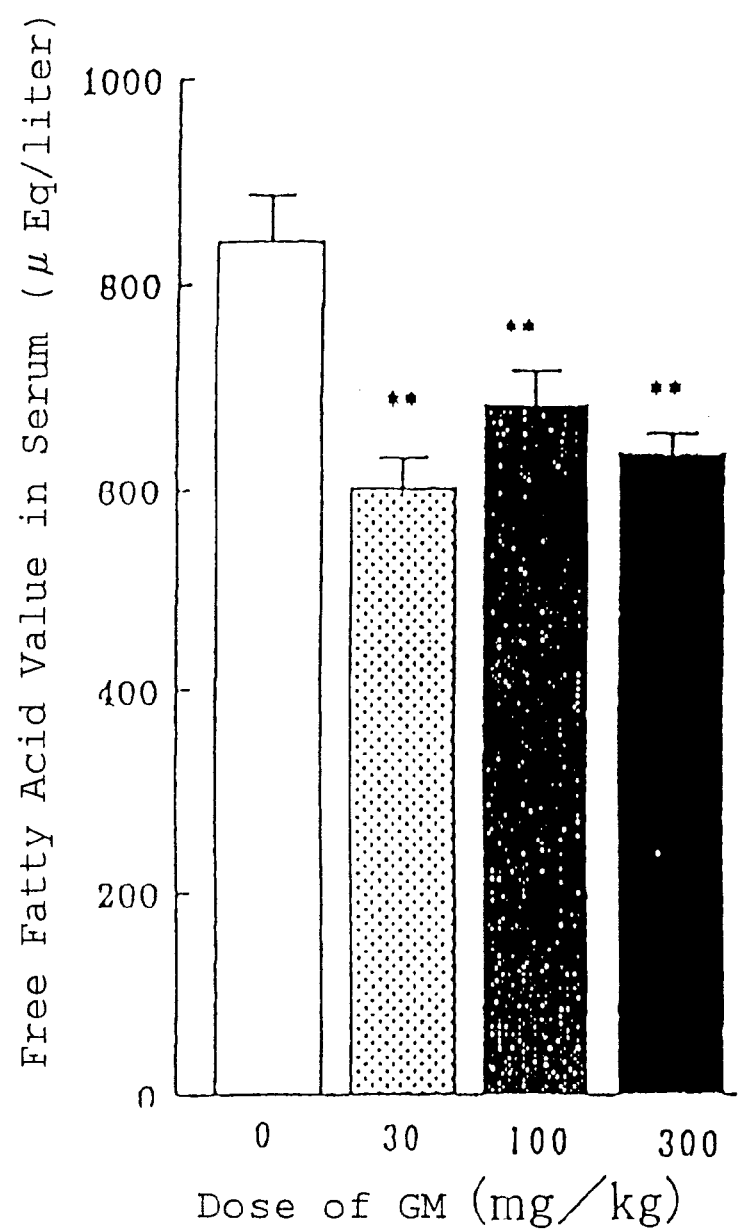
FIG. 43 shows the relation between the dose of GM and the free fatty acid level in serum.

KK-A$^y$ Mice (male; four weeks age) were purchased from Clea Japan and, after breeding at our end until ten weeks age, GM was orally administered for 21 days and its influence on sugar, insulin and lipid in blood was investigated. Doses of GM were 30, 100 and 300 mg/kg. Blood sugar decreased in each of the groups administered with GM (FIG. 39). Insulin in serum decreased in each of the groups administered with GM (FIG. 40)1 With regard to lipid in serum, total cholesterol in serum de creased in the GM-administered group (FIG. 41), triglycerides in serum decreased in the CM-administered group (FIG. 42) and free fatty acids in serum decreased in the GM-administered group (FIG. 43).

Figure 40:
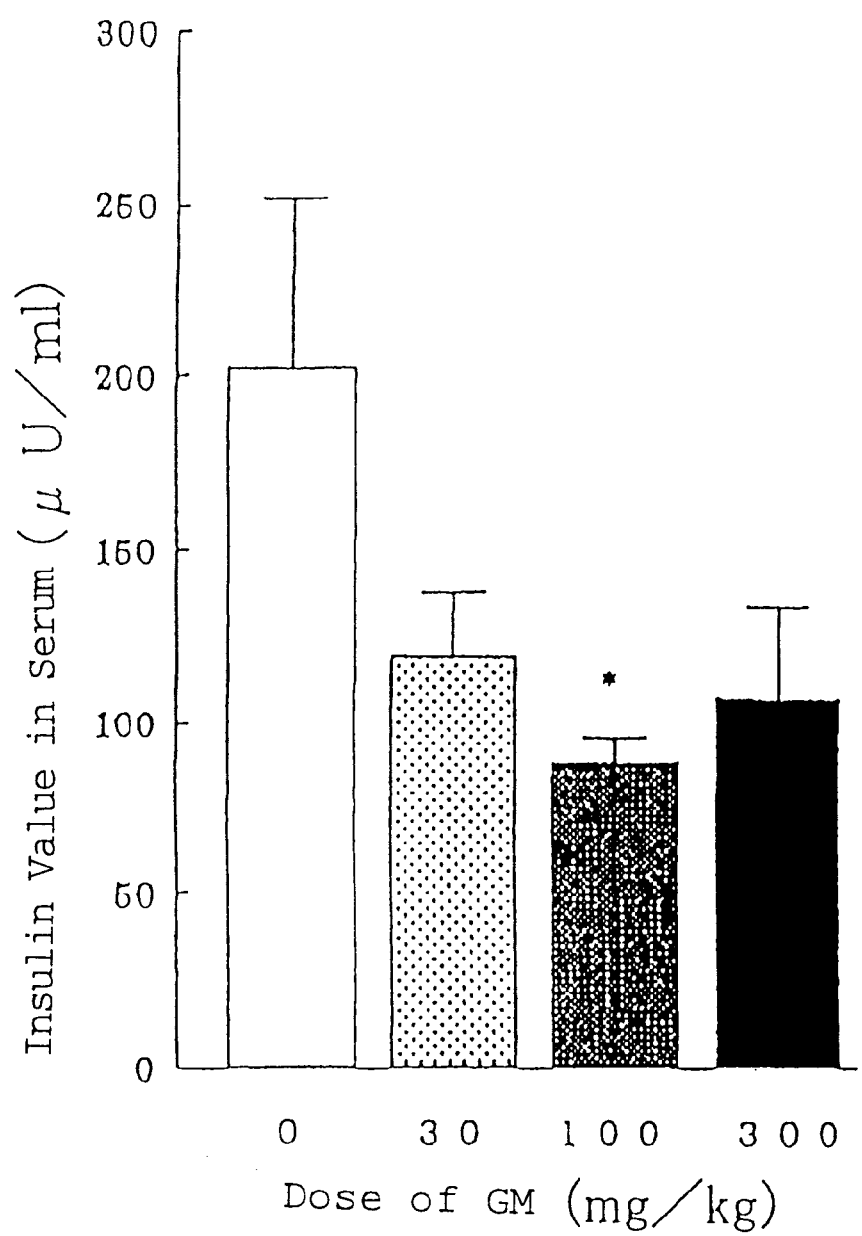
FIG. 40 shows a relation between the dose of GM and the insulin level in serum.
Figure 41:
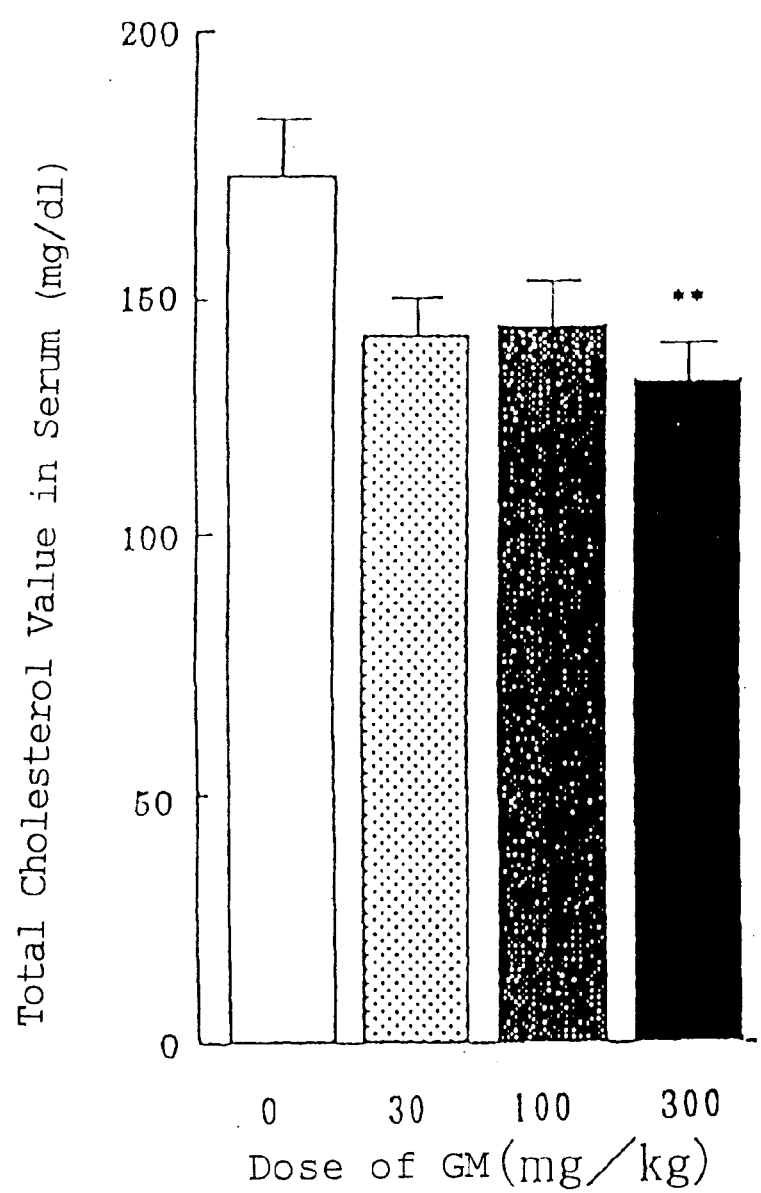
FIG. 41 shows a relation between the dose of GM and the total cholesterol level in serum.

Thus, FIG. 39 shows the relation between the dose of GM and blood sugar in which ordinate indicates glucose value in serum (mg/dl) while abscissa indicates dose of GM (mg/kg) FIG. 40 shows the relation between the dose of GM and insulin in serum in which ordinate indicates insulin value in serum ($\mu$U/ml) while abscissa indicates dose of GM (mg/kg) FIG. 41 shows the relation between the dose of GM and total cholesterol value in serum in which ordinate indicates total cholesterol value in serum (mg/dl) while abscissa indicates dose of GM (mg/kg). FIG. 42 shows the relation between the dose of GM and triglyceride value in serum in which ordinate indicates triglyceride value in serum (mg/dl) while abscissa indicates dose of GM (mg/kg) FIG. 43 shows the relation between the dose of GM and free fatty acid value in serum in which ordinate indicates free fatty acid value in serum ($\mu$Eg/liter) while abscissa indicates dose of GM (mg/kg). In the drawings, * and ** mean that significances in a Turkey's multiple comparative test to the group to which no GM was administered were $p<0.05$ and $p<0.01$, respectively.

Incidentally, the animals were grouped into four (each group consisting of ten animals) and the four groups were administered with physiological saline solution (5 ml/kg) or 30, 100 or 300 mg/5 ml/kg of GM. Each test substance was orally administered once daily for 21 days and, on the final day of administration, the animals were anesthetized with ether after four hours from the administration of the test substance and blood was collected from artery of lower abdomen. Insulin in serum was measured by an enzyme-immunoassay (commercially available kit: Glazym Insulin-EIATEST, manufactured by Wako Pure Chemicals). Sugar, triglycerides and free fatty acids in serum were measured using an automatic analyzer (type 7070, manufactured by Hitachi) by a hexonase-G6PDH method, a GPO•DAOS method and an ACS•ACOD method, respectively. Total cholesterol in serum was measured using an automatic analyzer (type 7070, manufactured by Hitachi) by a cholesterol-oxidase, DAOS method.

From the above results, GM was found to have an effect of lowering blood sugar, insulin and lipid. CM, GD, CD or each of diastereomers thereof and each diastereomer of GM gave similar results as well.

Example 14

(1) An RPMI 1640 medium (5 ml) containing 10% of fetal bovine serum which contained $2 \times 10^5$ cells/ml of HL-60 (ATCC CCL-24C) was placed in each well of a six-well plate, incubated at 37° C. for 24 hours in the presence of 5% of $CO_2$, then GM was added thereto to make its final concentration 0, 0.5, 1.0, 3.0, 5.0, 10.0 or 20.0 $\mu$M and the incubation was further continued for eight hours more.

After completion of the incubation, cell numbers were counted and the cells were recovered by centrifugation and washed with PBS to prepare GM-treated cells. In the meanwhile, cells which were heated at 45° C. for ten minutes followed by subjecting to the same incubation were prepared as well.

The cells treated as such were subjected to an SDS-PAGE by a method mentioned in "Molecular Cloning" [Cold Spring Harbor Laboratory Press, (1989)]. The treated cells were suspended in an SDS-PAGE sample buffer to make the concentration $2.5 \times 10^6$ cells/ml, the resulting cell suspension was treated at 100° C. for ten minutes and each 5 $\mu$l thereof was applied to two sheets of SDS-PAGE gels (5% stacking gel; 10% separation gel) to conduct an electrophoresis. One of the gels was stained with Coomassie Brilliant Blue R250 while another gel was subjected to a blotting to a polyvinylidene difluoride transfer membrane (Immobilon™, manufactured by Millipore, catalog no. IPVH000-10). The membrane was subjected to a blocking at 4° C. for one night with Block Ace (manufactured by Dainippon Pharmaceutical; catalog no. UK-B25).

The blocked membrane was made to react with monoclonal antibody HSP 72/73 (Ab-1) (manufactured by Oncogene Research Products, catalog no. HSP01) which specifically reacted with heat-induced heat shock protein of 70 kDa and washed with TBS containing 0.05% of Tween 20 followed by further washing with TBS. After that, it was made to react with peroxidase-compounded secondary antibody HRP-Rabbit Anti-Mouse IgG (H+L) (manufactured by Zymed Laboratories, catalog no. 61-6520) and washed by the same manner as in the above operation. The membranes which were treated with primary and secondary antibodies as such were made to react with Renaissance™ (a chemiluiminor reagent manufactured by Dupont NEN, catalog no. NEL-100) and photosensitized with an X-ray film to detect the induction of heat shock protein of 70 kDa.

The result was that, by addition of GM, induction of heat shock protein of 70 kDa was noted. Intensity of the induction is shown in Table 5. In Table 5, "+" indicates degree of intensity of induction and the more the numbers of "+", the more the intensity of induction. Incidentally, "−" means that no induction was noted and "±" means the induction was slight.

TABLE 5

| Treated Cells | Induction of Heat Shock Protein |
| --- | --- |
| Heated at 45° C. for 10 minutes | +++ |
| 0 $\mu$M of GM | − |
| 0.5 $\mu$M of GM | ± |
| 1.0 $\mu$M of GM | ± |
| 3.0 $\mu$M of GM | + |
| 5.0 $\mu$M of GM | + |
| 10 $\mu$M of GM | ++ |
| 20 $\mu$M of GM | ++ |

It is clear from Table 5 that GM has an HSP70-inducing ability.

(2) CM was added to the incubated cells to make its final concentration 0, 10, 20, 30, 40 or 50 $\mu$M and expression of HSP70 was measured by the method as mentioned in Example 14-(1).

The result ascertained that CM induced the heat shock protein of 70 kDa. Intensity of the induction is given in Table 6. In Table 6, "+" indicates degree of intensity of induction and the more the numbers of "+", the more the intensity of induction. Incidentally, "−" means that no induction was noted and "±" means the induction was slight.

TABLE 6

| Treated Cells | Induction of Heat Shock Protein |
|---|---|
| Heated at 45° C. for 10 minutes | +++ |
| 0 μM of CM | − |
| 5 μM of CM | − |
| 10 μM of CM | + |
| 20 μM of CM | ++ |
| 30 μM of CM | ++ |
| 40 μM of CM | + |
| 50 μM of CM | + |

Thus, as shown in Example 14, GM and CM showed an action of inducing the heat shock protein. GD, CD or each of diastereomers thereof and each diastereomer of GM and CM showed the similar result as well.

Example 15

GM (0, 4, 8 or 16 μM) was added to 2×10⁵ cell/ml of CEM-SS cells (ATCC CCL-119) and to CEM-SS cells infected with HIV-1$_{IIIB}$ (wherein not less than 90% of the CEM-SS cells were infected with the HIV-1$_{IIIB}$; hereinafter, referred to as CEM-3B) incubation was conducted for one day, viable cell numbers and dead cell numbers were counted and survival cell rate was calculated. The result was that, when GM was added to make its concentration 0, 4 or 8 μM, survival rate did not decrease in CEM-SS cells while, in CEM-3B cells, the survival rate significantly decreased depending upon the concentration of the added (G. In addition, in the case of addition of 16 μM, the survival rate of CEM-SS cells decreased as well but that of CEM-3B cells decreased more significantly. This means that GM showed an anti-HIV action.

Figure 44:
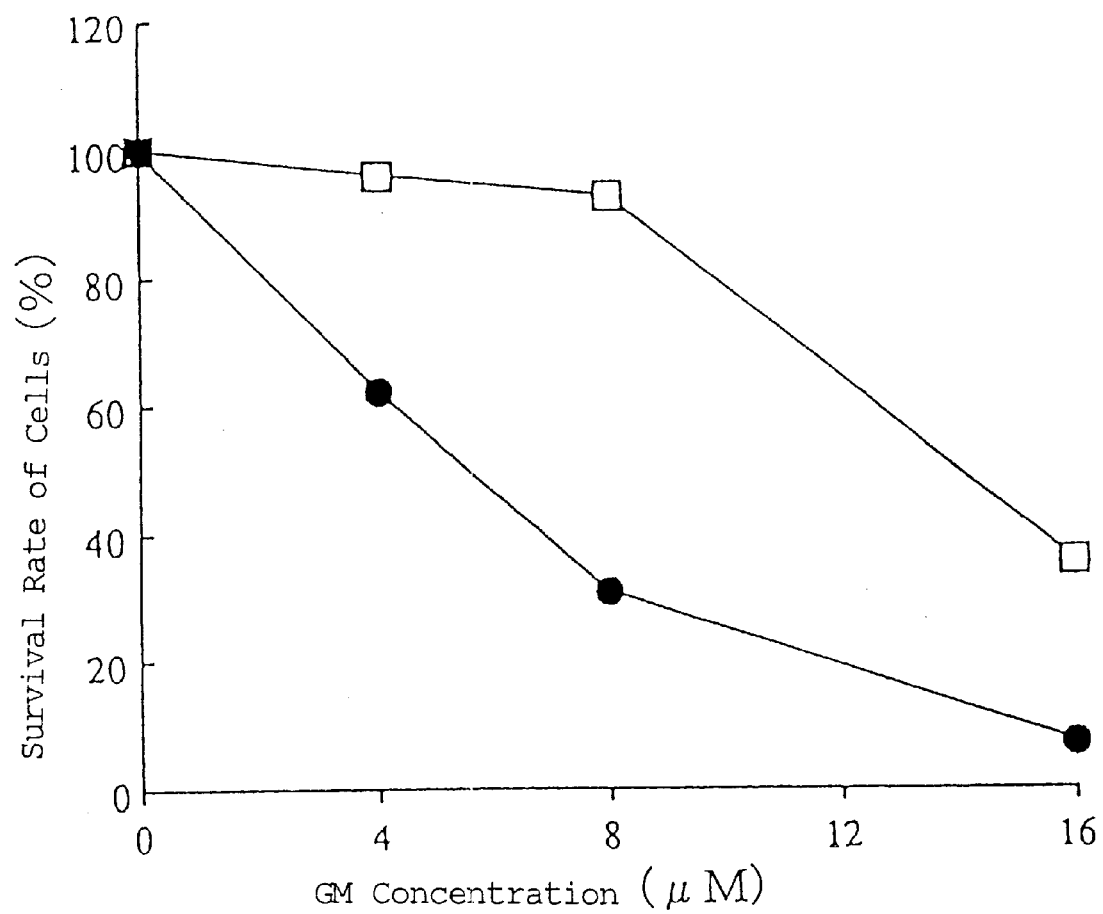
FIG. 44 shows the relation between the GM concentration and the viability of cells.

The result is given in FIG. 44. Thus, FIG. 44 shows the relation between the concentration of the added GM and the survival rate of the cells in which abscissa indicates the GM concentration (μM) while ordinate indicates the survival rate (%) after incubation for one day. Open square indicates the case where CEM-SS cells were used while black circle indicates the case where CEM-3B cells were used.

Figure 45:
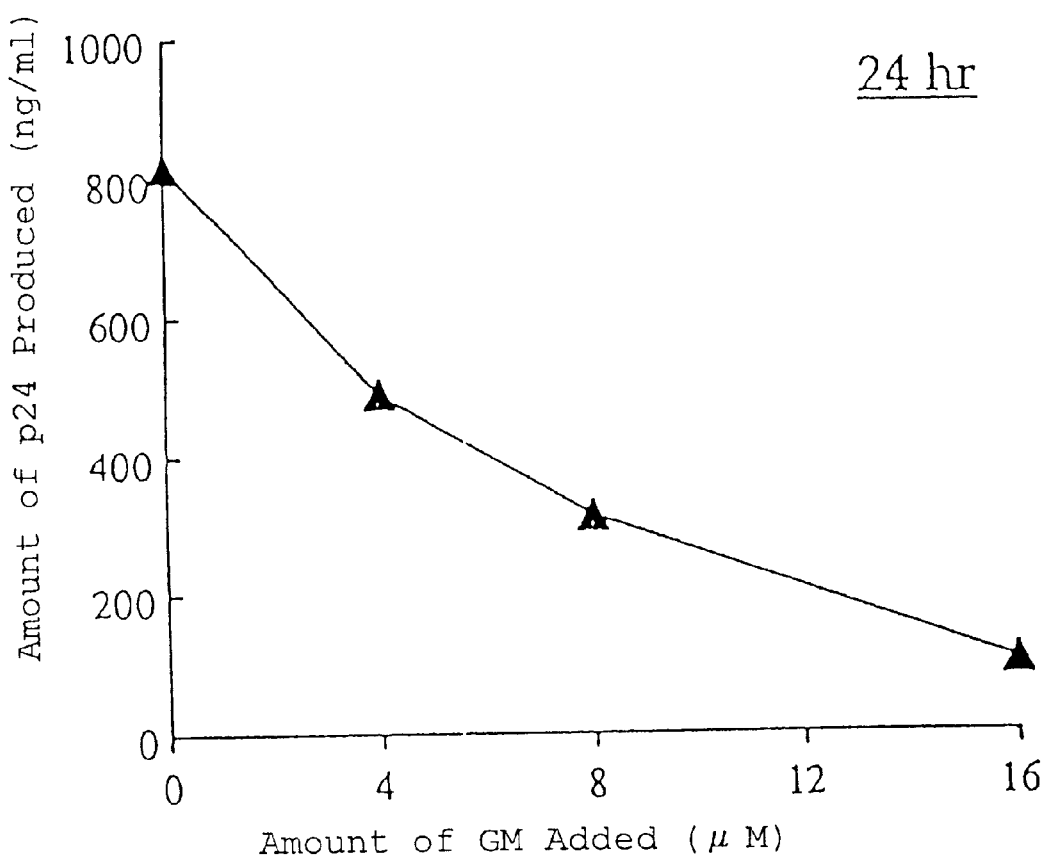
FIG. 45 shows the relation between the GM concentration and the amount of p24 produced.

(2) Concentration of p24 antigen contained in the supernatant liquid in the culture after incubation of the CEM-3B cells mentioned in Example 15-(1) for one day was measured. The result was that the p24 concentration decreased depending upon the concentration of the added GM whereby an anti-HIV action was noted. The result is shown in FIG. 45. Thus, FIG. 45 shows the relation between the concentration of added GM and the amount of produced p24 in the supernatant liquid of the culture in which abscissa indicates the amount of GM added (μM) while ordinate indicates the amount of p24 produced (ng/ml).

Thus, as shown in Example 15 hereinabove, GM showed a selective cytocidal effect to HIV-infected cells exhibiting an antiviral action to HIV. CM, GD, CD or each of the diastereomers thereof and each diastereomer of GM showed the similar result as well.

Example 16

(1) Transformation to *Escherichia coli* HB101 was conducted by control plasmid pcD2-Y expressing G418- resisting gene [Mol. Cell. Biol., volume 7, pages 2745–2752 (1987)] and plasmid pcD2-16E7 which was capable of expressing both HPV 16 type E7 and G418-resisting gene [Jpn. J. Cancer Res., volume 82, pages 1340–1343 (1991)], then incubation was conducted in an L-broth medium and plasmid was extracted from the collected cells and purified by a cesium chloride density gradient ultracentrifugation to give vector plasmid for introduction of gene.

NIH 3T3 cells were incubated at 37° C. under the condition of 5% $CO_2$ in a Dulbecco-modified Eagle's medium containing 10% of calf serum.

The purified plasmid (10 μg) was introduced into NIH 3T3 cells using a cationic liposome (TransIT LT-1, manufactured by Takara Shuzo), the cells were selected at 37° C. under the condition of 5% $CO_2$ for two weeks in a Dulbecco-modified Eagle's medium containing 10% calf serum which contained 0.4 mg/ml of G418 (Gibco) and the resulting colonies were cloned to establish each nine strains of NIH 3T3 cells into which control vector was introdcd and NIH 3T3 cells which was cancerated with HPV 16 type E7.

The cell strains into which control vector was introduced were named NIH 3T3/Y-1, NIH 3T3/Y-2, NIH 3T3/Y-3, NIH 3T3/Y-4, NIH 3T3/Y-5, NIH 3T3/Y-6, NIH 3T3/Y-7, NIH 3T3/Y-8 and NIH 3T3/Y-1).

The cells strains into which E7 was introduced were named NIH 3T3/E7-1, NIH 3T3/E7-2, NIH 3T3/E7-3, NIH 3T3/E7-4, NIH 3T3/E7-5, NIH 3T3/E7-6, NIH 3T3/E7-7, NIH 3T3/E7-8 and NIH 3T3/E7-9.

(2) NIH 3T3 cells, the cells strains into which control vector was introduced and the cell strains into which E7 was introduced were made to grow to an extent of 50–70% confluence in a Dulbecco-modified Eagle's medium containing 10% of calf serum using a 100 mm-tissue culture plate and washed with PBS and the cells were peeled off with a 0.25% trypsin-EDTA solution and suspended in 5 ml of Dulbecco-modified Eagle's medium containing 10% of calf serum.

A part of the suspension was taken out and cell density was counted by a Neubauer's hemocytometer. Based upon the resulting data, it was diluted with a Dulbecco-modified Eagle's medium containing 10% of calf serum and planted on a tissue culture plate having a diameter of 60 mm to make 200 cells/plate and incubation was started in 3 ml of the medium. After 24 hours from the initiation of the incubation, GM was added thereto to make its concentration 5 μM. After additional 24 hours, the medium was exchanged with a fresh one and GM was added thereto to make its concentration 5 μM.

After that, the medium was exchanged with a fresh one every two to three days followed by adding GM thereto to make its concentration 5 μM. A plate to which no GM was added was prepared as a control experimental section and incubated by the same manner. Each incubation was conducted in three series. After incubating for nine days, the medium was fixed by methanol and the colonies were stained with a Giemsa's solution (Gibco).

Incidentally, evaluation was conducted using NIH 3T3, NIH 3T3/Y-1 and NIH 3T3/E7-2.

Result of counting of the stained colonies is shown in Table 7. The cells into which E7 was introduced showed high sensitivity to GM as compared with the control cells. Thus, GM selectively acted the transformed cells with cancer gene. CM, GD, CD or each of the diastereomers thereof and each diastereomer of GM showed the similar results.

TABLE 7

| Cells | Numbers of Colonies (Mean Value ± SD) in | |
|---|---|---|
| | Control | GM-Treated Cells |
| NIH 3T3 | 91.7 ± 11.9 | 79.0 ± 2.6 |
| NIH 3T3/Y-1 | 83.3 ± 8.4 | 72.0 ± 9.5 |
| NIH 3T3/E7-2 | 67.3 ± 3.2 | 13.3 ± 3.2 |

Example 17

(1) One µl of 0.25 µg/µl pBR322 DNA (manufactured by Takara Shuzo) was added to a mixture of 2 µl of topoisomerase II (manufactured by TopoGEN, 2 units/µl), 2 µl of a buffer with a ten-fold diluted concentration [0.5M Tris-HCl (pH 8.0), 1.2M KCl, 0.1M $MgCl_2$, 5 mM adenosine triphosphate and 5 mM dithiothreitol], 2 µl of 0.1% bovine serum albumin (manufactured by Takara Shuzo), 11 µl of distilled water and 2 µl of distilled water (a control) or a sample (50, 100, 200, 500, 1000 or 2500 µM of GM) and made to react at 37° C. After the reaction for 30 minutes, the reaction was stopped by adding 2 µl aqueous solution of 1% sodium dodecylsulfate, 50% glycerol and 0.02% Bromophenol Blue.

The above reaction solution (20 µl) was applied to 1% agarose gel prepared from agarose L03 (manufactured by Takara Shuzo) and TAE buffer [40 mM Tris, 5 mM sodium acetate and 1 mM disodium ethylenediaminetetraacetate (EDTA); adjusted to pH 7.8 with acetic acid] and electrophoresis was conducted in the TAE buffer. After the electrophoresis, the gel was dipped in an aqueous solution of 1 µg/ml ethidium bromide and irradiated with ultraviolet ray to observe the electrophoretic pattern of DNA. In a control which was an aqueous solution, DNA completely changed from a supercoiled type to a relaxation type but, when topoisomerase II activity was inhibited, the change from a supercoild type to a relaxation type was partially or completely inhibited.

The result is shown in Table 8.

TABLE 8

| Concentration (µM) in Reaction Solution | Inhibiting Activity |
|---|---|
| 0 | − |
| 5 | − |
| 10 | + |
| 20 | ++ |
| 50 | ++ |
| 100 | +++ |
| 250 | +++ |

In the control where water was added, DNA completely changed from a supercoiled type to a relaxation type but, when the concentration of GM was 10 µM or higher, the change of DNA from a supercoiled type to a relaxation type was partially or completely inhibited whereby the activity of GM for inhibiting the topoisomerase II was ascertained. In Table 8,— means a complete change from a supercoiled type to a relaxation type; + means a change in a medium degree; ++ means that most of supercoiled type remained; and +++ means that there was no decrease in a supercoiled type at all.

(2) Activity of GM for inhibiting the topoisomerase I was measured by the same method as in Example 17-(1) except that topoisomerase I [manufactured by TopoGEN, 0.01 unit/y 1] was used instead of topoisomerase II; and 100 mM Tris-HCl (pH 7.9), 10 mM EDTA, 1 mM spermidine and 50% glycerol were used as a buffer with a ten-fold diluted concentration. Incidentally, as a sample, GM was added to make the final concentration 1 mM.

The result was that topoisomerase I was inhibited by 1 mM GM.

As such, GM showed an inhibiting activity to topoisomerase II which was expressed only transiently during a mitotic phase in normal cells but became to be expressed highly through whole cell cycle by canceration, and also to topoisomerase I which increases in its expressing amount and activity by canceration. CM, GD, CD or each of diastereomers thereof and each diastereomer of GM showed the similar results.

Example 18

C57BL/6 mice (female, five weeks age, body weight about 20 g) were purchased from Nippon SLC and used for the experiment after a preliminary breeding for one week at our end. Ovine erythrocyte (manufactured by Shimizu Jikken Zairyo) which is an antigen provoking the sensitivity reaction of a delayed type was washed three times with a physiological saline solution (manufactured by Otsuka Pharmaceutical) to make 1×09 cells/ml and 203 µl of it was intraperitoneally injected to mice to subject to an antigen sensitization.

After five days from the sensitization, 40 µl of antigen which was prepared by the same manner was injected to right paw to induce an antigen whereby pedal edema was provoked. From the antigen-sensitized date, GM was intraperitoneally administered to mice (one group consisting of five mice) once daily at the dose of 30 mg/kg or 300 mg/kg for three days.

After two days from the antigen induction, volume of right paw of the mice was measured by a measuring device for pedal edema (manufactured by Ugo Basile) and used as an index for the sensitivity reaction of a delayed type. The measured value was given by calculating the increasing rate from the right paw volume of the mice measured before the antigen induction.

Figure 46:
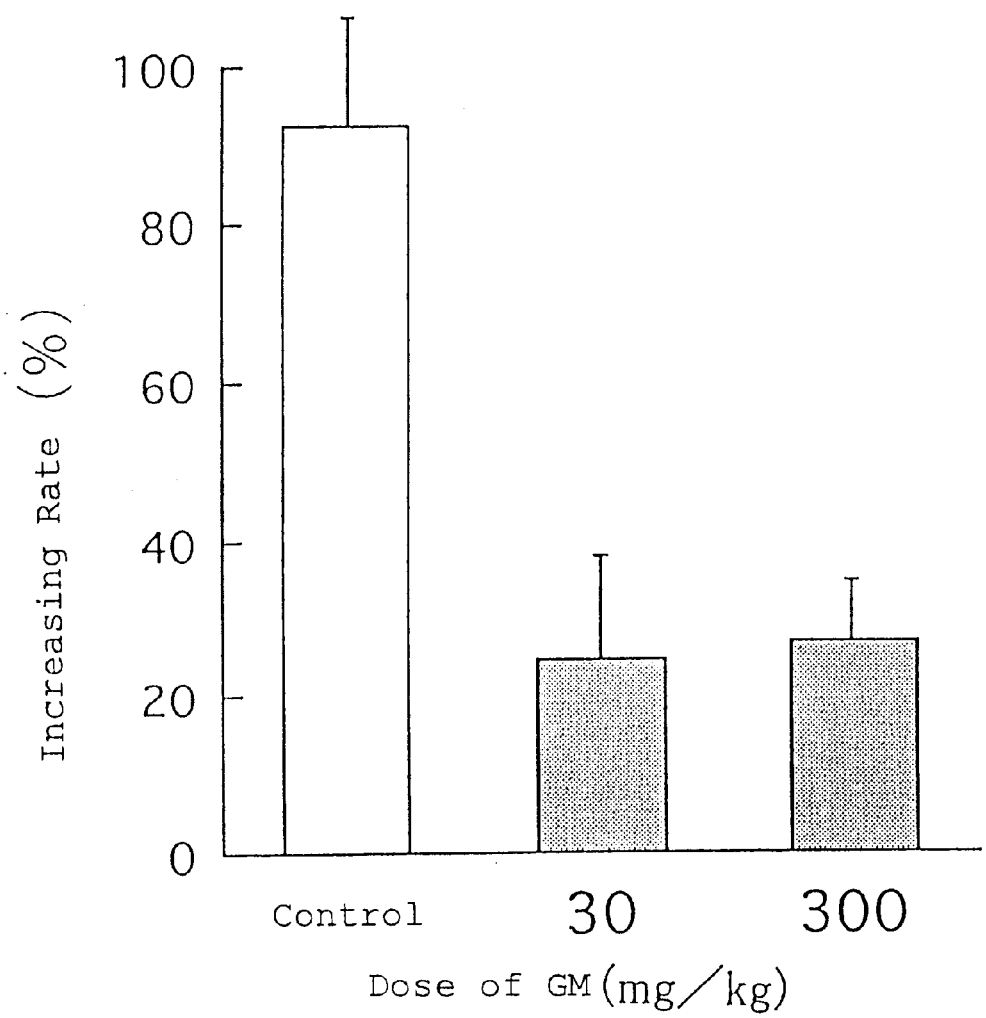
FIG. 46 shows an inhibition activity of GM to a delayed type hypersensitivity.

The result is given in FIG. 46. Thus, FIG. 46 shows an inhibiting action of GM to a sensitivity reaction of a delayed type in which ordinate is an increasing rate (%) while abscissa is a dose of GM (mg/kg).

GM showed a significant inhibiting action to a sensitivity reaction of a delayed type by administration of 30 and 300 mg/kg. CM, GD, CD or each of the diastereomers thereof and each diastereomer of GM showed the similar result as well.

Example 19

Yale rats of Wistar strain of five weeks age (one group consisting of five rats) (Nippon SLC) were sensitized by an intraperitoneal injection of 100 µl of 0.01% solution of egg white albumin (Sigma) in an aqueous physiological saline solution and 100 µl of Alum (trade name: Imject Alum; Pierce) and, after 14 days, blood was collected from abdominal artery.

The collected blood was centrifuged (at 2000 rpm for five minutes), plasma was separated and the amount of antigen-specific IgE was measured by a 48-hour rat passive cutaneous anaphylaxis (PCA) reaction.

Thus, serum was diluted with a physiological saline solution in a successively doubling manner ranging from 1/4 to 1/64 and each 0.1 ml thereof was subcutaneously injected to hair-clipped back of male rats of Wistar strain of seven weeks age. After 48 hours from the subcutaneous injection, 1 ml of a mixture of 0.05% egg white albumin and 0.5% Evans Blue (manufactured by Nacalai Tesque) was injected from tail vein. After 30 minutes from the injection from the tail vein, rats were subjected to decapitation and to exanguinated death, blue spots appeared on the back were observed, the spots with a diameter of 5 mm or more were judged to be positive and the highest dilution was adopted as an IgE titer.

In the GM-administered groups, 3 mg/kg or 30 mg/kg of GM was intraperitoneally administered once daily for three days from the antigen-sensitized day while, in the control group, distilled water was intraperitoneally administered by the same manner. The result is given in Table 9.

TABLE 9

|  | IgE Titer |
| --- | --- |
| Control Group | 64 |
| GM (3 mg/kg/day) | 32 |
| GM (30 mg/kg/day) | 8 |

An increase in the antigen-specific IgE amount by sensitization with egg white albumin was inhibited by administration of GM in a dose-dependent manner. Similar inhibiting activity to IgE production was noted in CM, GD, CD or each of the diastereomers thereof and each diastereomer of GM as well.

Example 20

Injection Preparations (1) CM was added to a physiological saline solution (as listed in the Japanese Pharmacopoeia) in a concentration of 1% to prepare an injection preparation.

(2) GM and glycyrrhizic acid were added to a physiological saline solution (the same as above) in concentrations of 0.5% and 0.1%, respectively, to prepare an injection preparation.

Example 21

Tablets (1) A tablet containing 100 mg of CD and an appropriate amount of microcrystalline cellulose was prepared and coated with sugar to manufacture a tablet preparation.

(2) A tablet containing 0.1 mg of GD, 10 mg of dipotassium glycyrrhizinate and an appropriate amount of microcrystalline cellulose was prepared and coated with sugar to manufacture a tablet preparation.

Example 22

Ointment

GM 1 g
Absorption ointment (as listed in the
Japanese Pharmacopoeia) 99 g

First, GM was well kneaded with a small amount of absorption ointment and then the residual absorption ointment was gradually added thereto and kneaded therewith until homogeneity was resulted to prepare an ointment preparation.

This ointment was applied to the affected part for four to five times a day.

MERIT OF THE INVENTION

The present invention offers the compound of the present invention or an optically active substance or a salt thereof which exhibits various physiological activities such as anticancer activity, inhibition activity to growth of cancer cells, induction activity of cancer cell differentiation, apoptosis induction activity, antibacterial activity, antiviral activity, improving activity of hepatic function, inhibition activity to production of tumor necrosis factor, inhibition activity to production of NO and antirheumatic action. It also offers a pharmaceutical agent containing at least one compound selected from the above compounds as an effective component. Said pharmaceutical agent is useful as a preparation for therapy or for prevention of diseases showing sensitivity to those compounds and is particularly useful as biophylaxic agent such as antiallergic agent, antirheumatic agent, remedy for diabetes mellitus and anticancer agent, agent against pathogenic microbes such as antiviral agent and antibacterial agent, and immunomodulator.

Further, in accordance with the present invention, it is now possible that an appropriate amount of the compound of the present invention, an optically active substance thereof or a salt thereof having a physiological activity is contained in food or beverages. Because of various physiological activities of those compounds such as anticancer action, differentiation inducing action, inhibiting action to the growth of abnormal cells, apoptosis inducing action, antiviral action, antibacterial action, action for improving the hepatic function and immunomodulating action, food or beverage offered by the present invention is a health food or beverage having a function of keeping homeostatis of living body such as prevention of carcinogenicity, anticancer effect, effect of preventing the viral diseases, antibacterial effect and apoptosis inducing action and the present invention offers food or beverage containing a functional substance useful for keeping the good health of stomach and intestine.

What is claimed is:

1. A compound represented by the following formula [I] or an optically active substance or a salt thereof

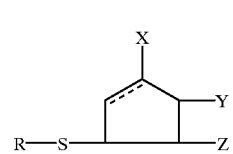

[I]

(in the formula, a bond shown by a dotted line in the five-membered ring means that said five-membered ring may be any of a cyclopentene ring having a double bond and a cyclopentane ring where said bond is saturated and, in the case of a cyclopentene ring, X is OH, Y is =O and Z is H while, in the case of a cyclopentane ring, X is =O, Y is OH and Z is OH, R is a residue after removal of an SH group from the SH-containing compound).

2. A compound or an optically active substance thereof or a salt thereof according to claim 1 in which said compound is represented by the following formula [II]

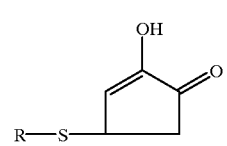

[II]

(in the formula, R is a residue after removing an SH group from the SH-containing compound).

3. A compound or an optically active substance or a salt thereof according to claim 1 in which said compound is represented by the following formula [III]

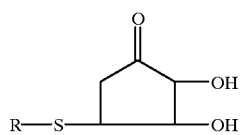

(in the formula, R is a residue after removing an SH group from the SH-containing compound).

4. A compound or an optically active substance thereof or a salt thereof according to any of claims 1–3 in which the SH-containing compound is an SH-containing amino acid or derivative thereof.

5. A compound or an optically active substance thereof or a salt thereof according to claim 4 in which the SH-containing compound is cysteine or glutathione.

6. A method for the manufacture of the compound represented by the formula [I] or an optically active substance thereof or a salt thereof, characterized in that, a compound selected from 4,5-dihydroxy-2-cyclopenten-1-one represented by the following formula [IV] or an optically active substance thereof or a salt thereof is made to react with a compound containing an SH group

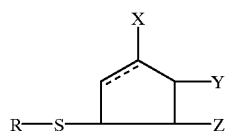

(in the formula, a bond shown by a dotted line in the five-membered ring means that said five-membered ring may be any of a cyclopentene ring having a double bond and a cyclopentane ring where said bond is saturated and, in the case of a cyclopentene ring, X is OH, Y is =O and Z is H while, in the case of a cyclopentane ring, X is =O, Y is OH and Z is OH, R is a residue after removal of an SH group from the SH-containing compound)

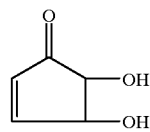

7. A method for the manufacture of a compound, an optically active substance thereof or a salt thereof according to claim 6 in which the compound represented by the formula [I] is a compound represented by the following formula [II]

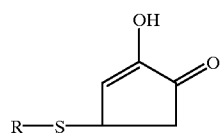

(in then formula, R is a residual group upon removal of an SH group from an SH-containing compound).

8. A method for the manufacture according to claim 7 in which the reaction is conducted under an acidic condition.

9. A method for the manufacture of a compound, an optically active substance thereof or a salt thereof according to claim 6 in which the compound represented by the formula [I] is a compound represented by the following formula [III]

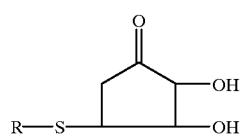

(in the formula, R is a residual group upon removal of an SH group from an SH-containing compound).

10. A method for the manufacture according to claim 9 in which the reaction is conducted under a neutral condition.

11. A method for the manufacture of a compound, an optically active substance thereof or a salt thereof according to any of claims 6–10 in which the SH-containing compound is an SH-containing amino acid or derivative thereof.

12. A method for the manufacture of a compound, an optically active substance thereof or a salt thereof according to claim 11 in which the SH-containing compound is cysteine or glutathione.

13. A pharmaceutical agent which is characterized in containing at least one compound selected from a compound represented by the following formula [I] or an optically active substance thereof or a salt thereof as an effective component

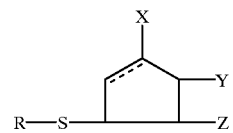

(in the formula, a bond shown by a dotted line in the five-membered ring means that said five-membered ring may be any of a cyclopentene ring having a double bond and a cyclopentane ring where said bond is saturated and, in the case of a cyclopentene ring, X is OH, Y is =O and Z is H while, in the case of a cyclopentane ring, X is =O, Y is OH and Z is OH, R is a residue after removal of an SH group from the SH-containing compound).

14. A pharmaceutical agent according to claim 13 in which said agent contains at least one compound represented by the following formula [II] or an optically active substance thereof or a salt thereof as an effective component

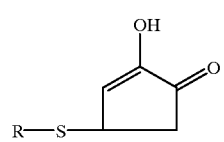

(In the formula, R is a residue after removing an SH group from the SH-containing compound).

15. A pharmaceutical agent according to claim 13 in which said agent contains at least one compound represented by the following formula [III] or an optically active substance thereof or a salt thereof as an effective component

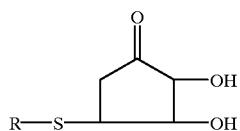

[III]

(in the formula, R is a residue after removing an SH group from the SH-containing compound).

16. A pharmaceutical agent according to claim 13 in which the SH-containing compound is an SH-containing amino acid or derivative thereof.

17. A pharmaceutical agent according to claim 16 in which the SH-containing compound is cysteine or gutathione.

18. A pharmaceutical agent according to any of claims 13–17 in which the pharmaceutical agent is selected from a group consisting of a biophylaxic agent, an agent for therapy of diabetes mellitus, an agent for prevention of diabetes mellitus, an anticancer agent, an apoptosis-inducing agent, an agent against pathogenic microbes, an agent for therapy of hyperlipemia, an agent for prevention of hyperlipemia, an agent for improving the hepatic function, and an agent for inducing the heat shock protein.

19. A pharmaceutical agent according to claim 18 in which the biophylaxic agent is selected from a group consisting of an antiallergic agent, an antirheumatic agent, an anti-inflammatory agent, an inflammation preventer, an interferon inducer, an inhibitor of tumor necrosis factor production, a preventer of tumor necrosis factor production, an enhancer of interleukin-10 production, an inhibitor of nitrogen monoxide production, an inducer of Fas antigen production, an immunomodulator, an inhibitor of IgE production, a therapeutic agent to autoimmune diseases, and an inhibitor of delayed type hypersensitivity.

20. A pharmaceutical agent according to claim 18 in which the agent against pathogenic microbes is an antibacterial agent or an antiviral agent.

21. A pharmaceutical agent according to claim 20 in which the antiviral agent is an antiviral agent for human acquired immunodeficiency virus or for C type hepatitis virus.

22. A pharmaceutical agent according to claim 20 in which the antiviral agent is an antiviral agent for human beings, for non-human animals, or for plants.

* * * * *